US012760264B2

(12) United States Patent
Azizgolshani et al.

(10) Patent No.: US 12,760,264 B2
(45) Date of Patent: Oct. 13, 2026

(54) APPARATUS FOR MODIFICATION OF CELLS

(71) Applicant: THE CHARLES STARK DRAPER LABORATORY, INC., Cambridge, MA (US)

(72) Inventors: Hesham Azizgolshani, Belmont, MA (US); Jonathan R. Coppeta, Windham, NH (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 659 days.

(21) Appl. No.: 17/821,144

(22) Filed: Aug. 19, 2022

(65) Prior Publication Data

US 2023/0073620 A1 Mar. 9, 2023

Related U.S. Application Data

(60) Provisional application No. 63/235,584, filed on Aug. 20, 2021.

(51) Int. Cl.

| | |
|---|---|
| ***C12M 1/00*** | (2006.01) |
| ***C12M 1/12*** | (2006.01) |
| ***C12M 1/34*** | (2006.01) |
| ***C12M 3/00*** | (2006.01) |
| ***C12N 15/86*** | (2006.01) |

(52) U.S. Cl.

CPC ............ *C12M 41/46* (2013.01); *C12M 23/40* (2013.01); *C12M 25/02* (2013.01); *C12M 29/04* (2013.01); *C12M 29/18* (2013.01); *C12M 41/12* (2013.01); *C12N 15/86* (2013.01)

(58) Field of Classification Search

CPC .............................. C12M 23/40; C12M 41/46

See application file for complete search history.

(56) References Cited

U.S. PATENT DOCUMENTS

| | | | | |
|---|---|---|---|---|
| 2007/0122904 | A1 | 5/2007 | Nordon | |
| 2008/0220523 | A1* | 9/2008 | Antwiler ................ | C12M 29/10 435/394 |
| 2019/0085280 | A1 | 3/2019 | Kotz | |
| 2021/0047602 | A1* | 2/2021 | Vang ...................... | C12M 35/08 |
| 2023/0212495 | A1* | 7/2023 | Moore ................... | C12M 25/10 435/285.1 |

FOREIGN PATENT DOCUMENTS

| | | | |
|---|---|---|---|
| EP | 0 479 492 | A1 | 4/1992 |
| WO | 2021/251447 | A2 | 12/2021 |

OTHER PUBLICATIONS

International Search Report for PCT/US2022/040960 dated Dec. 15, 2022, 4 pages.

* cited by examiner

*Primary Examiner* — Nathan A Bowers

(74) *Attorney, Agent, or Firm* — Brooks Kushman P.C.

(57) ABSTRACT

Devices for treatment of cells are disclosed. The devices include an elongated housing and at least one hollow fiber semi-permeable membrane positioned within the housing having a plurality of pores dimensioned to prevent passage of the cells to be treated. Systems for treatment of cells including the device are disclosed. Methods of treating cells, including transducing cells and activating cells, are also disclosed. The methods include introducing a biosample with cells to be treated into the device, introducing media to suspend and release treated cells into the device, and discharging the treated cells from the device.

22 Claims, 29 Drawing Sheets

APPARATUS FOR MODIFICATION OF CELLS

CROSS-REFERENCE TO RELATED APPLICATIONS

This application claims priority under 35 U.S.C. § 119(e) to U.S. Provisional Patent Application Ser. No. 63/235,584, titled "APPARATUS FOR MODIFICATION OF CELLS," filed Aug. 20, 2021, which is incorporated by reference herein in its entirety for all purposes.

FIELD OF TECHNOLOGY

Aspects and embodiments disclosed herein relate to devices, systems, and methods for the treatment of cells. In particular, aspects and embodiments disclosed herein relate to devices, systems, and methods for transduction and activation of cells.

SUMMARY

In accordance with one aspect, there is provided a system for treatment of cells with particles. The system may comprise a treatment device. The treatment device may comprise an elongated housing having a luminal inlet on a first end, a luminal outlet on a second end, and a housing inlet and a housing outlet. The treatment device may comprise at least one hollow fiber semi-permeable membrane positioned within the elongated housing extending between the luminal inlet and the luminal outlet to define an interior flow chamber and an exterior flow chamber, the hollow fiber semi-permeable membrane having a plurality of pores dimensioned to prevent passage of cells to be treated and the particles and allow passage of inhibitory factors. The luminal inlet may be constructed and arranged to receive the cells to be treated and the particles. The system may comprise a source of a biosample comprising the cells to be treated fluidly connected to the luminal inlet. The system may comprise a source of a treatment agent comprising the particles fluidly connected to the luminal inlet. The system may comprise at least one source of a media fluid independently fluidly connected to one of the luminal inlet and the luminal outlet, and one of the housing inlet and the housing outlet.

In some embodiments, the source of the biosample is fluidly connected to the source of the treatment agent upstream from the luminal inlet to produce a mixed sample comprising the cells to be treated and the particles.

In some embodiments, the system further comprises a mixer fluidly connected to the source of the biosample and the source of the treatment agent, configured to produce the mixed sample.

In some embodiments, the mixed sample is substantially homogenous.

In some embodiments, the biosample and the treatment agent are each independently fluidly connected to the luminal inlet.

In some embodiments, the system further comprises a priming fluid fluidly connected to at least one of the luminal inlet and the luminal outlet.

In some embodiments, the particles comprise viral particles or activation particles.

In some embodiments, the cells to be treated comprise at least one of stem cells, immune cells, cancer cells, engineered cells, primary cells, T-cells, primary T-cells, regulatory T-cells, NK cells, B cells, and hematopoietic stem cells (HSC).

In some embodiments, the system further comprises at least one of a luminal inlet pump, a housing inlet pump, a luminal inlet valve, a luminal outlet valve, a housing inlet valve, a housing outlet valve, a biosample valve, a treatment agent valve, and at least one media fluid valve.

In some embodiments, at least one of the luminal inlet pump and the housing inlet pump is configured to operate at an oscillatory flow.

In some embodiments, the system further comprises a controller operably connected to at least one of the luminal inlet pump, the housing inlet pump, the luminal inlet valve, the luminal outlet valve, the housing inlet valve, the housing outlet valve, the biosample valve, the treatment agent valve, and the at least one media fluid valve.

In some embodiments, the controller is configured to actuate at least one of the luminal inlet pump, the luminal inlet valve, the biosample valve, the treatment agent valve, and the housing inlet valve to introduce the biosample comprising the cells to be treated and/or the treatment agent comprising the particles. The controller may be configured to actuate at least one of the luminal inlet pump, the luminal inlet valve, the at least one media fluid valve, and the housing outlet valve to introduce the media fluid to co-localize the cells to be treated and the particles on a surface of the hollow fiber semi-permeable membrane.

In some embodiments, the controller is configured to actuate at least one of the luminal inlet pump, the luminal inlet valve, the at least one media fluid valve, and the luminal outlet valve to introduce the media fluid to suspend the treated cells in an intermediate sample. The controller may be configured to actuate at least one of the housing inlet pump, the housing inlet valve, the at least one media fluid valve, and the housing outlet valve to introduce the media fluid to release the treated cells from a surface of the hollow fiber semi-permeable membrane. The controller may be configured to actuate at least one of the luminal outlet valve and the luminal inlet valve to remove a treated cell sample comprising the treated cells and the particles from the treatment device.

In some embodiments, the system further comprises a pressure sensor configured to measure pressure at a target location within the system.

In some embodiments, the pressure sensor is operably connected to the controller, the controller configured to actuate one or more of the luminal inlet pump, the housing inlet pump, the luminal inlet valve, the luminal outlet valve, the housing inlet valve, the housing outlet valve, the biosample valve, the treatment agent valve, and the at least one media fluid valve responsive to a pressure measurement obtained by the pressure sensor.

In some embodiments, the system further comprises a weight sensor configured to measure weight at a target location within the system.

In some embodiments, the weight sensor is operably connected to the controller, the controller configured to notify a user responsive to a weight measurement obtained by the weight sensor.

In some embodiments, the system further comprises a bubble sensor configured to detect bubbles within the treatment device.

In some embodiments, the bubble sensor is operably connected to the controller, the controller configured to actuate one or more of the luminal inlet pump, the housing inlet pump, the luminal inlet valve, the luminal outlet valve, the housing inlet valve, the housing outlet valve, the biosample valve, the treatment agent valve, and the at least one media fluid valve responsive to a bubble detected by the bubble sensor.

In some embodiments, the system further comprises a pH control unit configured to control pH of a fluid within the treatment device.

In some embodiments, further comprises a pH sensor operably connected to the pH control unit configured to control pH within the treatment device responsive to a pH measurement obtained by the pH sensor.

In accordance with another aspect, there is provided a system for treatment of cells with activation particles. The system may comprise a treatment device comprising an elongated housing having a luminal inlet on a first end, a luminal outlet on a second end, and a housing inlet and a housing outlet, and at least one hollow fiber semi-permeable membrane positioned within the elongated housing extending between the luminal inlet and the luminal outlet to define an interior flow chamber and an exterior flow chamber, the hollow fiber semi-permeable membrane having a plurality of pores dimensioned to prevent passage of cells to be treated and the particles, the activation particles being bound to a surface of the hollow fiber semi-permeable membrane. the system may comprise a source of a biosample comprising the cells to be treated fluidly connected to the luminal inlet. The system may comprise at least one source of a media fluid independently fluidly connected to one of the luminal inlet and the luminal outlet, and one of the housing inlet and the housing outlet.

In accordance with another aspect, there is provided a cell processing system comprising a transduction device. The transduction device may comprise an elongated housing having a luminal inlet on a first end, a luminal outlet on a second end, and a housing inlet and a housing outlet. The transduction device may comprise at least one hollow fiber semi-permeable membrane positioned within the elongated housing extending between the luminal inlet and the luminal outlet to define an interior flow chamber and an exterior flow chamber, the hollow fiber semi-permeable membrane having a plurality of pores dimensioned to prevent passage of cells to be transduced and viral particles and allow passage of inhibitory factors. The luminal inlet may be constructed and arranged to receive the cells to be transduced and the viral particles. The system may comprise a separation device. The separation device may comprise a housing having an inlet fluidly connectable to the luminal outlet of the transduction device, a first outlet, and a second outlet. The separation device may comprise a semi-permeable membrane positioned within the housing to define a first flow chamber between the inlet and the first outlet and a second flow chamber opposite the first flow chamber fluidly connected to the second outlet, the semi-permeable membrane having a plurality of pores dimensioned to allow passage of the particles and prevent passage of transduced cells.

In some embodiments, the semi-permeable membrane of the separation device is a hollow fiber membrane.

In some embodiments, the semi-permeable membrane of the separation device has an average pore size of between about 50% and about 5% of the average diameter of the transduced cells.

In some embodiments, the semi-permeable membrane of the separation device has an average pore size of between about 200 nm and 5 μm.

In some embodiments, the luminal inlet of the transduction device is connectable to an intraluminal line in fluid communication with a donor subject.

In some embodiments, the system further comprises a target cell separation device having an inlet fluidly connectable to the intraluminal line and a first outlet fluidly connectable to deliver target cells to the luminal inlet of the transduction device as the cells to be transduced.

In some embodiments, the target cell separation device comprises a housing and a semi-permeable membrane positioned within the housing to define a first flow chamber between the inlet and the first outlet and a second flow chamber opposite the first flow chamber fluidly connected to a second outlet, the semi-permeable membrane having surface-bound antibodies configured to bind the target cells and leave non-target cells unbound.

In some embodiments, the first outlet is connectable to an intraluminal line in fluid communication with a recipient subject.

In some embodiments, the system further comprises a quality control device positioned upstream from the intraluminal line.

In some embodiments, the system further comprises an activation device. The activation device may comprise an elongated housing having a luminal inlet on a first end, a luminal outlet on a second end, and a housing inlet and a housing outlet. The activation device may comprise at least one hollow fiber semi-permeable membrane positioned within the elongated housing extending between the luminal inlet and the luminal outlet to define an interior flow chamber and an exterior flow chamber, the hollow fiber semi-permeable membrane having a plurality of pores dimensioned to prevent passage of cells to be activated. The luminal inlet may be constructed and arranged to receive the cells to be activated. In some embodiments, at least one of the luminal inlet of the activation device and the luminal outlet of the activation device may be fluidly connectable to deliver activated cells to the luminal inlet of the transduction device as the cells to be transduced.

In some embodiments, the system comprises activation particles bound to a surface of the hollow fiber semi-permeable membrane.

In some embodiments, the luminal inlet is constructed and arranged to receive activation particles, and the plurality of pores are dimensioned to prevent passage of the activation particles and allow passage of inhibitory factors.

In some embodiments, the luminal inlet of the activation device is fluidly connectable to an intraluminal line in fluid communication with a donor subject.

In some embodiments, the system further comprises an expansion device. The expansion device may have a first inlet fluidly connectable to the luminal outlet of the treatment device, a second inlet fluidly connectable to a source of an oxygen containing gas, and a first outlet fluidly connectable to the inlet of the separation device.

In some embodiments, the expansion device comprises a housing having the first inlet, the second inlet, the first outlet, and a second outlet. The expansion device may comprise a semi-permeable membrane positioned within the housing to define a first flow chamber between the inlet and the first outlet and a second flow chamber opposite the first flow chamber fluidly connected to the second outlet, the semi-permeable membrane having a plurality of pores dimensioned to prevent passage of the transduced cells.

In some embodiments, the semi-permeable membrane of the expansion device is a hollow fiber membrane.

In accordance with another aspect, there is provided a method of transducing cells with viral particles. The method may comprise introducing a biosample comprising the cells to be transduced and a treatment agent comprising the viral particles into a first inlet of a treatment device against a lumen side of a hollow fiber semi-permeable membrane having a plurality of pores dimensioned to prevent passage of the cells to be transduced and the viral particles at a flow rate effective to control a wall shear stress on the lumen side of the hollow fiber semi-permeable membrane. The method may comprise maintaining the cells to be transduced in contact with the viral particles on the lumen side of the hollow fiber semi-permeable membrane for an amount of time effective to produce transduced cells in an intermediate sample. The method may comprise introducing a first media fluid to suspend the transduced cells in an intermediate sample into one of the first inlet and a first outlet of the treatment device along the lumen side of the hollow fiber semi-permeable membrane at a flow rate effective to control the wall shear stress on the lumen side of the hollow fiber semi-permeable membrane. The method may comprise introducing a second media fluid to release the transduced cells from the lumen side of the hollow fiber semi-permeable membrane into one of a second inlet and a second outlet of the treatment device against a surface side of the hollow fiber semi-permeable membrane at a flow rate effective to control the wall shear stress on the lumen side of the hollow fiber semi-permeable membrane, the first media fluid and the second media fluid configured to produce a treated cell sample. The method may comprise discharging the treated cell sample through the first outlet of the treatment device.

In some embodiments, the method may comprise introducing at least a portion of the first media fluid and introducing at least a portion of the second media fluid substantially simultaneously.

In some embodiments, the first media fluid and the second media fluid are obtained from the same source of a media fluid.

In some embodiments, the first media fluid and the second media fluid are each obtained from different sources of media fluid.

In some embodiments, the method may further comprise introducing a third media fluid to co-localize the cells to be transduced and the viral particles on the lumen side of the hollow fiber semi-permeable membrane into the first inlet of the treatment device against the lumen side of the hollow fiber semi-permeable membrane.

In some embodiments, two or more of the first media fluid, the second media fluid, and the third media fluid are obtained from the same source of a media fluid.

In some embodiments, the method may further comprise introducing a priming fluid into at least one of the first inlet of the treatment device and the second inlet of the treatment device prior to introducing the biosample and the treatment agent to substantially remove air bubbles from within the treatment device.

In some embodiments, the treatment device is positioned in an upright orientation. The method may further comprise introducing the biosample and the treatment agent against a direction of gravity.

In some embodiments, the method may further comprise separating the transduced cells in the treated cell sample from the viral particles in the treated cell sample.

In some embodiments, the amount of time effective to produce the transduced cells is between about 60 minutes to 360 minutes.

In some embodiments, the method may comprise combining the biosample and the treatment agent to produce a mixed sample comprising the cells to be transduced and the viral particles and introducing the mixed sample into the first inlet of the treatment device.

In some embodiments, the mixed sample is substantially homogeneous.

In some embodiments, the method may comprise introducing the biosample comprising the cells to be transduced before introducing the treatment agent comprising the viral particles.

In some embodiments, the method may comprise introducing the treatment agent comprising the viral particles before introducing the biosample comprising the cells to be transduced.

In some embodiments, the method may further comprise removing at least some media of the intermediate sample from the treatment device and introducing a fifth media fluid comprising nutrients into the treatment device before introducing the first media fluid and the second media fluid.

In some embodiments, the method may further comprise introducing an oxygen containing gas into the treatment device.

In some embodiments, the method may further comprise introducing a gas into the treatment device substantially simultaneously with at least one of the first media fluid and the second media fluid.

In some embodiments, the method may further comprise introducing a second amount of the treatment agent comprising a second amount of the viral particles into the first inlet of the treatment device.

In some embodiments, the method may further comprise introducing a second treatment agent comprising a second type of viral particles into the first inlet of the treatment device.

In some embodiments, the method may further comprise introducing an activation agent comprising activation particles into the first inlet of the treatment device against the lumen side of the hollow fiber semi-permeable membrane.

In some embodiments, the method may further comprise measuring pressure within the treatment device.

In some embodiments, the method may further comprise controlling a rate of introducing at least one of the biosample, the treatment agent, the first media fluid, and the second media fluid responsive to the measurement of pressure.

In some embodiments, the method may comprise controlling the flow rate of introducing at least one of the biosample and the treatment agent to control the wall shear stress on the lumen side of the hollow fiber semi-permeable membrane to be between about 0.05 Pa and 1.0 Pa.

In some embodiments, the method may comprise controlling the flow rate of introducing at least one of the first media fluid and the second media fluid to control the wall shear stress on the lumen side of the hollow fiber semi-permeable membrane to be between about 1.0 Pa and 10 Pa.

In some embodiments, the method may comprise introducing the biosample containing 2 million cells to 500 million cells.

In some embodiments, the method may comprise introducing the biosample containing 500 million cells to 1 billion cells.

In some embodiments, the flow rate of at least one of the biosample and the treatment agent is between about 0.025 $ml/min/cm^2$ and about 1 $ml/min/cm^2$ surface area of the hollow fiber semi-permeable membrane In some embodiments, the method may comprise least one of introducing the first media fluid at a flow rate of between about 1.0 ml/min/$cm^2$ and about 2.5 ml/min/$cm^2$ surface area of the hollow fiber semi-permeable membrane, and introducing the second media fluid at a flow rate of between about 0.05 ml/min/$cm^2$ and about 2.0 ml/min/$cm^2$ surface area of the hollow fiber semi-permeable membrane.

In accordance with another aspect, there is provided a method of activating cells with activation particles. The method may comprise introducing a biosample comprising the cells to be activated into a first inlet of a treatment device against a lumen side of a hollow fiber semi-permeable membrane having a plurality of pores dimensioned to prevent passage of the cells to be activated at a flow rate effective to control a loading wall shear stress on the lumen side of the hollow fiber semi-permeable membrane. The method may comprise maintaining the cells to be activated in contact with the activation particles on the lumen side of the hollow fiber semi-permeable membrane for an amount of time effective to produce activated cells in an intermediate sample. The method may comprise introducing a first media fluid to suspend the activated cells in an intermediate sample into one of the first inlet and a first outlet of the treatment device along the lumen side of the hollow fiber semi-permeable membrane at a flow rate effective to control the wall shear stress on the lumen side of the hollow fiber semi-permeable membrane. The method may comprise introducing a second media fluid to release the activated cells from a lumen side of the hollow fiber semi-permeable membrane into one of a second inlet and a second outlet of the treatment device against a surface side of the hollow fiber semi-permeable membrane at a flow rate effective to control the wall shear stress on the lumen side of the hollow fiber semi-permeable membrane, the first media fluid and the second media fluid configured to produce a treated cell sample. The method may comprise discharging the treated cell sample through the first outlet of the treatment device.

In some embodiments, the activation particles are bound to the lumen side of the hollow fiber semi-permeable membrane.

In some embodiments, the activation particles comprise an antibody or an antigen bound to the lumen side of the hollow fiber semi-permeable membrane.

In some embodiments, the plurality of pores are dimensioned to prevent passage of the activation particles. The method may further include introducing the activation particles into the first inlet of the treatment device against the lumen side of the hollow fiber semi-permeable membrane.

In some embodiments, the method may comprise combining the biosample comprising the cells to be activated and the activation particles to produce a mixed sample and introducing the mixed sample into the first inlet of the treatment device.

In some embodiments, the mixed sample is substantially homogeneous.

In some embodiments, the method may comprise introducing the biosample comprising the cells to be activated before introducing the activation particles.

In some embodiments, the method may comprise introducing the activation particles before introducing the biosample comprising the cells to be activated.

In some embodiments, the activation particles include an antigen or antibody coated on a bead.

In some embodiments, the treatment device is positioned in an upright orientation. The method may comprise introducing the biosample and the activation particles against a direction of gravity.

In some embodiments, the method may further comprise separating the activated cells in the treated cell sample from the activation particles in the treated cell sample.

In some embodiments, the method may comprise introducing at least a portion of the first media fluid and introducing at least a portion of the second media fluid substantially simultaneously.

In some embodiments, the first media fluid and the second media fluid are obtained from the same source of a media fluid.

In some embodiments, the first media fluid and the second media fluid are each obtained from different sources of media fluid.

In some embodiments, the method may further comprise introducing a third media fluid to co-localize the cells to be activated on the lumen side of the hollow fiber semi-permeable membrane into the first inlet of the treatment device against the lumen side of the hollow fiber semi-permeable membrane.

In some embodiments, two or more of the first media fluid, the second media fluid, and the third media fluid are obtained from the same source of a media fluid.

In some embodiments, the method may further comprise introducing a priming fluid into at least one of the first inlet of the treatment device and the second inlet of the treatment device prior to introducing the biosample and the treatment agent to substantially remove air bubbles from within the treatment device.

In some embodiments, the method may further comprise introducing a transduction agent comprising viral particles into the first inlet of the treatment device against the lumen side of the hollow fiber semi-permeable.

In accordance with another aspect, there is provided a device dimensioned for treatment of a target number of cells with particles. The device may comprise an elongated housing having a luminal inlet on a first end, a luminal outlet on a second end, and a housing inlet and a housing outlet. The device may comprise at least one primed hollow fiber semi-permeable membrane positioned within the elongated housing extending between the luminal inlet and the luminal outlet to define an interior flow chamber and an exterior flow chamber. In some embodiments, the luminal inlet is constructed and arranged to receive the cells to be treated and the particles. In some embodiments, the at least one hollow fiber semi-permeable membrane has a plurality of pores dimensioned to prevent passage of the cells to be treated and the particles and allow passage of inhibitory factors, and an interior surface area of between about 20 $mm^2$ and about 250 $mm^2$ for every 1 million cells to be treated.

In some embodiments, the membrane has a membrane thickness of between about 50 μm and about 250 μm.

In some embodiments, the device further comprises a priming fluid within the elongated housing substantially free of air bubbles.

In some embodiments, the target number of cells is selected from about 2 million to about 500 million.

In some embodiments, the target number of cells is selected from about 500 million to about 1 billion.

In some embodiments, the plurality of pores have an average pore size of between about 300 kD and about 750 kD.

In some embodiments, the housing has a tubular structure.

In some embodiments, housing inlet and the housing outlet are positioned on a lateral surface of the housing.

In some embodiments, the housing inlet and the housing outlet are each positioned on one of the first end and the second end of the housing.

In some embodiments, the device further comprises a substrate material having a lower hydraulic resistance than the at least one hollow fiber semi-permeable membrane, the substrate material constructed and arranged to give structural support to the at least one hollow fiber semi-permeable membrane.

In some embodiments, the interior flow chamber of each hollow fiber semi-permeable membrane has a volume of between about 20 μL and about 360 μL.

In some embodiments, each hollow fiber semi-permeable membrane has a length of between about 2 cm and about 100 cm.

In some embodiments, the device has a plurality of hollow fiber semi-permeable membranes arranged in a bundle, the device comprising an inlet manifold fluidly connecting the luminal inlet with an inlet of each hollow fiber semi-permeable membrane and an outlet manifold fluidly connecting an outlet of each hollow fiber semi-permeable membrane with the luminal outlet.

In some embodiments, the device further comprises a support material having a lower hydraulic resistance than the at least one hollow fiber semi-permeable membrane, the support material constructed and arranged to give structural support to the bundle of hollow fiber semi-permeable membranes.

In some embodiments, the plurality of hollow fiber semi-permeable membranes collectively have an interior flow chamber volume of between about 20 μL and about 7.2 mL.

In some embodiments, the interior surface area of the at least one hollow fiber semi-permeable membrane is between about 0.2 $mm^2$ and about 4 $mm^2$ for every 1 $mm^3$ volume of the housing.

In some embodiments, the device may have a 50%-80% packing ratio of hollow fiber semi-permeable membranes within the housing.

In some embodiments, a cross section of the interior flow chamber of the at least one hollow fiber semi-permeable membrane has a diameter of between about 0.25 mm and about 1.00 mm.

In some embodiments, the at least one hollow fiber semi-permeable membrane comprises at least one of polyvinylidene fluoride (PVDF), polycarbonate (PC), nylon, polypropylene, polyethersulfone (PES), polysulfone (PS), track-etched polycarbonate (PCTE), mixed cellulose ester, and nitrocellulose.

In some embodiments, the at least one hollow fiber semi-permeable membrane comprises PES modified to include hydrophilic surface functional groups.

In some embodiments, the device is sterilizable by gamma irradiation or ethylene oxide.

In some embodiments, the device is a multi-use device.

In some embodiments, the device is a single-use device.

In accordance with another aspect, there is provided a device dimensioned for treatment of a target number of cells with activation particles. The device may comprise an elongated housing having a luminal inlet on a first end, a luminal outlet on a second end, and a housing inlet and a housing outlet. The device may comprise at least one primed hollow fiber semi-permeable membrane positioned within the elongated housing extending between the luminal inlet and the luminal outlet to define an interior flow chamber and an exterior flow chamber. In some embodiments, the at least one hollow fiber semi-permeable membrane has a plurality of pores dimensioned to prevent passage of the cells to be treated and an interior surface area of between about 20 $mm^2$ and about 250 $mm^2$ for every 1 million cells to be treated. In some embodiments, the activation particles are bound to a lumen side of the hollow fiber semi-permeable membrane.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
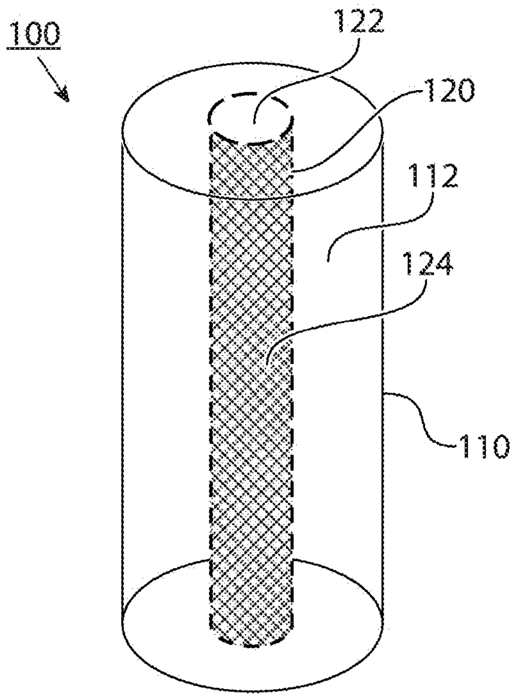
FIG. 1 is a perspective view of a portion of a device for treatment of cells, according to one embodiment.

The disclosure relates to devices for localizing cells on a membrane surface and systems and methods for the treatment of cells on the membrane. In general, the devices, systems, and methods disclosed herein utilize semi-permeable membranes in a cylindrical configuration, referred to herein as hollow fiber semi-permeable membranes, having a plurality of pores dimensioned to prevent passage of the cells to localize the cells during treatment. The cylindrical configuration of the hollow fiber semi-permeable membrane may increase surface area for localization and treatment of the cells, while accommodating a variety of flow schemes for fluids through and along the membrane.

The devices, systems, and methods disclosed herein may be used for any treatment of cells. Transduction and activation are two exemplary treatments described herein, which include co-localization of the cells with particles for treatment. The cells may be subpopulations of immune cells. The particles may be viral particles with the ability to introduce genetic modification to the cells or coated nano- or microparticles that may be used to illicit change in the cells through cell signaling pathways. The viral particles may be purified or unpurified lentivirus, retrovirus, or adeno-associated viral constructs.

Gene therapy is the approach of introducing genetic material into living cells, often times with the end goal of curing disease. In accordance with one aspect, there is provided a tool for supporting ex vivo transfer of genetic material into cells, where cells are taken from the body, modified, and infused into the patient as a therapeutic product. According to one embodiment, the devices and methods disclosed herein form a system and method for gene therapy. The gene therapy may include steps such as extraction of cells from a subject, selection and activation of desired cells, gene transfer, cell expansion, and infusion of modified cells into a subject. The devices, systems, and methods disclosed herein may be used for activation of desired cells, gene transfer or transduction of cells, washing or reperfusion of cells, expansion of cells, separation and/or selection of modified cells for infusion, or separation of desired subpopulations of cells.

The systems and methods disclosed herein may be associated with gene transfer. For instance, the systems and methods disclosed herein may be associated with lentiviral vector or adenoviral vector gene transfer. Gene transfer may be effectuated by transport, for example, using convective transport to deliver genetic information to cells. Gene transfer may be effectuated by co-localization, for example, by co-concentrating genetic information and cells in a chamber. In accordance with certain embodiments disclosed herein, gene transfer is effectuated by combining convective transport and co-localization methods. In some embodiments, the devices and methods disclosed herein may optimize kinetics of interaction for transduction of cells by concentrating cells and virus, while replenishing nutrients to the cells and limiting the waste of viral particles. The devices and methods disclosed herein may concentrate cells and virus, while removing competing moieties, also referred to as "inhibitory factors" herein, to improve effective cell and virus interactions. Inhibitory factors may also refer to moieties that compete with activation particles. The devices and methods disclosed herein may enhance transduction through other methods, such as effectuating change to the cells by modifying pH or osmolarity experienced by the cells, thereby making the cells more amenable to transduction.

Current methods for transduction of cells do not efficiently utilize the virus that introduces genetic information to the cells. The main method used for transduction of primary cells is the static combination of viral and cell laden fluids. When the viral particles and cells spatially contact one another, there is a chance that the virus binds to the cell and goes on to infect the cell leading to gene transfer from the virus to the cell. In static cell culture, this spatial interaction between cells and virus relies on Brownian motion. This Brownian diffusion of particles is a random process and takes hours for virus and cells to sample a large enough volume leading to a binding interaction between cells and virus. Viral particles used for gene transfer to cells, however, have a finite lifetime. Many viral particles decay through natural processes before they are able to interact with and infect a cell. Because these viral particles are extremely expensive to manufacture, there exists a need to increase the efficient use of virus in gene transfer.

In many conventional applications, the viral particle pseudotype and methods of manufacturing the viral particles may produce a viral sample that results in significant inefficiencies in the transduction process. The phenomenon may be, in part, attributed to impurities secreted by the virus producer cell lines or “inhibitory factors” that competitively bind the receptors on the host cells, reducing the number of available interaction sites between the cells and the viral particles. Conventionally, chemical enhancers are often employed to achieve meaningful levels of transduction. However, such chemical enhancers are typically costly and/or detrimental to the health of cells being processed. The devices described herein may achieve a significant enhancement in transduction efficiency by removing inhibitory factors, without use of chemical enhancers, when compared to controls.

The systems and methods may be used to sequentially deliver viral particles followed by cells. This method may be used to purify the viral stock, reducing inhibitory factors in the viral stock. Alternatively, the systems and methods may be used to deliver a mixed sample of cells and virus, or cells followed by viral particles. The selected pore size of the membrane may provide filtration of the inhibitory factors from the viral stock or mixed sample, leading to higher transduction efficiencies achieved in the system. For instance, the membrane may be selected to allow passage of secreted inhibitory factors and retain viral particles and cells. It should be noted that inhibitory factors may also refer to impurities that reduce the number of available interaction sites for activation particles.

Furthermore, in certain embodiments, soluble or membrane surface-bound transduction enhancers may be used to improve transduction efficiency. For instance, compounds such as fragments of recombinant human fibronectin (rFN-CH-296) may be bound to the surface of the membrane, bringing cells and viral particles into contact with the enhancer-coated membrane surface. Additionally, the media may comprise cationic polymer soluble enhancers, such as polybrene or protamine sulfate, to enhance transduction efficiency. Additionally, a buffer with a different tonicity or pH than the media may be introduced as a transduction enhancer. Such methods may be employed to improve transduction efficiency without addition of chemical enhancers.

The devices disclosed herein use convective transport to deterministically transport target particles and agents into a confined area. For instance, the device and methods disclosed herein transport cells and virus into a confined area in order to increase the probability that a virus will interact with a cell before it naturally decays. The device employs one or more flow channels to direct a cell and viral laden fluid onto a semi-permeable membrane through convective transport.

Devices and methods disclosed herein may be agnostic to cell type and viral vector. In some embodiments, devices and methods may be used to transduce a wide variety of cell types, including but not limited to, stem cells, immune cells, cancer cells, engineered cells, primary cells, T-cells, primary T-cells, regulatory T-cells, NK cells, B cells, and hematopoietic stem cells (HSC). In some embodiments, devices and methods disclosed herein may be configured to operate with lentiviral vectors (LVV), retroviral vectors, or adeno-associated viral vectors (AAV). In some embodiments, devices and methods disclosed herein may be configured to operate with viral particles having a diameter of less than about 100 nm or of about 10-30 nm.

As disclosed herein, there is provided a device for treatment of cells with particles. The device may comprise an elongated housing having a plurality of inlets and outlets. The housing may have a luminal inlet on a first end and a luminal outlet on a second end. The housing may also have a housing inlet and a housing outlet. The housing inlet and the housing outlet may be positioned on any surface of the housing. For example, the housing inlet and the housing outlet may each be independently positioned on the first end, the second end, or a lateral surface of the housing. In certain embodiments, the housing inlet and the housing outlet may be positioned on the lateral surface of the housing. The housing inlet and the housing outlet may extend in the same direction, in different directions, or in opposite directions on the lateral surface of the housing.

In some embodiments, the housing may have a tubular structure. However, the housing may have any cross-sectional geometry.

In some embodiments, the device may comprise one or more recycle loops configured to direct recycle fluid back into the housing. For example, the device may comprise a luminal recycle loop extending between the luminal outlet and the luminal inlet. In some embodiments, the device may comprise a housing recycle loop extending between the housing outlet and the housing inlet.

The device may comprise at least one hollow fiber semi-permeable membrane positioned within the housing. The at least one hollow fiber semi-permeable membrane may comprise an inlet fluidly connected to the luminal inlet of the housing and an outlet fluidly connected to the luminal outlet of the housing. The at least one hollow fiber semi-permeable membrane may have a plurality of pores dimensioned to prevent passage of the cells. In some embodiments, the plurality of pores may be dimensioned to prevent passage of the particles, for example, viral particles or activation particles. In other embodiments, the plurality of pores may be dimensioned to allow passage of the particles, for example, viral particles or activation particles. In some embodiments, the plurality of pores may be dimensioned to allow passage of inhibitory factors.

The hollow fiber semi-permeable membrane positioned within the housing may define an interior flow chamber and an exterior flow chamber. The interior flow chamber of the hollow fiber semi-permeable membrane may be fluidly connected to the luminal inlet and luminal outlet of the housing. Fluid containing cells and/or particles may be introduced into the interior flow chamber through the luminal inlet of the housing. Thus, the luminal inlet may be constructed and arranged to receive cells to be treated and particles. In some embodiments, a co-localizing fluid may be introduced into the interior flow chamber through the luminal inlet. The exterior flow chamber may be defined by an exterior surface of the hollow fiber semi-permeable membrane and an interior cavity of the housing. The exterior flow chamber may be fluidly connected to the housing inlet and housing outlet. In some embodiments, a co-localizing fluid may be introduced into the exterior flow chamber through the housing inlet.

The device may be dimensioned for treatment of a target number of cells with particles. The housing and/or membrane may have dimensions selected for treatment of a target number of cells. For instance, the device may be dimensioned for treatment of 2 million-5 million cells, 5 million-10 million cells, 10 million-50 million cells, 50 million-100 million cells, 100 million-200 million cells, 200 million-500 million cells, 500 million-750 million cells, or 750 million-1 billion cells. In particular, the device, for example, the membrane may be dimensioned to provide an interior surface area of between about 20 $mm^2$ and about 250 $mm^2$ for every 1 million cells, for example, 20 $mm^2$-30 $mm^2$, 30

$mm^2$-50 $mm^2$, 50 $mm^2$-100 $mm^2$, 100 $mm^2$-150 $mm^2$, 150 $mm^2$-200 $mm^2$, or 200 $mm^2$ —250 $mm^2$ for every 1 million cells.

Generally, the semi-permeable membrane allows fluid to pass through but captures or mechanically entraps the cells and/or particles on the interior surface of the hollow fiber membrane. This entrapment spatially localizes the cells and/or particles across the interior surface of the membrane. In transduction, for example, the co-localization of the cells and particles greatly increases the probability of spatial interaction and binding between cells and virus. The localization across the surface within a chamber also reduces the diffusive transport length between cells and particles leading to enhanced diffusion-based transport interaction as well.

The semi-permeable membrane may have a plurality of pores dimensioned to allow passage of a fluid and prevent passage of the cells and the particles. The plurality of pores may be dimensioned to allow passage of inhibitory factors, such as impurities and products generated as a byproduct during the virus production process. The plurality of pores may be dimensioned to allow passage of waste, such as cell waste, for example, cell waste products formed as a byproduct of cellular respiration and/or metabolism. The semi-permeable membrane may have an average pore size smaller than the average diameter of the cells or particles, whichever is smaller. In some embodiments, the semi-permeable membrane may have an average pore size of between about 50% and about 5%, for example, between about 50% and about 25% or between about 25% and about 5% of the average diameter of the cells or particles, whichever is smaller. In transduction and activation applications, the viral particle or activation particle is generally smaller than the cell to be treated. Thus, in some embodiments, the semi-permeable membrane may have an average pore size of between about 50% and about 5% of the average diameter of the particles.

The pore diameter may be selected or configured to allow or prevent passage of a desired viral particle. For instance, the pore diameter may be selected or configured to allow or prevent passage of a viral particle having a diameter of about 100 nm (for example, LVV) or a viral particle having a diameter of about 20 nm (for example, AAV). In transduction with LVV, for example, the viral particle may an average diameter of about 100 nm. Such a membrane may have a pore size of about 80 nm, about 50 nm, about 30 nm, about 25 nm, or about 5 nm. In transduction with AAV, for example, the viral particle may an average diameter of about 20 nm. Such a membrane may have a pore size of about 15 nm, about 10 nm, about 5 nm, or about 1 nm. In general, the semi-permeable membrane has a pore diameter of between about 1 nm and about 100 nm, for example, between about 1 nm and about 30 nm. The semi-permeable membrane may have an average pore diameter of about 50 nm or less, 40 nm or less, 30 nm or less, 20 nm or less, 10 nm or less, or 5 nm or less. In other embodiments, the semi-permeable membrane may have a pore diameter selected or configured to allow or prevent passage of a particle having a diameter of about 30 nm. The semi-permeable membrane may have a pore diameter selected or configured to allow or prevent passage of a particle having a diameter of about 10 nm.

The hollow fiber semi-permeable membrane may have an average pore size of between about 1 kD and about 750 kD, for example, between about 300 kD and about 750 kD or between about 300 kD and about 500 kD. The hollow fiber semi-permeable membrane may have an average pore size of about 1 kD, 3 kD, 5 kD, 10 kD, 30 kD, 50 kD, 70 kD, 100 kD, 300 kD, 500 kD, and 750 kD. In some embodiments, the membrane may be selected to have an average pore size dimensioned to prevent passage of cells and particles, and allow passage of inhibitory factors. It is believed that an average pore size between about 300 kD and about 750 kD may allow passage of inhibitory factors and prevent passage of particles, such as viral particles. Average pore sizes below about 300 kD are believed to prevent passage of a significant amount of inhibitory factors, which reduces transduction efficiency within the device as previously described.

Figure 2:
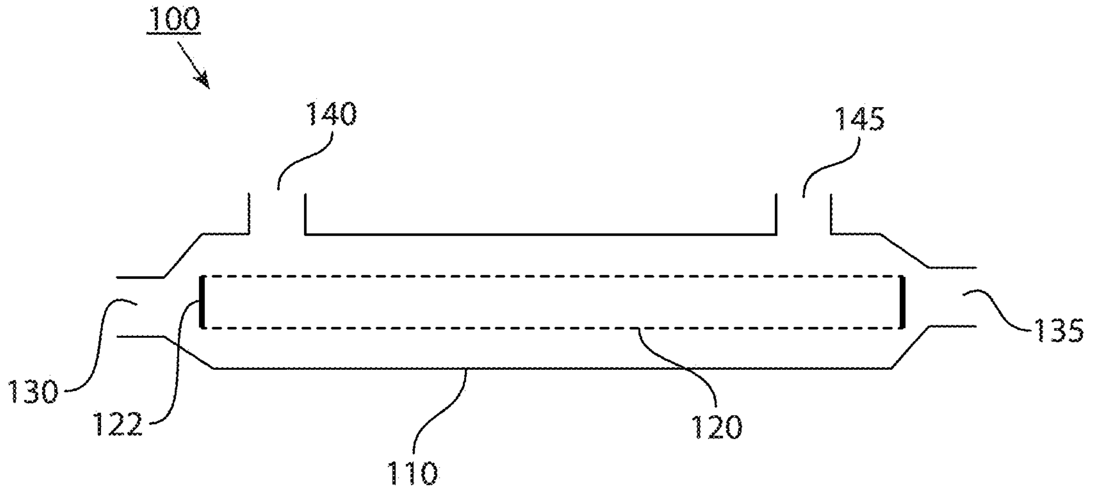
FIG. 2 is a side view of a portion of a device for treatment of cells, according to one embodiment.
Figure 3:
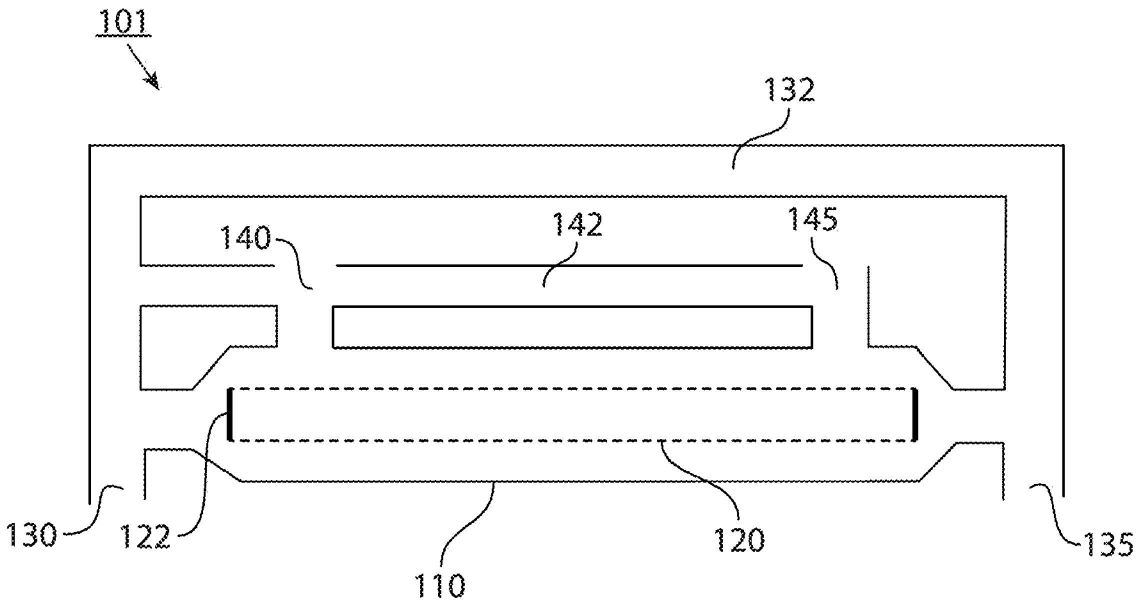
FIG. 3 is a side view of a portion of a device for treatment of cells, according to one embodiment.

FIG. 1 is a perspective view of a portion of a device 100 for treatment of cells, according to one embodiment. The portion of device 100 includes housing 110 and hollow fiber membrane 120 defining interior flow chamber 122 and exterior flow chamber 112. In the exemplary embodiment of FIG. 1, substrate material 124 is positioned on an exterior surface of hollow fiber membrane 120. FIG. 2 is a side view of a device 100 for treatment of cells, according to one embodiment. Device 100, as shown in FIG. 2, includes luminal inlet 130, luminal outlet 135, housing inlet 140, and housing outlet 145. FIG. 3 is a side view of device 101 including luminal recycle loop 132 and housing recycle loop 142, according to one embodiment. In some embodiments, as shown in FIG. 2, housing recycle loop 142 may extend from the housing outlet 140 and/or inlet 145 to the luminal inlet 135.

In some embodiments, the device may comprise more than one hollow fiber semi-permeable membrane. For example, the device may comprise 2 to 100 hollow fiber semi-permeable membranes or more. The capacity of the device is scalable by addition of hollow fiber semi-permeable membranes. In exemplary embodiments, the device may comprise 2 to 80 hollow fiber membranes, for example, 2 to 60 hollow fiber membranes, 2 to 40 hollow fiber membranes, 2 to 20 hollow fiber membranes, 2 to 10 hollow fiber membranes, 2 to 8 hollow fiber membranes, or 2 to 6 hollow fiber membranes.

The plurality of hollow fiber membranes may be arranged in a bundle. Specifically, the hollow fiber semi permeable membranes may extend along the length of the housing in a substantially parallel arrangement. Each hollow fiber semi-permeable membrane may be independently fluidly connected to the luminal inlet and the luminal outlet of the housing. The device may comprise an inlet manifold fluidly independently connecting the luminal inlet with the inlet of each hollow fiber semi-permeable membrane. The device may comprise an outlet manifold fluidly connecting the outlet of each hollow fiber semi-permeable membrane with the luminal outlet. In some embodiments, the manifold may be operated to selectively control the number of active hollow fiber membranes, accommodating a range of possible operating capacities.

Each hollow fiber semi-permeable membrane may define a corresponding interior flow chamber. The housing may define the exterior flow chamber between the interior surface of the housing and the exterior surface of each of the hollow fiber semi-permeable membranes.

Figure 4:
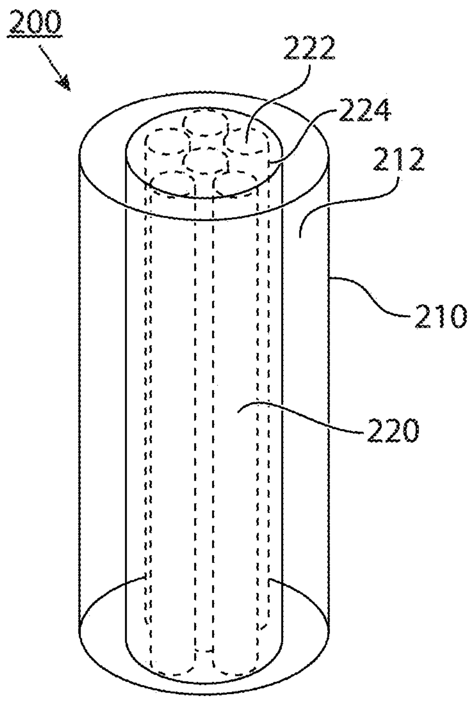
FIG. 4 is a perspective view of a portion of a device for treatment of cells, according to one embodiment.
Figure 5:
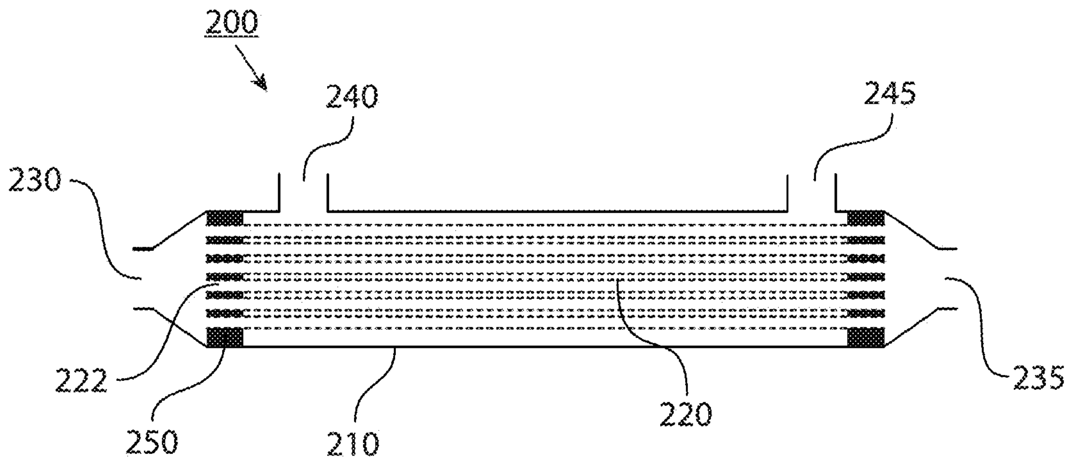
FIG. 5 is a side view of a portion of a device for treatment of cells, according to one embodiment.

FIG. 4 is a perspective view of a portion of a device 200 for treatment of cells, according to one embodiment. The portion of device 200 includes housing 210 and a plurality of hollow fiber membranes 220, each defining an interior flow chamber 222. The plurality of hollow fiber membranes 220 are arranged in a bundle. In the exemplary embodiment of FIG. 4, support material 224 is positioned to provide support to the bundle of hollow fiber membranes 220. The housing defines an exterior flow chamber 212. FIG. 5 is a side view of a device 200 for treatment of cells, according to one embodiment. Device 200, as shown in FIG. 5, includes luminal inlet 230, luminal outlet 235, housing inlet 240, housing outlet 245, and manifolds 250. Device 200 may include a luminal recycle loop and a housing recycle loop (as shown in FIG. 3).

In general, the device may be used for a number of functions that can be performed utilizing the different fluid inlets and outlets.

The device may be operated to accommodate a variety of flow schemes by controlling the open and closed states of the luminal and housing inlets and outlets and controlling the direction of flow through the inlets and outlets. For instance, the system or device may comprise one or more of a luminal inlet valve, a luminal outlet valve, a housing inlet valve, and a housing outlet valve, which can be actuated to control the direction of flow through the device and, in particular, across and/or against the membrane from the luminal side or from the surface side, as desired. In some embodiments, the valves are external to the fluid path of the device. External valves may control flow by pinching a flexible tubing.

Longitudinal luminal flow may be achieved by introducing fluid through the luminal inlet to the luminal outlet while closing the housing inlet and housing outlet. Such a flow scheme is also referred to herein as directing a fluid along the lumen side (internal) of the membrane. Longitudinal housing flow may be achieved by introducing fluid through the housing inlet to the housing outlet while closing the luminal inlet and luminal outlet. Such a flow scheme is also referred to herein as directing a fluid along a surface side (external) of the membrane. Luminal transmembrane flow may be achieved by introducing the fluid through the luminal inlet to one or both of the housing inlet and housing outlet and closing the luminal outlet. Such a flow scheme is also referred to herein as directing a fluid against the lumen side of the membrane. Reverse transmembrane flow may be achieved by introducing the fluid through the housing inlet to one or both of the luminal inlet and the luminal outlet and closing the housing outlet. Such a flow scheme is also referred to herein as directing a fluid against the surface side of the membrane. Other flow schemes may be accommodated.

Figure 6A:
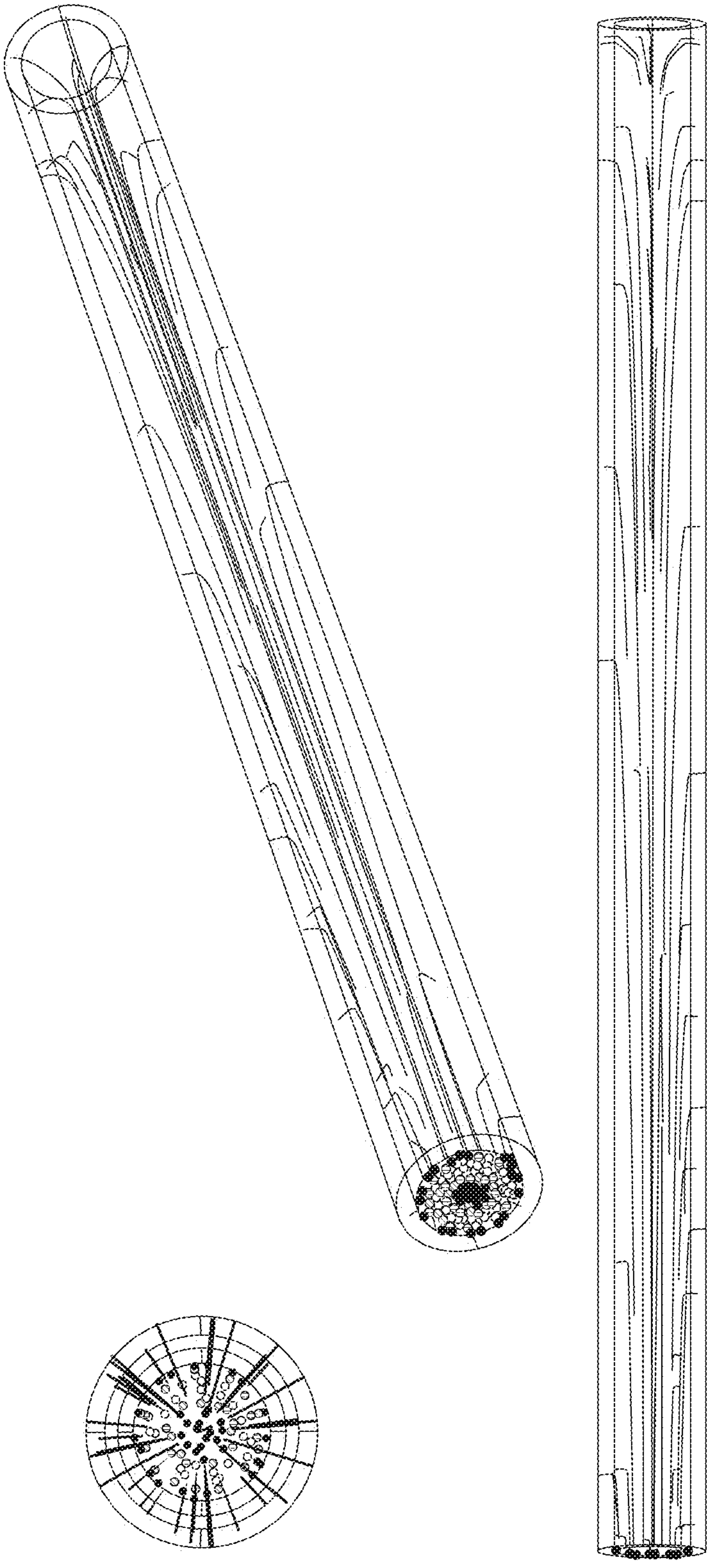
FIG. 6A includes front, perspective, and side views of a device for treatment of cells showing cell and particle trajectories during delivery into the device, according to one embodiment.

The device may be loaded with cells by introducing a biosample into the luminal inlet to produce a luminal transmembrane flow. The device may be loaded with particles simultaneously or sequentially with the cells. The suspended cells and/or particles may generally follow the flow streamlines and distribute onto the membrane. As the cells and/or particles cover the internal membrane surface, the cells and/or particles locally obstruct the flow. The streamlines of the flow are generally redistributed to the unoccupied areas of the membrane with less fluidic resistance, resulting in uniform distribution of the cells and/or particles onto the internal membrane surface. Thus, the cells and/or particles may be introduced at a flow rate effective to substantially evenly distribute the cells and the particles on a lumen side of the hollow fiber membrane. FIG. 6A includes front, perspective, and side views of a device showing simulated cell and particle trajectories during delivery into the device.

Furthermore, the cells, optionally with the particles, may be introduced at a loading density effective to substantially evenly distribute the cells and the particles on the membrane. The loading density (number of cells and/or particles within a given surface area of the membrane) effective may generally be calculated by considering average diameter of the cells, average diameter of the particles (when not negligible as compared to the diameter of the cells), and surface area of the membrane. The loading density may be effective to distribute the cells as a monolayer on the surface of the membrane. The particles, being generally smaller than the cells, may occupy void space between the cells. The loading density may be effective to distribute the cells as a multilayer on the membrane. The particles may occupy void space between the cells and between layers of cells.

In accordance with certain embodiments, the cells, optionally with the particles, may be introduced at a loading density effective to substantially evenly distribute the cells as a monolayer on the hollow fiber membrane. FIG. 9B is a schematic diagram showing a cross-sectional view of a hollow fiber membrane 120 having a monolayer of cells 10 distributed on the lumen side of the membrane. The particles 20 occupy space between the cells 10. Distribution of the cells 10 as a monolayer on the membrane 120 is believed to allow for enhanced interaction between cells 10 and particles 20.

In accordance with other embodiments, the cells, optionally with the particles, may be introduced at a loading density effective to distribute the cells as a multilayer on the hollow fiber membrane. FIG. 9C is a schematic diagram showing a cross-sectional view of a hollow fiber membrane 120 having a multilayer of cells distributed on the lumen side of the membrane. The particles 20 occupy space between the cells 10 and between layers of cells. Distribution of the cells 10 as a multilayer on the membrane 120 is believed to allow for enhanced interaction between cells 10 and particles 20. Furthermore, while not wishing to be bound by theory, it is believed that that multilayer distribution of cells 10 may entrap particles 20 between cell layers and prevent diffusion away from inner cell layers. The entrapment may lead to enhanced transduction.

In some embodiments, the cells and/or particles may be co-localized on the membrane by introducing a co-localizing fluid into the luminal inlet to produce a luminal transmembrane flow against a lumen side of the membrane. The luminal transmembrane flow may be effective to substantially evenly distribute the cells and/or particles on the lumen side of the hollow fiber membrane surface. The luminal transmembrane flow may be effective to distribute the cells as a multilayer on the lumen side of the membrane surface and entrap particles within the multilayer. In some embodiments, the co-localizing fluid may be introduced substantially continuously during a transduction period of the cells.

Figure 6B:
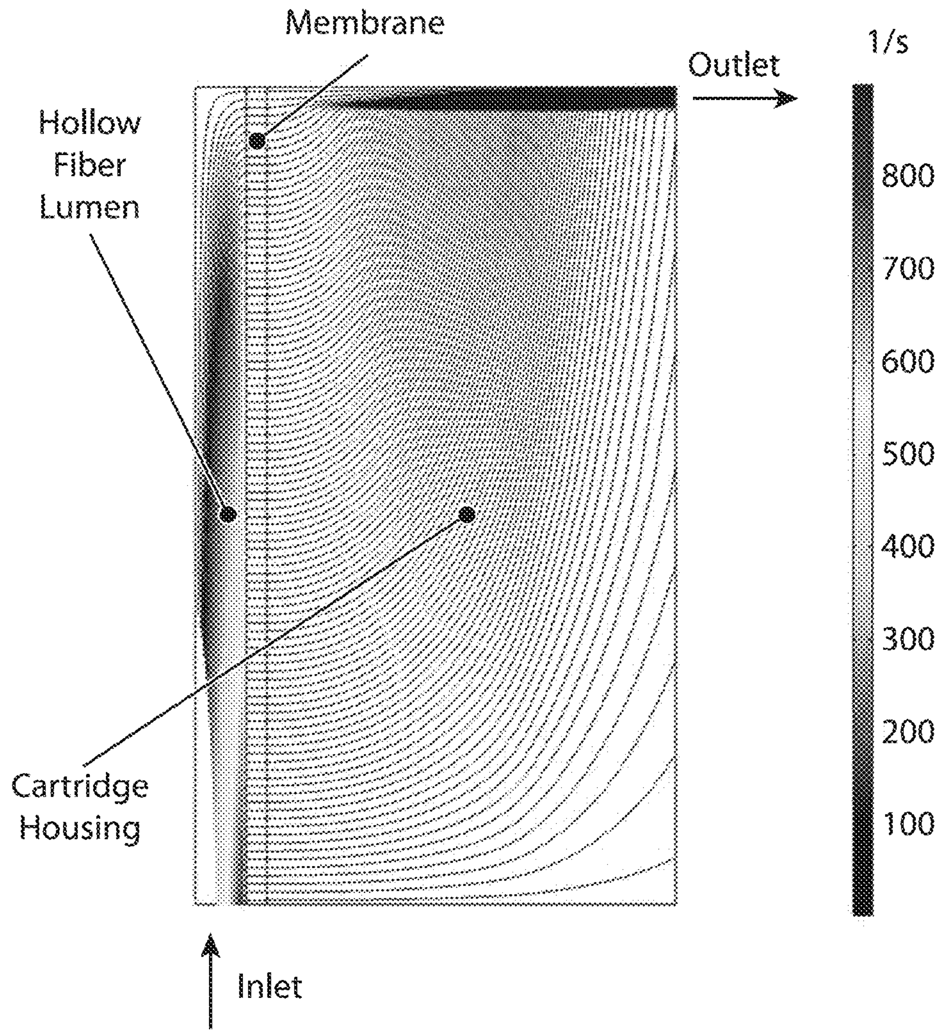
FIG. 6B is a cross-sectional view of a portion of a device for treatment of cells showing flow streamlines and shear stress experienced by cells and particles during co-localization on the membrane, according to one embodiment.

Distribution and co-localization of the cells and particles may generally result in increased local concentration of the interacting cells and particles, which is superior to passive interactions that are governed by diffusion. Furthermore, controlling the magnitude of luminal transmembrane flow may counteract diffusive forces, maintaining close contact between the cells and particles. FIG. 6B is a cross-sectional view of the device showing simulated flow streamlines and shear stress experienced by cells and particles during co-localization on the membrane.

For example, during transduction, co-localization of cell and virus against the membrane for a period of time is believed to produce increased cell transduction as compared to overnight non-device controls. In the exemplary embodiment of transduction of activated T cells with lentiviral particles, the device is believed to be capable of accommodating cells at different days post activation and maintain similar increased efficiency in transduction. Additionally, it is believed that increasing the interaction time for cells and virus in the device can further increase transduction efficiency using the device.

Figure 13A:
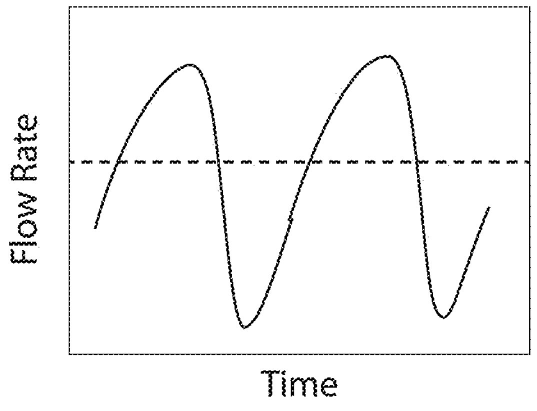
FIG. 13A is a graph showing flow rate over time for oscillatory flow.
Figure 13B:
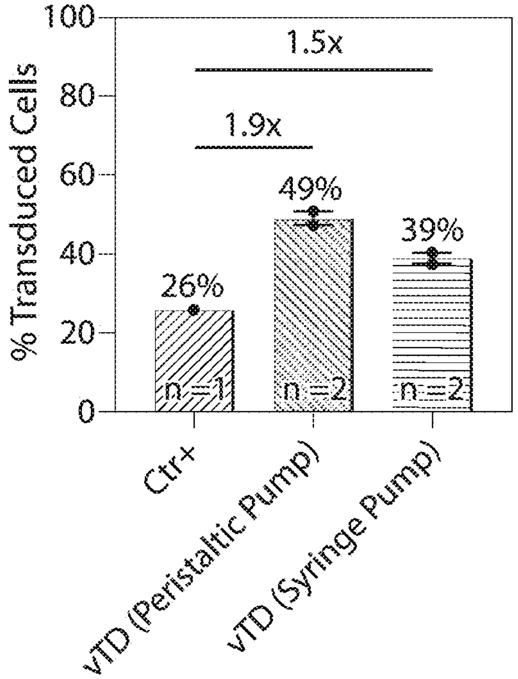
FIG. 13B is a graph showing percentage of transduced cells for a sample loaded and co-localized with an oscillatory flow as compared to a sample loaded and co-localized with a substantially steady flow, according to one embodiment.

In certain embodiments, the fluid flow properties during delivery and co-localization of the cells and particles may be substantially constant (steady) or varied (oscillatory). Oscillatory flow may be provided by varying flow rate of the fluid over time (FIG. 13A). In certain embodiments, oscillatory flow may be provided by one or more peristaltic pump fluidly connected to the media being provided with oscillatory flow. It has been shown that oscillatory flow results in higher transduction when compared to syringe pump driven flow (example 2; FIG. 13B). While not wishing to be bound by theory, it is believed that oscillatory flow may improve mixing and enhance interaction opportunities between the cells and particles. The enhanced interaction between cells and particles is believed to increase performance, for example, transduction efficiency, or reduce time required to achieve a desired modification of the cells.

The device may be unloaded by introducing a recovery fluid into the luminal inlet along a lumen side of the membrane to produce a longitudinal luminal flow and collecting the fluid with cells and/or particles through the luminal outlet. In some embodiments, the device may be unloaded in the reverse order, by passing fluid through the luminal outlet and collecting it as it flows out through the luminal inlet, producing a reverse longitudinal luminal flow along the lumen side of the membrane. During recovery, fluid passing along the lumen side of the membrane and lifts cells and particles off the membrane, suspending them in the fluid and carrying them out of the interior flow chamber though convective flow.

The housing inlets and outlets may be used to introduce fluid flow against a surface side of the membrane to assist with the removal of cells off the membrane surface. During unloading, the cells and/or particles may be released from the membrane surface by introducing a releasing fluid into the housing inlet against a surface side of the membrane to produce a reverse transmembrane flow. The reverse transmembrane flow may exit the luminal outlet or the luminal inlet and be collected with the recovery fluid.

In addition to loading and unloading, fluid that is passed across and against the surface side of the membrane and out the housing inlet or outlet can be recycled back into the housing with the use of a closed loop pumping system for recirculation of fluid. Fluid can also be cycled back and forth through the interior flow chamber with the use of a pumping system that pushes and pulls fluid across the membrane.

While treatment of the cells is generally performed on a lumen side of the membrane, it should be understood that treatment of the cells may be performed on a surface side of the hollow fiber membrane. In such embodiments, the methods may comprise loading cells and/or particles by introducing the biosample comprising cells and/or treatment agent comprising particles into the housing inlet of the device along a surface side of the membrane to produce a longitudinal housing flow. Cells and/or particles may be co-localized by introducing a co-localizing fluid into the housing inlet of the device to produce a reverse transmembrane flow against the surface side of the membrane. Cells and/or particles may be recovered by introducing a recovery fluid into the housing inlet or housing outlet of the device along the surface side of the membrane. Additionally, a releasing fluid may be introducing into the luminal inlet or luminal outlet of the device against the lumen side of the membrane to release the cells and/or particles from the membrane surface. Thus, the systems and methods disclosed herein may be operated to localize and/or treat cells on a surface side of the membrane.

In accordance with certain embodiments, the semi-permeable membrane may be primed. In some embodiments, a primed semi-permeable membrane may refer to a membrane that is free or substantially free of a protective coating. Protective coatings, such as glycerin coatings, are often applied to membranes for preservation of surface groups, such as hydrophilic or hydrophobic groups, during storage and/or shipping. In some embodiments, a primed semi-permeable membrane may be saturated or semi-saturated with a media fluid prior to contact with a biosample and/or treatment agent. In some embodiments, a priming fluid may be disposed within the housing. The priming fluid may render the device substantially free of air bubbles. The device comprising a primed semi-permeable membrane and a priming fluid may be activated for use.

The device may be primed by introducing a priming fluid into the luminal inlet along a lumen side of the membrane to produce a longitudinal luminal flow or against a lumen side of the membrane to produce transmembrane flow. In some embodiments, the device may be primed in the reverse order, by passing fluid through the luminal outlet and directing the fluid to the luminal inlet, producing a reverse longitudinal luminal flow along the lumen side of the membrane. In other embodiments, the device may be primed in a transmembrane flow by introducing the fluid through the luminal inlet and directing the fluid to a housing outlet against a lumen side of the membrane. In yet other embodiments, the device may be primed in a reverse transmembrane flow by introducing the fluid through a housing inlet and directing the fluid to a luminal outlet against a surface side of the membrane. In general, the device may be primed using any flow scheme that substantially fills the housing with the priming fluid, eliminating air bubbles.

The device may be used for transduction of cells with viral particles. Generally, the cells and viral particles can be introduced into the device. Fluid can be directed against a lumen side of the membrane during transduction to co-localize the cells and viral particles. Temperature of the device may be controlled during this period to provide temperature control of the reaction. Once transduction has occurred, the cells and viral particles can be suspended in a recovery fluid that enters the device through the luminal inlet or luminal outlet and carries the cells and viral particles out the opposite end. A releasing fluid may be introduced, optionally simultaneously with the recovery fluid, through the housing inlet or housing outlet to release the cells and viral particles from the membrane and improve recovery.

The device may be used for activation of cells. In some embodiments, the cells and activation particles, for example, antigens and/or antibodies, optionally coated on beads, can be introduced into the device. In other embodiments, the activation particles, for example, antigens and/or antibodies, are bound to a surface of the membrane. In such embodiments, the cells are introduced into the device to contact the membrane-bound activation particles. Fluid can be directed against a lumen side of the membrane during activation to co-localize the cells on the membrane, optionally to co-localize the activation particles. Temperature of the device may be controlled during this period to provide temperature control of the reaction. Once activation has occurred, the cells, and optionally the activation particles, can be suspended in a recovery fluid that enters the device through the luminal inlet or luminal outlet and carries the cells, and optionally the activation particles, out the opposite end. A releasing fluid may be introduced, optionally simultaneously with the recovery fluid, through the housing inlet or housing outlet to release the cells, and optionally the activation particles, from the membrane and improve recovery.

The device may also be used to change the media or fluid within the device, to provide nutrients and other factors to the cells and/or particles. Introducing a new fluid into the luminal inlet of the housing may lead to the displacement of the original suspension fluid through the housing outlet or luminal outlet, performing a media exchange. Gas and/or nutrient exchange may be performed as needed during treatment of the cells. In some embodiments, the media may be removed by vacuum before introducing a recovery and/or releasing fluid into the device for collection of the treated cells.

The device may be used for expansion of cells. In certain embodiments, the cells may be cultured on a surface of the membrane to allow cell expansion within the device. Media or fluid exchange may be performed as needed to maintain viability of the cells within the device. The media or fluid change may enable gas and/or nutrient exchange and clearing of waste matter within the device. For instance, the membrane may be configured to prevent passage of cells and allow passage of waste products.

The device may be used for separation of particles based on size. In certain embodiments, the device may be used for separation of cells from particles, for example, viral particles or activation particles. In other embodiments, the device may be used for separation of target cells from non-target cells. By using a semi-permeable membrane that passes particles with a particular size, a fluid passed against a lumen side of the membrane retains larger particles, such as cells, and passes smaller particles for separation. In some embodiments, the membrane may be coated with antibodies that bind the cells or target cells, to facilitate or improve separation, for example, through positive or negative selection. Particles that pass from the luminal inlet, through the membrane may be collected from the housing outlet, while particles, for example, cells, that do not pass through the membrane may be deposited on the lumen side of the membrane. The particles, for example, cells deposited on the lumen side of the membrane may be retrieved at a later time, following the unloading procedure described above.

Additionally, in some embodiments, the mixed cell sample may be directed from the luminal inlet to the luminal outlet. The coating on the membrane may be selected to strongly or weakly bind the target (positive selection) or non-target (negative selection) cells. Unbound cells may be directed to the luminal outlet and separated from membrane bound cells. Membrane bound cells may be retrieved at a later time.

In some embodiments, the target cells may be selected from stem cells, immune cells, cancer cells, engineered cells, primary cells, T-cells, primary T-cells, regulatory T-cells, NK cells, B cells, and hematopoietic stem cells (HSC). The target cells may be subclasses of cells, for example, subclasses of T-cells, such as CD3, CD4, CD8, or CD25 positive T-cells.

The semi-permeable membrane may comprise or be formed of a material selected to exhibit low protein binding characteristics. Membrane fouling may occur when protein is present in the fluid. The protein may build up on the membrane, increasing differential pressure with use over time. In general, smaller pore sizes exhibit more protein fouling.

An absolute luminal pressure greater than about 500 mmHg is generally undesirable. In particular, such a pressure drop may be undesirable for continued operation during a half-life of the viral particle. For instance, the membrane material may be selected to limit pressure drop to about 50 mmHg for flow of 6 hours (half-life of LVV) at a flowrate of 20 μl/min/cm$^2$. In some embodiments, the semi-permeable membrane may comprise a material selected to limit the membrane protein fouling rate to about 1.3 mmHg/min or less for a flowrate of up to 20 μl/min/cm$^2$. For example, the membrane material may be selected to limit the membrane protein fouling rate to about 1 mmHg/min, to about 0.5 mmHg/min, or to about 0.2 mmHg/min for a flowrate of up to 20 μl/min/cm$^2$. Similarly, the media and/or buffer may be selected to limit pressure drop, as previously described.

The semi-permeable membrane may comprise or be formed of polyvinylidene fluoride (PVDF), polycarbonate (PC), nylon, polypropylene, polyethersulfone (PES), polysulfone (PS), track-etched polycarbonate (PCTE), mixed cellulose ester, or nitrocellulose. The semi-permeable membrane may comprise or be formed of a hydrophilic material.

In some embodiments, the membrane may be modified to control interaction of the cells and/or particles with the membrane surface (for example, increase retention of cells or particles and/or reduce fouling). For example, charge, surface energy, hydrophilicity and/or hydrophobicity of the membrane may be selected. In certain embodiments, the membrane may be modified with surface functional groups. For example, a PES membrane may be modified to include surface functional groups. The modification may be designed to reduce or inhibit fouling on the membrane surface. Thus, the functional groups may be selected to reduce or inhibit affinity of a known or suspected foulant, based on the nature and composition of fluid to be introduced. For example, the membrane may be engineered to reduce binding of proteins and cells. In some embodiments, the surface functional groups may be hydrophilic. In some embodiments, the surface functional groups may be hydrophobic.

The presence of proteins in the delivery fluids may adversely affect the membrane performance leading to membrane fouling and excessive inlet pressure in the system. Membrane fouling is generally a non-linear process dependent on process flow rates. Thus, delivery flow rates for the fluids, including cells and/or particles, may be selected according to the delivery composition of the fluid and properties of the membrane to reduce operational pressures in the device. In the exemplary application of transduction of activated T cells using viral particles, an effective operation flow rate can be selected without impacting the transduction performance in the system.

In certain embodiments, the membrane may comprise surface-bound activation particles. For instance, the membrane may comprise antibodies and/or antigens for activation of the cells bound to a surface of the membrane. Such a device may be configured to receive the cells and distribute the cells along the surface of the membrane for activation, for instance, without requiring introduction of activation particles. Such a device may be configured to receive and distribute the cells to be activated as a monolayer on the membrane, increasing cell interaction with bound activation particles. Thus, in certain embodiments, devices for activation of cells are disclosed herein. The device may be similar to the device for treatment of cells with particles, except that the plurality of pores dimensioned to prevent passage of cells need not be dimensioned to prevent passage of particles, at least because such particles are bound to the membrane.

In some embodiments, the device may operate at a flow rate substantially similar to physiological flow rates. The device may operate at a flow rate of at least about 0.1 ml/min, at least about 0.2 ml/min, at least about 0.3 ml/min, at least about 0.4 ml/min, at least about 0.5 ml/min, at least about 0.6 ml/min, at least about 0.7 ml/min, at least about 0.8 ml/min, at least about 0.9 ml/min, at least about 1.0 ml/min, at least about 1.2 ml/min, at least about 1.3 ml/min, at least about 1.5 ml/min, at least about 1.8 ml/min, or at least about 2.0 ml/min. The device may operate at different flow rates for different operations. Generally, the device may be constructed to withstand and operate at flow rates between about 10 μl/min to about 600 ml/min or more, for example, up to 1,000 ml/min.

In certain embodiments, the surface of the membrane may be modified to enhance treatment of the cells. In the exemplary embodiment of cell transduction, the surface of the membrane may be modified with membrane surface-bound transduction enhancers. For instance, compounds such as fragments of recombinant human fibronectin (rFN-CH-296) may be bound to the surface of the membrane to enhance transduction. Other membrane surface-bound enhancers may be employed, for transduction or other treatment processes.

The device may be designed to have the ability to concentrate cells and virus to a very small local volume. In some embodiments, the cells and virus may be concentrated to as thin as one monolayer (see, e.g., FIG. 9B). In other embodiments, the cells and virus may be concentrated to as thin as a several layer multilayer (see, e.g., FIG. 9C). In accordance with certain aspects, the loading cell density and co-localizing fluid flow may be selected to concentrate the cells and particles onto the membrane, creating the desired membrane surface concentration. In some embodiments, cells are distributed substantially evenly across the membrane. Cells may be distributed in a monolayer across the membrane. Cells may be distributed in a multilayer across the membrane.

The interior surface area of the hollow fiber semi-permeable membrane, or collective interior surface area of the plurality of hollow fiber membranes, may be designed for treatment of a target cell population with monolayer or multilayer coverage of the lumen side of the collective membranes, as selected. The collective interior surface area may refer to a sum of the interior membrane surface area of all hollow fiber membranes in the plurality. Thus, in some embodiments, the collective interior surface area of one or more membrane is dimensioned to allow a monolayer or multilayer of cells that are introduced into the device. This will create the highest local concentration against the membrane. The collective interior surface area of the one or more semi-permeable membranes may be between about 20 $mm^2$ and about 250 $mm^2$ for every 1 million cells, depending on cell size. For instance, in exemplary embodiments, the collective interior surface area of the one or more semi-permeable membranes may be between about 5 $cm^2$ and about 250 $cm^2$, for example, about 20 $cm^2$, about 50 $cm^2$, about 100 $cm^2$, or about 200 $cm^2$, for example, for every 1 million cells.

Such a surface area corresponds with a cell surface density ($\sigma$) of approximately 0.4 million cells/$cm^2$ to 4.0 million cells/$cm^2$ for an exemplary device having a membrane surface area of 20 $cm^2$. Optimal cell surface density may generally be dependent on the size of the cells and the ratio of the particles and cells. In some embodiments, collective interior surface area may be selected to correspond with a cell density of between 0.5 million cells/$cm^2$ to 4.0 million cells/$cm^2$, for example, 1.0 million cells/$cm^2$, 1.5 million cells/$cm^2$, 2.0 million cells/$cm^2$, 2.5 million cells/$cm^2$, 3.0 million cells/$cm^2$, 3.5 million cells/$cm^2$, or 4.0 million cells/$cm^2$.

Thus, in some embodiments, the surface area of the lumen side of the hollow fiber semi-permeable membrane or the collective surface area of the lumen side of a plurality of hollow fiber semi-permeable membranes may be selected to correlate with a number and size of the cells to be loaded into the device. The device may be designed to accommodate a monolayer or multilayer of 2 million cells to 500 million cells or 500 million cells to 1 billion cells, for example, 10 million cells to 50 million cells, 50 million cells to 100 million cells, 100 million cells to 500 million cells, 500 million cells to 800 million cells, or 800 million cells to 1 billion cells. The device may be designed to accommodate a monolayer or multilayer of 2 million cells, 5 million cells, 10 million cells, 15 million cells, 20 million cells, 30 million cells, 40 million cells, 50 million cells, 60 million cells, 100 million cells, 200 million cells, 300 million cells, 400 million cells, 500 million cells, 600 million cells, 700 million cells, 800 million cells, 900 million cells, or 1 billion cells. Furthermore, the device may be designed to accommodate a monolayer or multilayer of cells based on the average size of the cells, for example, diameter or volume of the cells. In some embodiments, the size and/or number of particles may also be considered when designing the device. For example, the device may be selected to accommodate a desired ratio of cells and particles. However, it is believed during transduction and activation, the size of the viral particles and/or activation particles may be negligible when compared to the size of the cells.

The device may be scaled with varying length (L), diameter (D), and number of hollow fiber membranes (n). One or more of the length (L), diameter (D), and number of hollow fiber membranes (n) may be selected for the desired use of the device. Total processing throughput of the device may be scaled by controlling at least one of the length (L), diameter (D), number of hollow fiber membranes (n), and cell surface density ($\sigma$). Total processing throughput of the device generally scales with total surface area of the membrane (A), calculated by the equation $A=n\times L\times\pi D$. The systems and methods disclosed herein may be easily and consistently scalable. In particular, the device may be scaled by increasing or decreasing the number of hollow fiber membranes, without sacrificing performance, through linear scaling of processing parameters, such as delivery and co-localizing flow rates.

Volume of the housing may be increased to accommodate an increasing collective interior surface area of the membranes. In some embodiments, the collective interior surface area of the one or more hollow fiber semi-permeable membrane is between about 0.2 $mm^2$ and about 4 $mm^2$ for every 1 $mm^3$ volume of the housing, for example, about 0.5 $mm^2$ for every 1 $mm^3$ volume, or 2.0 $mm^2$ for every 1 $mm^3$ of volume. Exemplary housings may have a total volume of about 1 ml to about 50 ml. Such exemplary housing volumes may correspond to a collective interior surface area of the membrane of from about 20 $cm^2$ to about 250 $cm^2$.

In some embodiments, the device may have a 50%-80% packing ratio of hollow fiber semi-permeable membranes within the housing, for example, the device may have 50%-65%, 55%-70%, 60%-75%, or 65%-80% packing ratio of hollow fiber semi-permeable membranes within the housing. Packing ratio may be defined as percent volume within the housing occupied by volume of the interior flow chamber. In general, the packing ratio may be selected to provide a sufficient transduction area within the device while maintaining the described flow profiles into and out of the hollow fiber membranes.

The semi-permeable membrane may have a thickness of between about 50 μm and about 500 μm, for example, between about 50 μm and about 250 μm, between about 100 μm and about 200 μm, or between about 125 μm and about 175 μm. In general, the thickness of the semi-permeable membrane may be sufficient to withstand the interior pressure of the device during loading and unloading, without collapsing or rupturing the hollow fiber membrane.

The device may comprise a substrate material constructed and arranged to give structural support to the hollow fiber semi-permeable membrane. The substrate material may be positioned adjacent the surface side (exterior) of the hollow fiber semi-permeable membrane. The substrate may be employed to prevent fracturing of the hollow fiber membrane during high flow rates.

In some embodiments, the device may comprise a support material constructed and arranged to give structure support to a bundle of hollow fiber semi-permeable membranes. The support may be positioned adjacent the exterior of the bundle. The support may be employed to keep the plurality of hollow fibers positioned in the bundle and prevent fracturing during high flow rate.

The substrate material and/or support material may have a lower hydraulic resistance than the membrane. The substrate may be, for example a mesh screen, which acts as a structural support for the membrane to allow pathways for fluid to flow through the membrane. The support material may be, for example, a mesh screen, which acts as a structural support for the bundle of membranes. Because the hydraulic resistance of the substrate and/or support is lower than that of the membrane, fluid flow distribution is not affected by the presence of the substrate or support. While the disclosure contemplates a mesh as the substrate material, in general the membrane may be supported by a substrate material with geometries and shape that facilitates the concentrations of cells and virus locally on the opposite side of the membrane while still allowing flow of the media through the membrane, thereby enhancing cell and virus interactions. Additionally, while the disclosure contemplates a mesh as the support material, in general the bundle of membranes may be supported by a support material with geometries and shape that facilitates keeping the plurality of membranes positioned within the device. The device may comprise one or more of the substrate and support materials. Additionally, a device having a plurality of membranes may comprise a respective substrate material giving support to each hollow fiber membrane.

The interior flow chamber of each hollow fiber semi-permeable membrane may be dimensioned to provide a controlled shear stress on the lumen side of the membrane at the operating flow rate. In some embodiments, the controlled shear stress may be a physiological shear stress. The device flow chambers may be dimensioned to reduce shear induced cell damage, for example, to reduce shear stress on the cells. The interior flow chamber of each hollow fiber semi-permeable membrane may have a volume selected to control shear stress generated at the surface of the membrane. Thus, the internal diameter and/or length of the hollow fiber semi-permeable membrane may generally be dimensioned to provide a controlled shear stress, for example, a physiological shear stress, or a shear stress of less than 1 Pa (for example, between 0.05 Pa and 1.0 Pa), during cell loading into the device, and/or a shear stress of less than 10 Pa during unloading and/or treatment of the cells.

Additionally, wall shear stress and flow profile imposed on the cells can be utilized to enhance recovery of the cells from the device. During recovery, wall shear stress is induced by fluid flow rate across a lumen side of the membrane, with or without reverse transmembrane flow. The interior flow chamber may be dimensioned to provide a desirable shear stress that is sufficient to clear the cells during unloading but does not exceed the controlled shear stress at the target flow rate. While not wishing to be bound by theory, it is believed the device provides good recovery at a shear stress of less than 10 Pa and poor recovery at a shear stress of less than 0.1 Pa. Accordingly, the hollow fiber semi-permeable membrane may be dimensioned to provide a shear stress of between 1.0 Pa and 10 Pa, for example, between 3.0 Pa and 10 Pa on the lumen side surface during recovery at the operating flow rates. In certain embodiments, a hollow fiber membrane internal diameter of between about 0.5 mm and about 1.0 mm may provide a desirable shear stress at typical operating flow rates.

As previously described, length (L), diameter (D), and the number of hollow fiber membranes (n) may be selected and optimized for the application. The devices for treatment of cells disclosed herein may be scaled to accommodate a target number of loading cells or desired cell surface density (σ), for example, by increasing a number of hollow fiber semi-permeable membranes, increasing length of the one or more hollow fiber semi-permeable membrane, or increasing diameter of the one or more hollow fiber semi-permeable membrane. However, desired shear stress at the target operating flow rate may generally be considered when selecting internal diameter of the hollow fiber membrane.

In some embodiments, a cross section of the interior flow chamber of each hollow fiber semi-permeable membrane has a diameter of between about 0.25 mm and about 1.00 mm, for example, about 0.25 mm, about 0.5 mm, about 0.75 mm, or about 1.0 mm. As previously described, internal diameter of the hollow fiber membrane may be selected to control shear stress on the cells at the target operating flow rate. However, internal diameter may also be selected to reduce or inhibit blockages or membrane fouling. It is believed smaller diameter hollow fiber membranes may result in blockages. Additionally, internal diameter may be selected to provide adequate cell recovery. It is believed larger diameter hollow fiber membranes may impede cell recovery from the device. Accordingly, the diameter of a cross section of the hollow fiber membrane may be effective to control shear stress, reduce or inhibit lumen blocking or membrane fouling, and provide adequate cell recovery.

Exemplary hollow fiber membranes may have a length of between about 2 cm and about 100 cm, for example, between about 10 cm and about 80 cm, between about 20 cm and about 60 cm, between about 15 cm and about 50 cm, or between about 20 cm and about 40 cm. However, as previously described, the device may be scaled by increasing length of the hollow fiber membrane. It is believed increasing length will not adversely affect device performance. Thus, in certain instances, the hollow fiber membranes may have a length greater than about 100 cm.

In exemplary embodiments, the interior flow chamber of each hollow fiber membrane may have a volume of between about 20 μL and about 360 μL, for example, between about 20 μL and about 240 μL, between about 20 μL and about 120 μL, or between about 20 μL and about 60 μL, or about 20 μL, about 40 μL, or about 60 μL. However, interior flow chamber volume is partly a function of length. Because the device may be scaled by increasing length of the hollow fiber membrane, in some embodiments the interior flow chamber of each hollow fiber membrane may have a volume greater than 360 μL.

In exemplary embodiments, the plurality of hollow fiber membranes may collectively have an interior flow chamber volume of between about 20 μL and about 7.2 mL. The collective interior flow chamber volume may refer to a sum of the interior flow chamber volumes of all hollow fiber membranes in the plurality. For example, the device may have a total interior flow chamber volume of about 20 μL, 60 μL, 120 μL, 240 μL, 360 μL, 480 μL, 600 μL, 720 μL, 1.2 mL, 1.8 mL, 2.4 mL, 3.2 mL, 3.6 mL, 4.8 mL, 5.4 mL, 6.0 mL, or 7.2 mL. The device may be scaled by increasing length of each hollow fiber membrane and/or by increasing the number of hollow fiber membranes. Accordingly, in certain embodiments, the collective interior flow chamber volume of the hollow fiber membranes may be greater than 7.2 mL.

The device may further comprise a temperature control unit configured to control temperature within the device. Temperature control may be employed during treatment of the cells, for example, transduction, activation, expansion, or separation. The temperature control unit may comprise a heater and/or a chiller coupled to the device. The temperature control unit may comprise an insulator configured to substantially maintain a selected temperature within the device. In some embodiments, the temperature control unit may comprise a temperature sensor. The heater and/or chiller may be operatively connected to the temperature control sensor, to heat or cool the cells within the device responsive to a temperature measurement. In some embodiments, the heater and/or chiller may be operatively connected to the temperature sensor via a controller.

The device may further comprise an oscillator. The oscillator may be coupled to the device and configured to provide oscillatory flow of fluids into the hollow fiber membrane. Oscillatory flow may be defined as flow having a variable flow rate over time. Oscillatory flow may be provided during loading of cells and/or particles into the device. The oscillatory flow may be effective to improve distribution of the cells and the particles within the device. Oscillatory flow may be provided during transduction of the cells. The oscillatory flow may be effective to increase transduction efficiency. Oscillatory flow may be provided during recovery of cells and/or particles from the device. The oscillatory flow may be effective to dislodge the cells from the membrane, increasing recovery, without decreasing viability of the cells. Thus, in some embodiments, one or more of the biosample, treatment agent, and a media fluid may be introduced with an oscillatory flow, for example, at a variable flow rate. In some embodiments, the oscillator may comprise a peristaltic pump. The peristaltic pump may be fluidly connected to one or more of the source of the biosample, the source of the treatment agent, and the source of at least one media fluid. The system may have one or more peristaltic pumps fluidly connected to the luminal inlet and/or the housing inlet. In some embodiments, the oscillator may be operatively connected to a controller.

The device may further comprise an acoustic transducer. The acoustic transducer may be coupled to the device and configured to provide acoustic energy to the hollow fiber membrane and cells on the membrane surface. Acoustic energy may be employed during recovery of cells from the device. The acoustic energy may be effective, for example, having an appropriate magnitude and frequency, to dislodge the cells from the membrane, increasing recovery. In some embodiments, the oscillator may be operatively connected to a controller.

The device may further comprise an aerator or a source of an oxygen containing gas. The aerator or source of gas may be fluidly connected to the interior flow chamber and/or exterior flow chamber within the housing. The aerator or oxygen containing gas may be employed to maintain viability of the cells within the device. In some embodiments, the aerator or oxygen containing gas may be employed during recovery of cells from the device. Bubbles may be introduced to dislodge the cells form the membrane, increasing recovery. In some embodiments, the aerator or source of an oxygen containing gas may be operatively connected to a controller.

Any of the inlet and outlets of the device may be fitted with valves, for example, check valves and/or flow control valves. For example, the device may comprise a luminal inlet valve, a luminal outlet valve, a housing inlet valve, and/or a housing outlet valve. In certain embodiments, the device may comprise a luminal recycle line valve and/or a housing recycle line valve. The valves may be actuated to control direction of fluid through the device. The valves may be actuated to control pressure within the device. Thus, in some embodiments, the valves may be operatively connected to a controller for automatic actuation in accordance with a predetermined protocol.

The device may comprise integrated Luer and/or barbed fittings. The device may contain gasket sealed components. The device may contain fasteners, for example screws, to attach one or more components. In some embodiments, the device may be injection molded. The device components be fastened together by any suitable methods.

The devices disclosed herein may be substantially sterile when in use, for example, being formed of a material that is sterilizable. The device may be sterilizable, for example, by gamma irradiation, autoclave sterilization, ethylene oxide, or other sterilization methods. In general, the device may be compatible with available bioprocessing components. For example, the device may comprise a polycarbonate, polyether sulfone, or polyvinylidene fluoride material. The device may further comprise acrylic components. The device may be constructed to withstand up to up to 4000 mmHg (5.3 bar) of pressure without leaking. In some embodiments, the devices disclosed herein may be single-use devices. In some embodiments, the devices disclosed herein may be multi-use devices.

Figure 7:
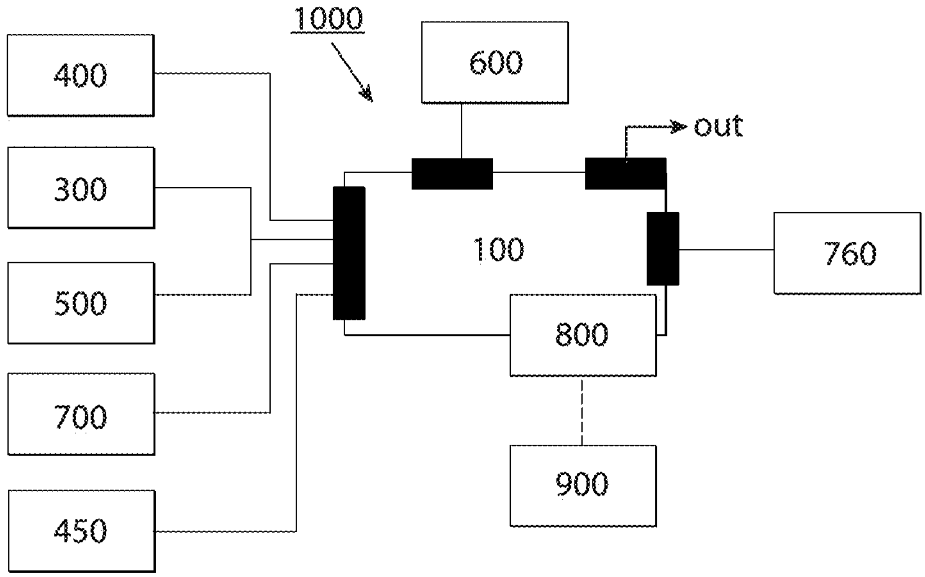
FIG. 7 is a box diagram of a system for treatment of cells, according to one embodiment.
Figure 8:
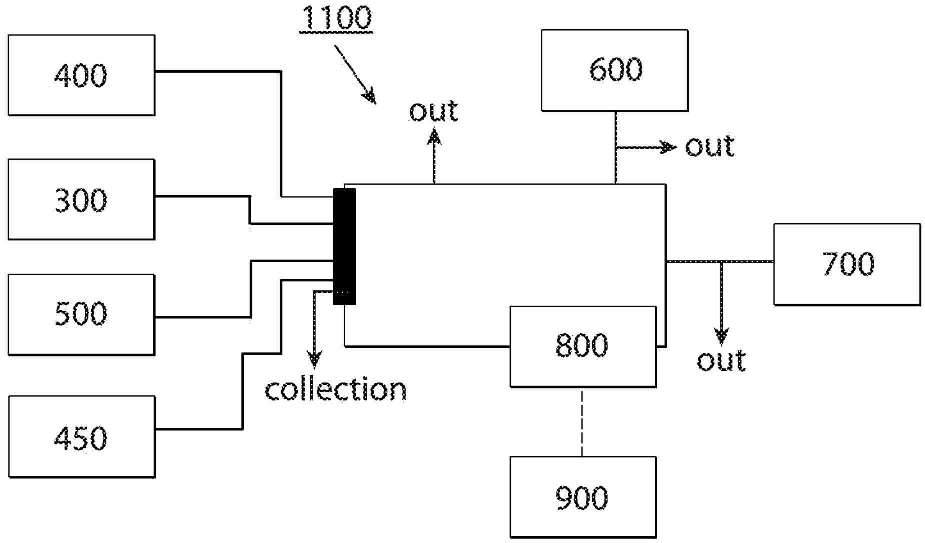
FIG. 8 is a box diagram of a system for treatment of cells, according to one embodiment.

In accordance with another aspect, there is provided a system for treatment of cells. Exemplary system 1000 is shown in the diagram of FIG. 7. Exemplary system 1100 is shown in the diagram of FIG. 8. The systems 1000, 1100 may comprise a device 100 for treatment of cells, as previously described. The systems 1000, 1100 may comprise a source of a biosample fluid 300 comprising the cells fluidly connected to the luminal inlet of the device 100. In some embodiments, the systems 1000, 1100 may comprise a source of a treatment agent 500 comprising the particles fluidly connected to the luminal inlet of the device 100. The systems 1000, 1100 may comprise a source of a co-localizing fluid 400 fluidly connected to the luminal inlet of the device 100. The systems 1000, 1100 may comprise a source of a recovery fluid 700 fluidly connected to the luminal inlet (as shown in system 1000 of FIG. 7) or the luminal outlet (as shown in system 1100 of FIG. 8) of the device 100. The systems 1000, 1100 may comprise a source of a releasing fluid 600 fluidly connected to the housing inlet (as shown in system 1000 of FIG. 7) or the housing outlet (as shown in system 1100 of FIG. 8) of the device 100. The systems 1000, 1100 may comprise a source of a priming fluid 450, fluidly connected to the luminal inlet of the device 100. The systems 1000, 1100 may comprise a collection chamber 760, as shown in FIG. 7, fluidly connected to the luminal outlet or the luminal inlet.

In the embodiments of FIGS. 7-8, each of the source of the co-localizing fluid 400, the source of the recovery fluid 700, the source of the releasing fluid 600, and the source of the priming fluid 450 are shown as distinct entities. However, one or more of the co-localizing fluid 400, the recovery fluid 700, the releasing fluid 600, and the priming fluid 450, may originate from the same source, for example, from the same vessel. In certain embodiments, the co-localizing fluid 400, the recovery fluid 700, the releasing fluid 600 originate from the same vessel, while the priming fluid 450 originates from another vessel.

In some embodiments, as shown in the system 1000 of FIG. 7, the source of the biosample fluid 300 and the source of the treatment fluid 500 are fluidly connected to produce a mixed fluid, also referred to as a "mixed sample" herein, comprising the cells and the particles upstream from the luminal inlet of the device 100.

In some embodiments, as shown in system 1100 of FIG. 8, the source of the biosample fluid 300 and the source of the treatment fluid 500 are each independently fluidly connected to the luminal inlet of the device 100. Thus, in such embodiments, the cells and the particles are separately introduced into the device 100. In some embodiments, the cells may be introduced into the device 100 before the particles. In other embodiments, the particles may be introduced into the device 100 before the cells.

The system 1000 may comprise a controller 900 and a sensor and/or control unit 800, described in more detail below.

The systems 1000, 1100 of FIGS. 7-8 are exemplary. It should be understood that aspects of the system 1000 as shown in FIG. 7 may be combined with aspects of the system 1100 as shown in FIG. 8.

Any one or more of the fluids, for example, biosample fluid, treatment fluid, co-localizing fluid, recovery fluid, releasing fluid, and/or priming fluid, may be any physiologically acceptable fluid, comprising, for example, cell media, saline, buffers, and other fluids. The fluids disclosed herein may additionally comprise nutrients and/or treatment enhancers, such as transduction or activation enhancers. In accordance with certain embodiments, the fluids do not generally comprise chemical enhancers that may be detrimental to the health of the cells or a subject. Thus, in certain embodiments, one or more of the fluids, for example, biosample fluid, treatment fluid, co-localizing fluid, recovery fluid, releasing fluid, and/or priming fluid, may be substantially free of chemical enhancers and other adverse compounds.

Any one or more of the fluids may comprise cell culture media, which may comprise serum or be free of serum. Exemplary cell culture media include media with 5% human serum, media with 10% human serum, media with 10% fetal bovine serum, and media which is free of serum. The media may include those distributed by Lonza Chemical Company (Basel, Switzerland), Miltenyi Biotech Company (Bergisch Gladbach, Germany), or Gibco (ThermoFisher Scientific, Waltham, MA), for example.

Any one or more of the fluids may comprise a buffer, for example, a saline or other physiologically acceptable solution.

In some embodiments, any one or more of the fluids, may comprise a transduction enhancer. Suitable transduction enhancers may include polymers, for example, cationic polymers. Transduction enhancers may include, for example, Retronectin (Clontech, Mountain View, CA), Polybrene (Sigma-Aldrich, St. Louis, MO), and Lentiboost (Sirion Biotech, Martinsried, Germany).

In some embodiments, any one or more of the fluids, may comprise an activation reagent. Activation reagents may include, for example, antigens or antibodies. Optionally, the antigens or antibodies may be coated on an activation bead. For example, the activation reagent may include Dynabeads (ThermoFisher Scientific, Waltham, MA).

In some embodiments, the system may comprise a source of a priming fluid fluidly connected to the luminal inlet. The priming fluid may be a buffer, for example, a saline or other physiologically acceptable solution. The priming fluid may be, for example, similar to the biosample fluid or the treatment fluid without comprising the cells and/or particles. The priming fluid may comprise nutrients and/or treatment enhancers, as previously described. The priming fluid may be introduced into the device prior to introducing the cells and/or particles to prime the membrane for cell or particle interactions.

In some embodiments, the system may comprise a source of a media exchange fluid fluidly connected to the luminal inlet. The media exchange fluid may be, for example, similar to the biosample fluid or the treatment fluid without comprising the cells and/or particles. The media exchange fluid may comprise nutrients and/or treatment enhancers, as previously described. The media exchange fluid may be introduced into the device during treatment, to maintain cell viability, especially during longer treatment periods.

The system may further comprise a collection chamber fluidly connected to at least one of the luminal inlet and the luminal outlet. The collection chamber may be configured and arranged to collect treated and/or separated cells from the device. In some embodiments, the collection chamber may be suitable for storage, for example, short term or long-term storage. Thus, the collection chamber may be suitable for refrigeration, freezing, and or cryopreservation of the treated and/or separated cell sample.

The devices and systems disclosed herein may be part of an automated system, for example, a closed automated system. The system may operate to deliver cells, particles, activate, transduce, separate, expand, and/or recover cells. Certain treatment steps, for example, transduction or activation, within the automated device or system may be timed. The automated system may control temperature and/or pressure to enhance transduction and/or viability of the cells. The automated system may be integrated into an overall bioprocessing system capable of producing a therapeutically acceptable product. The system may include and perform additional steps before and/or after activation, transduction, and recovery, to produce the therapeutically acceptable product.

Thus, in some embodiments, the source of the biosample fluid may be connectable to an intraluminal line in fluid communication with a donor subject. The intraluminal line may be configured to extract the biosample fluid comprising the cells to be treated from a donor. The device may further be fluidly connectable to an intraluminal line in fluid communication with a recipient subject. The intraluminal line may be connected, for example, to the collection chamber. In some embodiments, the donor subject and the recipient subject are the same. In other embodiments, the donor subject and the recipient subject are not the same.

As used herein, a "subject" may include an animal, a mammal, a human, a non-human animal, a research animal, a livestock animal, or a companion animal. The term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the disclosure includes all vertebrates, for example, non-mammals (such as birds, for example, chickens; amphibians; reptiles) and mammals, such as non-human primates, research, domesticated, and agriculturally useful animals, for example, sheep, dog, cat, cow, pig, mouse, rat, among others.

As previously described, the system or device may comprise a luminal inlet valve, a luminal outlet valve, a housing inlet valve, and/or a housing outlet valve. The system may further comprise a biosample valve, a treatment agent valve, a mixed sample valve, and at least one media fluid valve (for example, one or more of a priming fluid valve, a co-localizing fluid valve, a recovery fluid valve, and a releasing fluid valve). Each of the valves may be formed by one or more valves, for example, one valve, two valves, three valves, or more. The system may further comprise one or both of a luminal inlet pump and a housing inlet pump. The system may comprise a biosample pump, a treatment agent pump, and at least one media fluid pump (for example, one or more of a priming fluid pump, a co-localizing fluid pump, a recovery fluid pump, and a releasing fluid pump). Each of the pumps may be formed by one or more pumps, for example, one pump, two pumps, three pumps or more. In some embodiments, the system comprises more than one luminal inlet pump or housing inlet pump. The more than one pump may be positioned in parallel or in series.

In certain embodiments, the system may further comprise a controller operably connected to one or more of the luminal inlet valve, the luminal outlet valve, the housing inlet valve, and/or the housing outlet valve; the biosample valve, the treatment agent valve, the mixed sample valve, and/or the at least one media fluid valve. The controller may be operably connected to one or more of the luminal inlet pump and/or the housing inlet pump; the biosample pump, the treatment agent pump, and/or the at least one media fluid pump. The controller may be configured to actuate any one or more of the pumps and valves to direct fluids within the system according to the methods described herein.

In one exemplary embodiment, the controller may be configured to actuate one of the luminal inlet pump, the luminal inlet valve, the biosample valve, the treatment agent valve, and the housing outlet valve to introduce the biosample fluid comprising the cells and/or the treatment fluid comprising the particles. The biosample fluid and the treatment fluid may be introduced simultaneously or sequentially, as previously described. The biosample fluid and the treatment fluid may be combined prior to being introduced into the treatment device to produce a mixed sample. In such embodiments, the biosample valve and the treatment agent valve may be actuated (open) and the luminal inlet pump may be actuated to direct the mixed sample into the device. An optional mixed sample valve may also be actuated (open). The system may comprise a mixer to combine the biosample and the treatment fluid, optionally into a substantially homogeneous mixture. During loading of the cells and/or particles, the luminal outlet valve may be closed. The fluids may be directed through the membrane and discharged from the device through the housing outlet valve, leaving the cells and/or particles on a lumen side of the membrane.

The controller may be configured to actuate a media fluid pump and/or one of the luminal inlet valve or the luminal outlet valve to introduce the co-localizing fluid into the device. The co-localizing fluid may co-localize the cells and particles on the membrane surface. During co-localization, the fluids may be directed through the membrane and discharged from the device through the housing outlet valve or the luminal outlet valve.

The controller may be configured to actuate a media fluid pump and/or one of the luminal inlet valve or the luminal outlet valve to introduce the recovery fluid to suspend the cells and/or particles in the fluid. The cells and/or particles may be discharged through an opposite end of the lumen, for example, through the luminal inlet or luminal outlet, respectively.

The controller may be configured to actuate a media fluid pump and/or one of the housing inlet valve or the housing outlet valve to introduce the releasing fluid to release cells and/or particles from the membrane surface. The releasing fluid may be discharged with the cells and/or particles through an end of the lumen, for example through the lumen inlet or the lumen outlet. In certain embodiments, the releasing fluid may be introduced at least partially simultaneously with the recovery fluid to produce an intermediate sample or a treated cell sample. In some embodiments, the controller may be configured to actuate the respective valves to introduce the recovery fluid and the releasing fluid substantially simultaneously.

The controller may be a computer or mobile device. The controller may comprise a touch pad or other operating interface. For example, the controller may be operated through a keyboard, touch screen, track pad, and/or mouse. The controller may be configured to run software on an operating system known to one of ordinary skill in the art. The controller may be electrically connected to a power source. The controller may be digitally connected to the one or more components. The controller may be connected to the one or more components through a wireless connection. For example, the controller may be connected through wireless local area networking (WLAN) or short-wavelength ultra-high frequency (UHF) radio waves. The controller may further be operably connected to any additional pump or valve within the system, for example, to enable the controller to direct fluids or additives as needed. The controller may be coupled to a memory storing device or cloud-based memory storage.

Multiple controllers may be programmed to work together to operate the system. For example, a controller may be programmed to work with an external computing device. In some embodiments, the controller and computing device may be integrated. In other embodiments, one or more of the processes disclosed herein may be manually or semi-automatically executed.

In some embodiments, the system may further comprise a temperature control unit operably connected to the controller. The temperature control unit may be configured to modify or control temperature within the device. The temperature control unit may be configured to control temperature to a desired reaction temperature for treatment of the cells. In some embodiments, the temperature is between about 20° C. and about 40° C. The desired reaction temperature may be room temperature, for example, between about 20° C. and about 25° C. The desired reaction temperature may be body temperature, for example, between about 36° C. and about 38° C.

The system may further comprise a temperature sensor operably connected to the controller. The controller may be configured to instruct the temperature control unit to control temperature within the device, for example, responsive to a temperature measurement received from the temperature sensor.

The system may further comprise a pressure sensor operably connected to the controller. The controller may be configured to actuate one or more pumps or valves to increase or decrease pressure within the device, for example, responsive to a pressure measurement obtained by the pressure sensor.

The system may comprise a pH control unit. The pH control unit may be configured to modify or control pH of a fluid within the device. The pH control unit may comprise a source of an acid and/or a source of a base. The pH control unit may be configured to control pH to a desired reaction pH for treatment of the cells. In some embodiments, the desired reaction pH is selected responsive to the cell type. Different physiological pH may be used during treatment of the cells. In some embodiments, the pH control unit may control pH within about 6.0 and about 8.5.

The system may further comprise a pH sensor operably connected to the controller. The controller may be configured to instruct the pH control unit to control pH within the device, for example, responsive to a pH measurement received from the pH sensor.

The system may further comprise a weight sensor configured to monitor weight of a chamber, such as the collection chamber or a waste chamber. The weight sensor may be operably connected to the controller. The controller may be configured to actuate one or more pumps or valves to direct a fluid within the device to waste, for example, responsive to a weight measurement obtained by the weight sensor indicating that the collection chamber is full. In other embodiments, the controller may be configured to notify a user of a chamber being full or almost to capacity.

The system may further comprise a bubble sensor or bubble detector. The bubble sensor may be configured to detect bubbles downstream from the source of the biosample, source of the treatment agent, or source of a media fluid. The bubble sensor may be fluidly connected to the source or external to a flow path of the source. The bubble sensor may be operably connected to the controller. The controller may be configured to actuate one or more pumps or valves to increase or decrease flow rate of a fluid, for example, to purge the device, responsive to the bubble sensor detecting bubbles within the device.

The controller may be operably connected to an oscillatory pump. For instance, in some embodiments, at least one of the luminal inlet pump, the housing inlet pump, the biosample pump, the treatment agent pump, and the media fluid pump is configured to oscillate flow rate. The oscillatory pump may be a peristaltic pump. The controller may be configured to activate the oscillatory pump to oscillate flow rate during loading, treatment, and/or recovery of the cells from the device.

The controller may be operably connected to an acoustic transducer. The controller may be configured to activate the acoustic transducer during recovery of the cells from the device.

Figure 16:
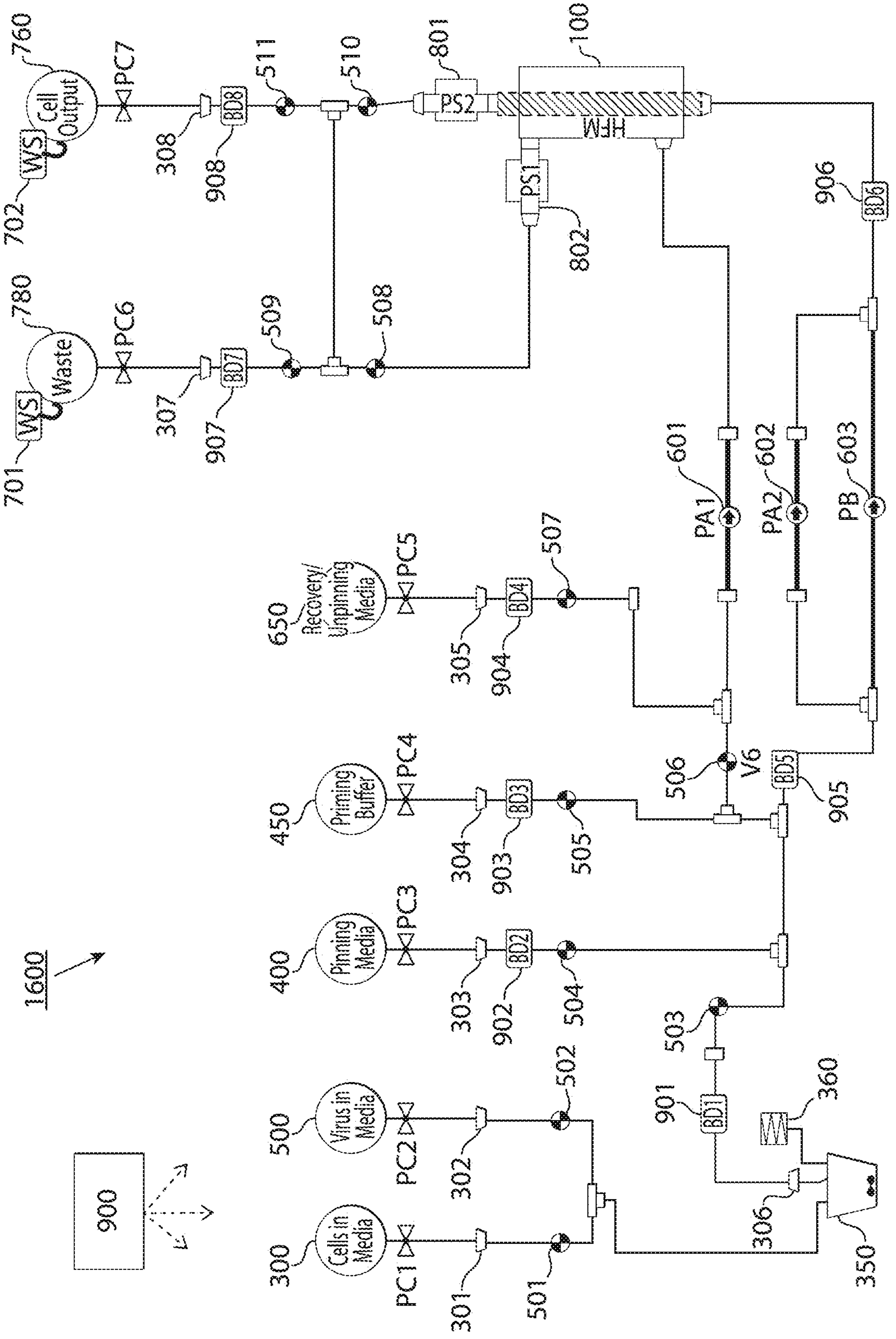
FIG. 16 is a schematic diagram of a system for treatment of cells, according to one embodiment.
Figure 17:
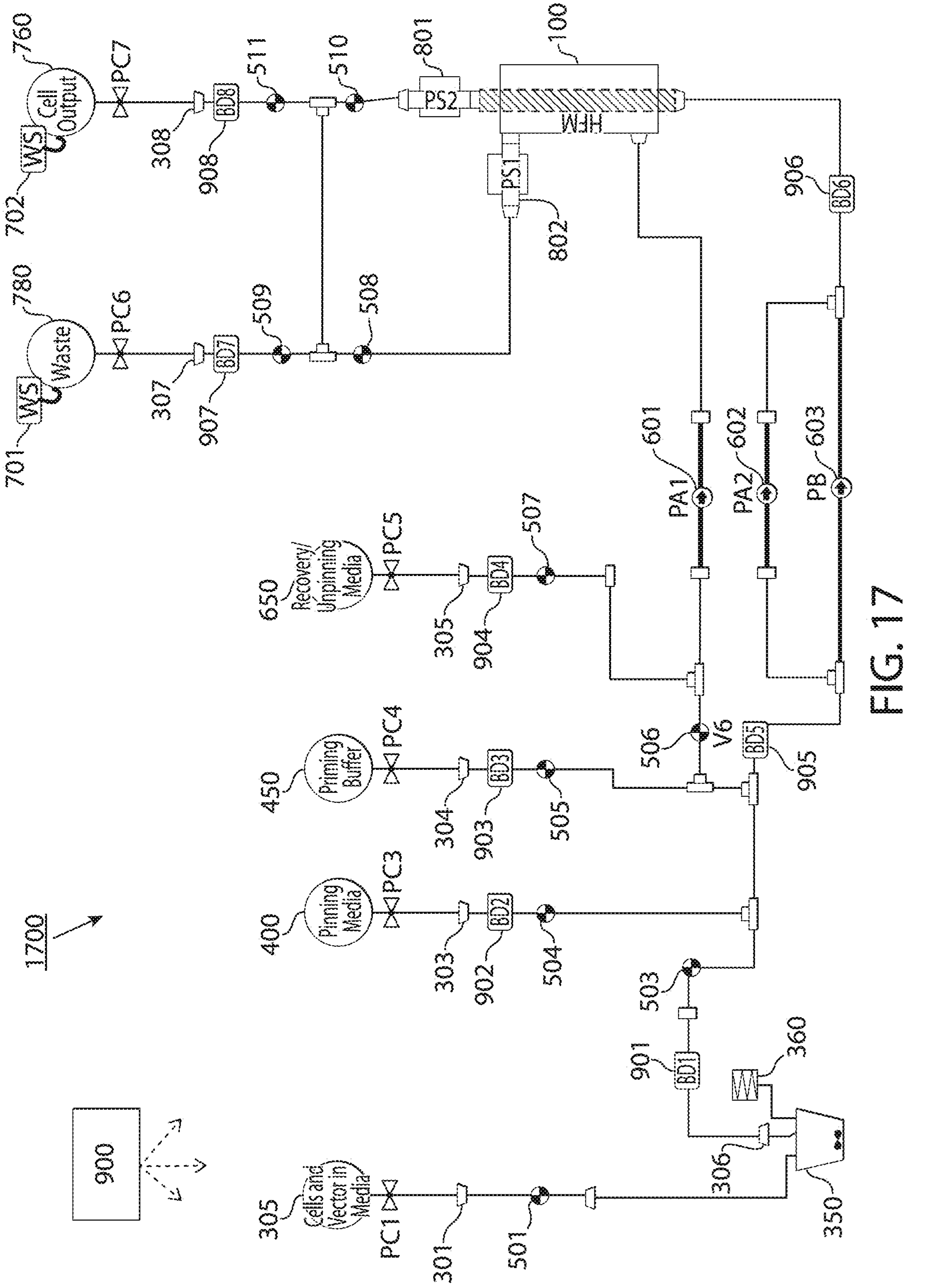
FIG. 17 is a schematic diagram of a system for treatment of cells, according to one embodiment.

FIGS. 16-17 include schematic drawings of exemplary systems 1600, 1700, respectively. FIG. 16 is a schematic drawing of system 1600 which can be used to introduce the biosample comprising cells and the treatment agent comprising particles sequentially or simultaneously through a mixer. Sequential delivery may be used to filter the treatment agent through the semi-permeable membrane prior to introducing the biosample, for example, when the treatment agent is unpurified. FIG. 17 is a schematic drawing of system 1700 which may be used to introduce a mixed sample comprising cells and particles. The mixed sample may be maintained or cultured for a period of time prior to being directed to the treatment device. System 1700 may also be used with a source of a biosample comprising cells (replacing the source of the mixed sample) in embodiments in which the treatment agent is bound to a surface of the membrane and not introduced into the treatment device.

System 1600 includes treatment device 100 having a housing and a hollow fiber semi-permeable membrane. The treatment device 100 is positioned in an upright orientation, with the luminal inlet on a bottom end of the treatment device 100. System 1600 includes source of biosample 300 and source of treatment agent 500 fluidly connected to a luminal inlet of the treatment device 100. Source of biosample 300 and source of treatment agent 500 are fluidly connected upstream from the treatment device through mixer 350 which comprises a filter 360 configured to allow aseptic gas exchange. Through the piping design of system 1600, mixer 350 is also fluidly connected to the housing inlet of treatment device 100. Thus, in certain embodiments, system 1600 may be operated to introduce cells and/or particles along a surface side of the hollow fiber semi-permeable membrane.

System 1600 also includes source of co-localizing fluid 400 and source of priming fluid 450 fluidly connected to the luminal inlet of the treatment device 100. Source of co-localizing fluid 400 is also fluidly connected to the housing inlet of the treatment device 100 for treatment of the cells and/or particles along the surface side of the hollow fiber semi-permeable membrane. Source of priming fluid 450 is also fluidly connected to the housing inlet of the treatment device 100.

System 1600 includes source of media fluid 650 fluidly connected to the luminal inlet and the housing inlet of treatment device 100. Source of media fluid 650 may be directed to the luminal inlet of treatment device 100 for recovery of cells and/or particles from the interior flow chamber. Source of media fluid 650 may be directed to the housing inlet of treatment device 100 for release of cells and particles from the lumen side surface of the semi-permeable membrane. In some embodiments, the system may comprise separate sources of releasing fluid and recovery fluid (as shown in FIGS. 7-8). It should be noted that source of media fluid 650 may be directed to the housing inlet for recovery of cells and/or particles and to the luminal inlet for release of the cells and/or particles during treatment of the cells on the surface side of the hollow fiber semi-permeable membrane.

System 1600 includes collection chamber 760 fluidly connected to the luminal outlet of the treatment device 100 and waste chamber 780 fluidly connected to the housing outlet of the treatment device 100. As also shown in system 1600, for example, for treatment of cells on the surface side of the hollow fiber semi-permeable membrane, collection chamber 760 is also fluidly connected to housing outlet and waste chamber 780 is fluidly connected to luminal outlet through a connector.

System 1600 includes a plurality of valves 501-511 (biosample valve 501), (treatment agent valve 502), (mixed sample valve 503), (co-localizing fluid valve 504), (priming fluid valve 505), (housing inlet valve 506), (media fluid valve 507), (housing outlet valve 508), (waste chamber valve 509), (luminal outlet valve 510), (collection chamber valve 511). A luminal inlet valve may be used instead of or in addition to the housing inlet valve 506 to selectively direct fluids to the luminal inlet or the housing inlet. System 1600 includes pumps 601, 602, 603 fluidly connected to the housing inlet and luminal inlet respectively. In the exemplary embodiment of FIG. 16, housing inlet pump 601 and luminal inlet pumps 602-603 are peristaltic pumps. System 1600 also includes optional pumps 301-306 (biosample pump 301), (treatment agent pump 302), (co-localizing fluid pump 303), (priming fluid pump 304), (media fluid pump 305), (mixed sample pump 306). Each of the valves 501-511, pumps 601-603, and pumps 301-306 may be operably connected to controller 900.

System 1600 includes pressure sensors 801, 802 downstream from the luminal outlet and housing outlet, respectively. System 1600 includes weight sensors 701, 702 configured to measure weight of the collection chamber 760 and waste chamber 780, respectively. System 1600 includes bubble detectors 901, 902, 903, 904, 905, 906, 907, 908 configured to detect bubbles downstream from the mixer 350, co-localizing fluid 400, priming fluid 450, media fluid 650, or upstream from the luminal inlet of the treatment device 100, waste chamber 780, and collection chamber 760. Each of the pressure sensors 801-802, weight sensors 701, 702, and bubble detectors 901-908 may be operably connected to controller 900.

System 1700 is similar to system 1600 and may be operated similarly to system 1600, except that source of mixed sample 305 includes cells and particles. In the system of 1700, cells and particles may be combined prior to being introduced into the system. The cells and particles may be maintained or cultured together for a period of time prior to being introduced into the system, for example, prior to being directed to the treatment device 100, optionally though mixer 350.

In some embodiments, the system may comprise more than one device fluidly connected in series. For example, the system may comprise any two or more of an activation device, a transduction device, an expansion device, and/or a separation device arranged in series. Thus, in some embodiments, an end to end system is provided for treatment of cells, optionally obtained from a donor subject, to produce a therapeutic product, optionally a finished therapeutic product for delivery to a recipient subject.

In construction and geometry, the devices may be similar. Membrane pore size may be varied, for example, for separation of the cells. The source of the treatment fluid may be varied, for example, for transduction or activation of the cells. In other embodiments, one or more of the devices may be structurally different from one another.

Figure 18:
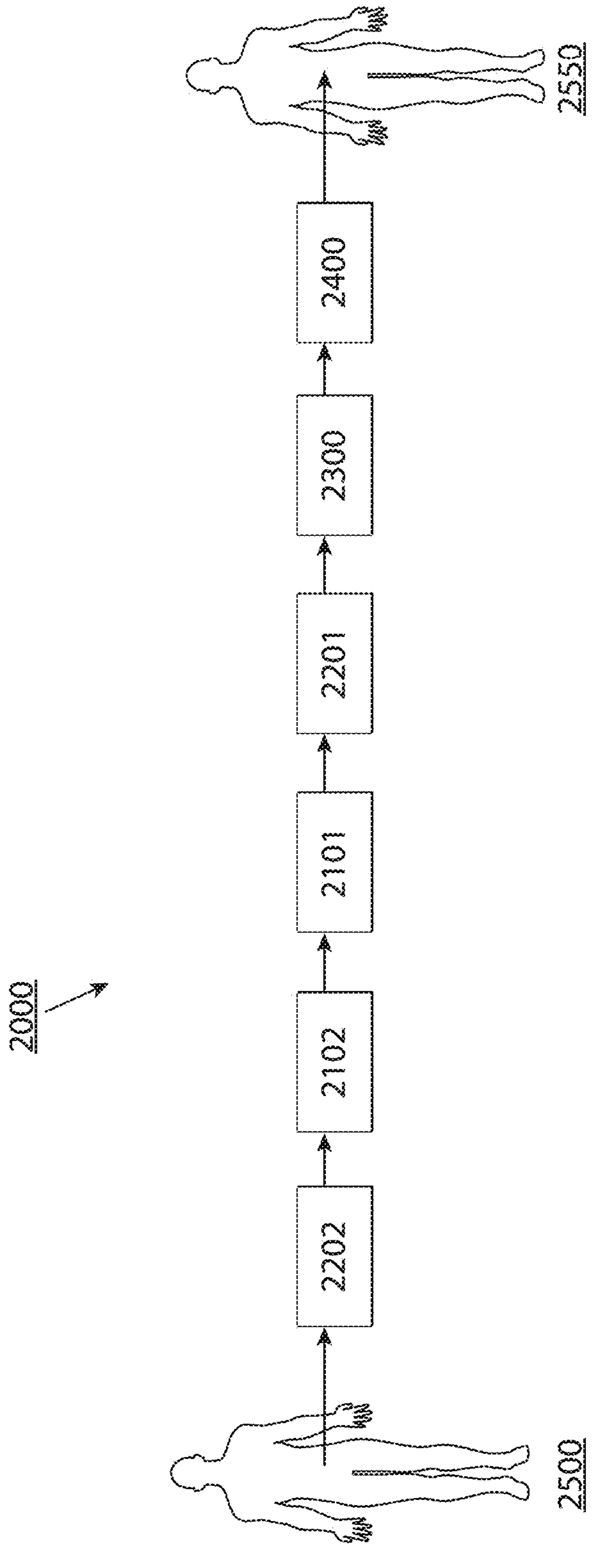
FIG. 18 is a schematic diagram of a system for treatment of cells, according to one embodiment.

An exemplary end to end system 2000 is shown in the box diagram of FIG. 18. System 2000 includes an activation device 2102 fluidly connected to a transduction device 2101. System 2000 is configured to be fluidly connectable to an intraluminal line of a donor subject 2500. System 2000 comprises a separation device 2202 configured to select for a target cell type from a sample obtained from the donor subject 2500. System 2000 includes a separation device 2201 configured to separate transduced cells from particles. System 2000 includes an expansion device 2300 and a quality control device 2400 configured to produce a therapeutic product and determine whether the therapeutic product is suitable for delivery to a recipient 2550. Thus, system 2000 is configured to be fluidly connectable to an intraluminal line of a recipient subject 2550.

The transduction device 2101 may comprise an elongated housing having a luminal inlet, a luminal outlet, a housing inlet, and a housing outlet and a hollow fiber semi-permeable membrane extending between the luminal inlet and the luminal outlet, as previously described. The activation device 2102 may comprise an elongated housing having a luminal inlet, a luminal outlet, a housing inlet, and a housing outlet and a hollow fiber semi-permeable membrane extending between the luminal inlet and the luminal outlet, as previously described. The luminal outlet of the activation device 2102 may be fluidly connectable to the luminal inlet of the transduction device 2101 for delivery of the activated cells as cells to be transduced.

In some embodiments, the transduction device 2101 and the activation device 2102 may be the same hollow fiber membrane device, referred to herein as a combined treatment device. The combined treatment device may comprise a membrane having surface bound activation particles. In use, cells to be activated may be delivered to the treatment device to contact the surface bound activation particles. The cells may be maintained in contact with the surface bound activation particles and allowed to interact for a period of time effective to activate the cells or a majority of the cells. Viral particles from a source of a treatment agent may be introduced into the device to contact the activated cells. The activated cells may be maintained in contact with the viral particles and allowed to interact for a period of time effective to transduce the cells. Transduced cells may be discharged from the combined treatment device, as previously explained. Thus, in some embodiments, a combined treatment device may be employed to reduce complexity of the system.

The separation device 2202 configured to separate target cells from non-target cells may have an inlet fluidly connectable to the intraluminal line and a first outlet fluidly connectable to deliver target cells to the transduction device 2101, optionally through the activation device 2102. The separation device 2202 may be configured to select for a target cell type. In some embodiments, the separation device 2202 comprises a membrane having surface-bound antibodies configured to bind the target cells and leave non-target cells unbound. The non-target cells may be discharged from the device. The target cells may be unbound from the membrane surface, for example, by introducing a separating buffer into the device and suspending the target cells in a buffer suspension. Thus, in some embodiments, the separation device 2202 is fluidly connectable to a source of a separating buffer. Similarly, in other embodiments, the separation device 2202 comprises a membrane having surface-bound antibodies configured to bind the non-target cells and leave target cells unbound. The non-target cells may remain immobilized on the membrane until regeneration of the membrane is necessary or the separation device may be replaced with a fresh device.

In some embodiments, the separation device 2202 for separation of a target cell and the separation device 2201 for separation of transduced cells, may comprise a housing having an inlet, a first outlet, and a second outlet. The inlet may be fluidly connected to receive the cells to be separated. The first outlet may be configured to deliver a selected product, such as a target cell or a transduced cell. The second outlet may be configured to discharge a non-selected product, such as a non-target cell or a particle. A semi-permeable membrane may be positioned within the housing to define a first flow chamber between the inlet and the first outlet and a second flow chamber opposite the first flow chamber fluidly connected to a second outlet.

The separation device 2201 configured to separate transduced cells from particles may have a semi-permeable membrane having a plurality of pores dimensioned to allow passage of the fluid and the viral particles and prevent passage of the cells. In some embodiments, the separation device 2202 configured to separate target cells from non-target cells may have a semi-permeable membrane having a plurality of pores dimensioned to allow passage of the fluid and prevent passage of the target cells. Exemplary devices are described, for example, in U.S. Patent Application Publication No. 2019-0085280, titled APPARATUS FOR EFFICIENT GENETIC MODIFICATION OF CELLS, filed Sep. 20, 2018, incorporated herein by reference in its entirety for all purposes. In other embodiments, the semi-permeable membrane may be a hollow fiber membrane and the housing may be an elongated housing, as described herein.

For example, the semi-permeable membrane of separation device 2201 or separation device 2202 may have an average pore size of between about 50% and about 5% of the average diameter of the cells, for example, the transduced cells or the target cells. In certain embodiments, semi-permeable membrane may be a hollow fiber membrane, and the separation devices 2201, 2202 may resemble the hollow fiber membrane devices described herein.

In some embodiments, the membrane dimensioned to allow passage of fluid, and optionally viral particles, and prevent passage of cells, such as transduced cells or target cells, may have a pore diameter of about 400 nm or greater. Generally, the semi-permeable membrane may have an average pore size sufficient to allow passage of particles (for example, virus and activation agents), but retain cells. Thus, the semi-permeable membrane of the separation devices may have an average pore size of between about 200 nm and 5 μm, depending on the cell type. In general, the separation device may have a membrane average pore size of between about 200 nm and 3 μm. For example, the separation device may have a membrane average pore size of about 200 nm, about 500 nm, about 1 μm, about 2 μm, or about 3 μm.

In some embodiments, a separation device, similar to separation device 2201 for separation of cells from particles, may be positioned between activation device 2102 and transduction device 2101. The separation device may have a semi-permeable membrane having a plurality of pores dimensioned to allow passage of the fluid and the activation particles and prevent passage of the activated cells. The device may have an outlet for activated cells fluidly connectable to the luminal inlet of the transduction device 2101. In such embodiments, a purified sample of activated cells may be delivered to the transduction device 2101.

In other embodiments, the activation device 2102 may be directly fluidly connected to the transduction device 2101. The transduction device 2101 may have a semi-permeable membrane having a plurality of pores dimensioned to prevent passage of the cells and viral particles and allow passage of the activation particles. In use, the activated cells and activation particles may be introduced prior to introducing the viral particles for purification of the cells. Alternatively, the activated cells and activation particles may be introduced simultaneously with the viral particles and a co-localizing fluid may be introduced to remove activation particles through the membrane.

The expansion device 2300 may be a vessel or other chamber fluidly connected to the treatment device and configured to receive treated cells for expansion. In some embodiments, the expansion device may have a first inlet fluidly connectable to the luminal outlet of the treatment device, a second inlet fluidly connectable to a source of an oxygen containing gas, and a first outlet fluidly connectable to the inlet of the separation device. The expansion device may have an inlet configured to receive cell media comprising nutrients for cell culture and expansion. The expansion device may have an outlet configured to discharge cell waste and other byproducts. In some embodiments, the expansion device may be a cell culture bag, plate, flask, or other static biological reactor for culture and expansion of cells. The expansion device may be a semi-permeable membrane, microfluidic device, or other dynamic biological reactor for culture and expansion of cells.

In some embodiments, the expansion device may comprise a housing having a first inlet, a second inlet, a first outlet, and a second outlet. The first inlet may be fluidly connected to receive the transduced cells. The second inlet may be fluidly connected to a source of an oxygen containing gas. The first outlet may be configured to deliver expanded cells. The second outlet may be configured to discharge cell waste and byproducts of culture or expansion. A source of a media fluid may be fluidly connected to the first inlet or to a third inlet. A semi-permeable membrane may be positioned within the housing to define a first flow chamber between the first inlet and the first outlet and a second flow chamber opposite the first flow chamber fluidly connected to a second outlet. The second inlet may be fluidly connected to the first flow chamber or the second flow chamber. The optional third inlet may be fluidly connected to the first flow chamber or the second flow chamber.

Exemplary devices are described, for example, in U.S. Patent Application Publication No. 2019-0085280, titled APPARATUS FOR EFFICIENT GENETIC MODIFICATION OF CELLS, filed Sep. 20, 2018, incorporated herein by reference in its entirety for all purposes. In other embodiments, the semi-permeable membrane may be a hollow fiber membrane and the housing may be an elongated housing, as described herein.

The quality control device 2400 may be configured to monitor the cells and detect unwanted cells. Cells accepted by the quality control device may be used in a therapeutic product, for example, a finished therapeutic product, for delivery to a recipient subject. Unwanted cells detected by the quality control device may be directed to waste.

The quality control device may comprise an inlet, a first outlet, and a second outlet. The inlet may be configured to receive cells, for example, transduced cells and/or expanded cells. The inlet may be fluidly connected to the first outlet of the expansion device, as shown in system 2000, or to a luminal outlet of the transduction device. The first outlet may be configured to discharge accepted cells. The first outlet may be fluidly connectable to an intraluminal line for delivery to a recipient subject. The second outlet may be configured to discharge unwanted cells directed to a waste chamber.

Each of the components of the end to end system may be single use devices or multi-use devices. For example, in some embodiments, one or more of the components of system 2000 are sterilizable by autoclave, gamma irradiation, or ethylene oxide sterilization.

Each of the components of the end to end system may comprise one or more sensors and/or control units, for example, temperature sensor, temperature control unit, pH sensor, pH control unit, pressure sensor, pressure control (provided through a controller operably connected to one or more valve and/or pump), bubble sensor, and/or weight sensor.

The end to end system may be dimensioned for treatment of 2 million to 1 billion target cells, for example 2 million to 10 million, 10 million to 100 million, 100 million to 500 million, or 500 million to 1 billion target cells. The separation device for separation of target cells may be dimensioned to process samples with a high cell count, for example, more than 100 million, more than 500 million, more than 1 billion, or more than 5 billion cells. Downstream components, such as the activation device, transduction device, and separation device for separating cells from particles may be dimensioned for treatment of 2 million to 500 million cells or 500 million to 1 billion cells. The expansion device may be dimensioned to receive transduced cells and expand the cells from 2-fold to $10^6$-fold or more, for example, from 2-fold to $10^2$-fold or from $10^2$-fold to $10^6$-fold, or more. The quality control device may be positioned to detect unwanted cells upstream or downstream of the expansion device. Thus, in some embodiments, the quality control device may be dimensioned to monitor 2 million to 500 million or 500 million to 1 billion cells. In other embodiments, the quality control device may be dimensioned to monitor $10^2$ to $10^6$-fold cells.

However, in certain embodiments, one or more of the separation device for separation of target cells, the separation device for separation of cells from particles, and the quality control device may be dimensioned to process cells in a continuous or semi-continuous mode. Thus, in some embodiments, one or more of the separation device for separation of target cells, the separation device for separation of cells from particles, and the quality control device may be dimensioned to process 1 million cells to 100 million cells per minute, for example, 1 million cells to 10 million cells per minute or 10 million cells to 100 million cells per minute.

In accordance with another aspect, there is provided a method of treating cells with the systems and devices disclosed herein. The method of treating cells may be employed for transducing cells with viral particles, activating cells with activation particles, or any other cell treatment. The transduction and activation may occur in the same device. In other embodiments, the transduction and activation may occur in separate devices, for example, devices arranged in series.

The method may comprise introducing a biosample with the cells, generally suspended in a fluid (also referred to as "biosample fluid" herein) into a treatment device against a lumen side of the hollow fiber semi-permeable membrane. In some embodiments, the method comprises introducing a treatment agent with the particles, generally suspended in a fluid (also referred to as "treatment fluid" herein) into the treatment device against the lumen side of the hollow fiber semi-permeable membrane. In other embodiments, the treatment agent, for example, the particles, may be bound to a surface of the membrane, for example, bound to the lumen side of the membrane.

The biosample and/or the treatment agent may be introduced at a flow rate effective to control a wall shear stress on the lumen side of the hollow fiber semi-permeable membrane. In some embodiments, the biosample fluid and/or the treatment fluid may be introduced at a flow rate effective to substantially evenly distribute the cells and particles on the lumen side of the semi-permeable membrane. The method may comprise introducing the cells at a loading rate effective to distribute the cells as a monolayer on the membrane. In other embodiments, the method may comprise introducing the cells at a loading rate effective to distribute the cells as a multilayer on the membrane.

The method may comprise maintaining the cells to be treated, for example, transduced or activated, in contact with the particles on the lumen side of the hollow fiber semi-permeable membrane for an amount of time effective to produce the treated cells in an intermediate sample comprising transduced cells and particles.

In some embodiments, the method may comprise introducing a co-localizing fluid (also referred to as a "media fluid" herein) into the device against the lumen side of the hollow fiber semi-permeable membrane to co-localize the cells and the particles on the lumen side of the semi-permeable membrane. The co-localizing fluid may be introduced by transmembrane flow. The co-localizing fluid may be introduced at a flow rate effective to substantially evenly distribute the cells and the particles are on the lumen side of the semi-permeable membrane. The co-localizing fluid may be introduced substantially continuously during treatment. The co-localizing fluid may be introduced intermittently or periodically during treatment.

The method may comprise introducing one or more of the biosample, the treatment agent, and the co-localizing fluid at an oscillatory flow, as previously described. The oscillatory flow may be effective to improve transduction, for example, by improving mixing of the cells and particles within the device.

In some embodiments, the method may comprise introducing a priming fluid into the treatment device. The priming fluid may be introduced before introducing the cells and/or the particles into the device. The priming fluid may be configured to prime the membrane for cell and/or particle interactions. In some embodiments, the priming fluid may be configured to substantially remove air bubbles within the device. The priming fluid may be introduced for an amount of time effective to remove a protective coating from the membrane. In some embodiments, the priming fluid may comprise nutrients and/or transduction enhancers or activation enhancers. The priming fluid may comprise functional groups configured to bind to the membrane for modification.

In some embodiments, the device may be positioned in an upright orientation. The method may comprise introducing one or both of the biosample and the treatment agent against a direction of gravity. The method may comprise introducing the co-localizing fluid against the direction of gravity. The method may additionally comprise introducing the priming fluid against the direction of gravity. While not wishing to be bound by theory, it is believed that introducing certain fluids against the direction of gravity generally assists in maintaining the device substantially free of air bubbles, improving performance.

Generally, the device and method work by directing a particle-laden fluid containing cells against the lumen side of the semi-permeable membrane for a given period of time. During the time that cells and particles are held against the membrane, fresh media can be perfused in order to replenish nutrients and remove waste products from the living cells. The cells and virus are either held against the membrane with constant convective flow or flow can be oscillated in order to move particles within the flow chamber that is surrounding the membrane.

Thus, the method may comprise introducing the fluids such that the cells are distributed evenly on the lumen side of the membrane. The cells may be distributed as a monolayer on the first side of the semi-permeable membrane. The cells may be distributed as a multilayer on the first side of the semi-permeable membrane. For example, the method may comprise introducing the co-localizing fluid such that the cells and the particles are localized to maximize reaction efficiency.

While not wishing to be bound by any particular theory, it is believed that certain flow conditions within the device may optimize localization of particles on the semi-permeable membrane and recovery of particles from the device after the reaction. Localization of cells and particles on the membrane surface may be a diffusion limited process. In a transduction process, advection and diffusion, designed by optimizing flowrate of fluid in the device, may optimize cell and virus localization on the membrane.

Thus, the flow rate may be selected to distribute the cells substantially evenly across the membrane. As disclosed herein, flow rates may be defined per area of the semi-permeable membrane. In general, the flow rates may be scaled to accommodate between 0.5 million cells and 100 million cells or more, for example, between 2 million cells and 10 million cells, between 10 million cells and 100 million cells, between 100 million cells and 500 million cells, between 500 million cells and 1 billion cells or more. The increase in hollow fiber membrane length to accommodate the number of cells may be associated with an increase in flow rate that will distribute the cells substantially evenly across the membrane.

The loading flow rate of the biosample and/or the treatment agent may be selected to control or maintain an average wall shear stress on the first side of the semi-permeable membrane between about 0.05 Pa and 10 Pa. For example, the flow rate may be selected to maintain an average wall shear stress of between about 0.05 Pa and 1.0 Pa or between about 0.05 Pa and about 3.0 Pa. The loading flow rate may be between about 0.1 ml/min and 65 ml/min. In some embodiments, the loading flow rate may be about 0.125 ml/min, about 1 ml/min, about 5 ml/min, about 10 ml/min, about 25 ml/min, about 40 ml/min, or about 62.5 ml/min. The loading flowrate may be between about 0.025 ml/min/$cm^2$ and 1 ml/min/$cm^2$ surface area of each of the hollow fiber semi-permeable membranes. For example, the loading flow rate may be between about 0.025 ml/min/$cm^2$ and 0.1 ml/min/$cm^2$, about 0.1 ml/min/$cm^2$ and 0.5 ml/min/$cm^2$, and about 0.5 ml/min/$cm^2$ and 1.0 ml/min/$cm^2$. The loading flow rate may be about 0.1 ml/min/$cm^2$ surface area of each of the hollow fiber semi-permeable membranes. Generally, the loading flow rate may depend on the device geometry and length of the hollow fiber semi-permeable membranes.

In some embodiments, the volume of biosample fluid comprising cells loaded into the device is greater than the volume of the interior flow chamber of each hollow fiber membrane, and optionally greater than the volume of all interior flow chambers combined. In such embodiments, the cells are distributed within the hollow fiber semi-permeable membranes. The excess fluid may pass through the membrane and fill the exterior flow chamber. In some embodiments, the volume of the biosample fluid comprising cells introduced into the device may be about 20× to 300×greater than the collective volume of all interior flow chambers of the device, for example, about 20×, 40×, 60×, 80×, 100×, 200×, or 300×greater than the collective volume of the interior flow chambers.

The methods disclosed herein may comprise introducing the cells and the particles substantially simultaneously. For instance, the methods may comprise combining the cells and the particles to form a mixed sample before introducing the cells and the particles into the device. In some embodiments, the cells and particles may be maintained in contact for a period of time before being introduced into the device. In some embodiments, the cells and particles may be agitated, for example, with a mixer, before being introduced into the device. Alternatively, the methods may comprise introducing cells before introducing the particles. The methods may comprise introducing the particles before introducing the cells.

In transduction methods, the method may comprise introducing the cells with the virus, loading the cells into the device first and then loading the virus, or loading the virus into the device first and then loading the cells. Similarly, in activation methods, the method may comprise introducing the cells with the activation particles, loading the cells into the device first and then loading the activation particles, or loading the activation into the device first and then loading the cells. Alternatively, in certain embodiments of activation methods, the method may comprise introducing the cells into the device to contact surface bound activation particles. In some embodiments, the methods may comprise coating the membrane with the activation particles prior to introducing the cells. For example, the methods may comprise introducing a treatment agent comprising activation particles capable of binding the membrane. Alternatively, the methods may comprise introducing a priming fluid comprising activation particles capable of binding the membrane at the time of priming.

In certain embodiments, the method may comprise performing an activation and transduction in the same device. Thus, the method may comprise introducing the cells into the device before loading the activation particles or virus. The activation particles and virus may be loaded substantially simultaneously. The activation may be performed before or after the transduction. The method may comprise one or more washing steps between the cell loading, activation, or transduction steps.

In accordance with certain embodiments, the method may further comprise introducing a media fluid to replenish nutrients, remove waste product, and/or to co-localize the cells and particles to the membrane surface. The media fluid may be introduced after removal of the waste fluid within the device. In some embodiments, the media fluid may be a transduction fluid. The media fluid may be an activation fluid. The media fluid may be cell culture media. The media fluid may be recycled fluid that is circulated from the outlet, for example, the housing outlet, of the device back to the inlet of the device, for example, the luminal inlet or the housing inlet.

The media fluid may be introduced through luminal inlet to wash or otherwise contact the cells and particles. The media fluid flow rate may be altered, or the fluid may be oscillated or pulsed to continue to co-localize the cells and particles within the device. A co-localizing fluid may be introduced to continue to co-localize the cells and particles. Thus, the relative location of cells and particles on the membrane may be altered by continuous or pulsed flow of additional fluid.

Thus, the method may comprise treating the cells for a predetermined amount of time effective to produce the treated cells, for example, transduced or activated cells. The method may comprise maintaining the cells and particles in contact on a surface of the membrane during treatment. During treatment, fluid may be continuously or intermittently introduced into the device. In some embodiments, the conditions within the device are maintained substantially static during treatment, unless a media exchange is being performed. Thus, in some embodiments, the method may comprise maintaining or culturing the cells in the device for a predetermined amount of time.

The predetermined time for treatment or culture may be the prescribed reaction time for the desired reaction. A transduction, for example, may be performed for 90 minutes in a transduction device, disclosed herein. In general, the predetermined time may be up to 24 hour or 48 hours. The predetermined time may be from 30 minutes to 360 minutes, for example, from 60 minutes to 360 minutes, from 60 minutes, to 120 minutes, from 120 minutes to 180 minutes, or 30 minutes, 60 minutes, 90 minutes, 120 minutes, 150 minutes, 180 minutes, 240 minutes, 360 minutes or more. The predetermined time may be 1 hour, 2 hours, 3 hours, 4 hours, 5 hours, 6 hours, 7 hours, 8 hours, or more. For certain reactions, for example, performed for longer than 6 hours, the method may comprise removing waste and introducing nutrients to maintain cell viability. The reaction may take place at a controlled temperature. Thus, in some embodiments, the method may comprise measuring temperature and/or heating or cooling the device to control temperature. In some embodiments, the method may further comprise introducing an oxygen containing gas into the treatment device. An effective amount of an oxygen containing gas may be introduced to maintain cell viability.

Following the reaction, the method may comprise introducing a recovery fluid (also referred to as a "media fluid" herein) into the device along the lumen side of the hollow fiber semi-permeable membrane. The recovery fluid may be introduced to suspend the treated cells in an intermediate sample. The recovery fluid may be introduced in the same direction as loading of the cells and/or particles or in the opposite direction. To assist with cell recovery, the method may comprise introducing a releasing fluid (also referred to as a "media fluid" herein) into the treatment device against the surface side of the semi-permeable membrane to release the transduced cells and the particles from the membrane surface. The recovery fluid and the releasing fluid may be introduced substantially simultaneously or sequentially. For example, in some embodiments, at least a portion of the recovery fluid may be introduced substantially as at least a portion of the releasing fluid. The recovery fluid and releasing fluid may produce a treated cell sample comprising the treated cells and, optionally, the particles. The method may comprise discharging the treated cell sample from the treatment device. The treated cell sample may be discharged through the luminal inlet or through the luminal outlet.

In particular, while not wishing to be bound by any particular theory, it has been observed that the combination of providing a recovery fluid along the lumen side of the membrane and providing a releasing fluid against the surface side of the membrane has a synergistic effect in recovery of cells from the device, as compared to each flow profile alone.

Fluid flow rate may be selected to provide an optimized recovery rate of cells from the device. In particular, flow rate of the recovery fluid and/or releasing fluid may be selected to control the wall shear stress on the lumen side of the semi-permeable membrane. In some embodiments, the loading flow rate is greater than the recovery flow rate. In some embodiments, the recovery flow rate is greater than the loading flow rate. The recover flow rate may be controlled to provide a greater wall shear stress than the loading flow rate, i.e., the flow rate of introducing one or both of the biosample and the treatment agent into the device.

In some embodiments, the recovery flow rate and/or releasing flow rate may be selected to control or maintain an average wall shear stress on the first side of the semi-permeable membrane between about 0.05 Pa and 10 Pa. For example, the flow rate may be selected to maintain an average wall shear stress of between about 1.0 Pa and about 10 Pa, or between about 3.0 Pa and 10 Pa. As previously discussed, recovery of cells can be increased by maintaining a desired average wall shear stress.

The recovery flow rate may be scaled with hollow fiber membrane size (for example, diameter) and number of hollow fiber membranes in the device, to provide adequate recovery of the cells and particles. The recovery flow rate may be between about 1.0 ml/min/cm$^2$ and about 2.5 ml/min/cm$^2$ surface area of each hollow fiber semi-permeable membrane, for an exemplary hollow fiber membrane having a diameter of about 0.5 mm. In some embodiments, the recovery flow rate may be about 1.0 ml/min/cm$^2$, about 1.5 ml/min/cm$^2$, about 2.0 ml/min/cm$^2$, or about 2.5 ml/min/cm$^2$ surface area of each hollow fiber semi-permeable membrane.

In some embodiments, a recovery flow rate of between about 1 ml/min and about 20 ml/min per hollow fiber membrane may improve recovery of cells and/or particles from the device. In some embodiments, for example, for a device having a plurality of hollow fiber membranes, the device may operate during recovery of cells at a flow rate of about 50 ml/min and up to about 600 ml/min, scaling with number of hollow fiber membranes.

In some embodiments, the recovery fluid flow rate may be greater than the releasing fluid flow rate. In some embodiments, the releasing fluid flow rate may be greater than the recovery fluid flow rate. In some embodiments, a ratio of the releasing flow rate to the recovery flow rate may be between 1:1 and 1:50. The ratio of flow rates may be about 1:1, about 1:10, about 1:25, about 1:40, or about 1:50.

The releasing flow rate may similarly be scaled with hollow fiber membrane size (for example, diameter) and number of hollow fiber membranes in the device. The releasing flow rate may be between about 0.05 ml/min/cm$^2$ and about 2.0 ml/min/cm$^2$ surface area of each hollow fiber semi-permeable membrane. In some embodiments, the releasing fluid flow rate may be between about 0.1 ml/min and about 1.0 ml/min. The releasing fluid flow rate may be about 0.05 ml/min, about 0.1 ml/min, about 0.5 ml/min, about 1.0 ml/min, or about 2.0 ml/min. The releasing flow rate may be between about 1.0 ml/min and about 50 ml/min, for example, about 1.0 ml/min-about 25 ml/min, about 5.0 ml/min-about 10.0 ml/min, or about 25 ml/min-about 50 ml/min.

In some embodiments, the recovery fluid and the releasing fluid may originate from the same source, for example, may be obtained from the same source of media fluid. In other embodiments, each of the recovery fluid and the releasing fluid may be obtained from different sources of media fluid. The co-localizing fluid may be obtained from the same or different source as one or both of the recovery fluid and the releasing fluid. Thus, each of the recovery fluid, the releasing fluid, and the co-localizing fluid may be sourced from one or more source of a media fluid. In certain embodiments, the priming fluid may be obtained from the same source as one or more of the recovery fluid, the releasing fluid, and the co-localizing fluid.

The method may further comprise measuring pressure within the treatment device or a line of the system. The method may comprise controlling a rate of introducing at least one of the biosample fluid, the treatment fluid, the co-localizing fluid, the recovery fluid, and the releasing fluid responsive to the measurement of pressure. For example, the method may comprise controlling the rate of introducing at least one of the biosample fluid, the treatment fluid, the co-localizing fluid, the recovery fluid, and the releasing fluid to maintain a pressure below 500 mmHg or a controlled pressure, as previously described. In some embodiments, pressure may be measured to monitor a rate of protein fouling of the membrane. Pressure may be controlled to enhance viability and/or treatment of the cells within the device.

In some embodiments, the method may comprise introducing a gas into the treatment device to assist with cell recovery. The gas may be introduced substantially simultaneously or sequentially with the recovery fluid and/or the releasing fluid. The gas may be a biocompatible gas, or otherwise a non-toxic gas to the cells.

In some embodiments, the method may comprise oscillating flow rate of at least one of the recovery fluid and the releasing fluid to assist with cell recovery.

Thus, after a given reaction or incubation time, the treated sample fluid comprising cells and particles can be released from the interior flow chamber of the hollow fiber membrane, optionally by changing the flow direction. The method may comprise separating treated cells from particles in the fluid. The treated sample fluid can be removed from the flow chamber and processed to remove the remaining unreacted particles with standard methods such as centrifugal pelleting of cells and removal of the excess fluid, or the fluid can be directed to a separation device. The separation device may contain a membrane that is permeable to the particles but impermeable to the cells. The separation device may be used to wash the cells of unreacted particles, cell waste, and byproducts by passing a volume of media through the device.

In some embodiments, the separation may be performed by conventional methods, for example, centrifugation or conventional membrane filtration. In some embodiments, the separation may be performed in a separation device, as disclosed herein. Accordingly, the method may comprise introducing the treated cell sample with the cells and the particles into the separation device to contact the semi-permeable membrane having a plurality of pores dimensioned to allow passage of the fluid and the particles and prevent passage of the cells. Additional wash steps may be performed as necessary to ensure proper separation of the cells from the particles and any other undesired constituents. The method may further comprise discharging the fluid and the particles through an outlet, such as the housing outlet. Recovery of the cells that remain on the membrane may be performed as previously described herein.

The methods disclosed herein may produce a therapeutically acceptable product, for example, a finished therapeutic product. In some embodiments, the method may further comprise introducing the treated cells into a recipient subject. The treated cells may be activated or transduced cells. The recovered cells may be purified and suspended in a physiological acceptable media to produce the therapeutically acceptable product. Additional therapeutic agents may be combined with the therapeutically acceptable product.

In some embodiments, the method may further comprise obtaining the cells from a donor subject. The treated cells may be autologous, allogeneic, or xenogeneic. Thus, in some embodiments, the recipient subject is the same as the donor subject. In other embodiments, the recipient subject and the donor subject are different from one another.

In some embodiments, the method may comprise introducing a second amount of the treatment fluid with a second amount of particles into the treatment device. In some embodiments, the method may further comprise introducing a second treatment fluid with a second type of particles into the treatment device. Thus, in some embodiments, the method may comprise introducing a second dose or amount of particles into the interior flow chamber of each hollow fiber membrane. The second dose of particles may be the same particles or different particles from the first dose. In some embodiments, the particles are viral particles configured to perform a different transduction. The particles may be activation particles. For instance, in some embodiments, the first dose of particles may be activation particles. After activation of the cells, the second dose of particles may be viral particles. In other embodiments, each of the first dose and the second dose may be the same type of particle. The particles may be provided to provide a boosting dose to the cells, for example, to increase transduction efficiency or activation of the cells. In addition to transduction of cells by viral particles, as previously described, other treatment methods are envisaged. For instance, activation is another treatment for cells that may be performed with the systems and methods disclosed herein. Referring specifically to the exemplary treatment of T cells, the devices and methods may be used to activate the T-cells with antibodies, such as anti-CD3 and anti-CD28 antibodies, optionally coated on micro-beads or nano-beads. In certain embodiments, the membrane surface may be modified or functionalized with membrane surface bound antibodies, such as anti-CD3 anti-CD28 antibodies.

In another embodiment, the systems and methods disclosed herein may be employed for separation of subpopulations of cells from a mixed population of cells. For instance, the particles may comprise affinity particles selected to bind a target cell type. The membrane may have pores dimensioned to allow passage of unbound cells and retain cells bound to affinity particles. The unbound cells may be discharged from the device through an outlet, such as a housing outlet. The cells bound to affinity particles may be recovered, as previously described. In some embodiments, the membrane surface may be modified or functionalized with affinity particles selected to bind a target cell type. Exemplary target cell types include stem cells, immune cells, cancer cells, engineered cells, primary cells, T-cells, primary T-cells, regulatory T-cells, NK cells, B cells, and hematopoietic stem cells (HSC). The systems and methods may be used to separate subclasses of cells, for example, subclasses of T-cells, such as CD3, CD4, CD8, or CD25 positive T-cells.

In certain embodiments, the systems and methods disclosed herein may be employed for maintenance and/or expansion of the cells through the perfusion of fresh media into the system and removal of used media. Thus, the device may be used to perform a wash and media change of the cells.

In certain embodiment, the systems and methods disclosed herein may be employed to exchange the biosample and/or treatment fluid by transmembrane flow of a media fluid and subsequent recovery of waste fluid from the device using the techniques described above for cell recovery.

In some embodiments, the application of flow in relevant ranges or use of buffer with different tonicity or pH may be employed to impart changes to the cells through mechanical forces and mechanotransduction pathways. For instance, the cells may be treated to increase susceptibility to uptake of genetic material.

It should be understood that the different embodiments and treatment methods described herein may be combined to achieve a multitude of process steps. The combined effect may be achieved in a single device or a number of separate but interconnected devices, each appropriately configured for the desired application.

Any of the previously described methods may be performed in the devices disclosed herein. Additionally, the devices disclosed herein may be used to perform other reactions not contemplated.

EXAMPLES

Example 1: Distribution of Cells and Particles on the Semi-Permeable Membrane for Various Loading Schemes Different loading protocols have been simulated by varying loading density and distribution of cells and particles in a hollow-fiber semi-permeable device. FIGS. 9A-9C, 10A-10C, and 11A-11C include schematic diagrams showing a cross-section of the hollow fiber membrane 120 having loaded cells 10 and particles 20 in accordance with the different simulated protocols.

Figure 9A:
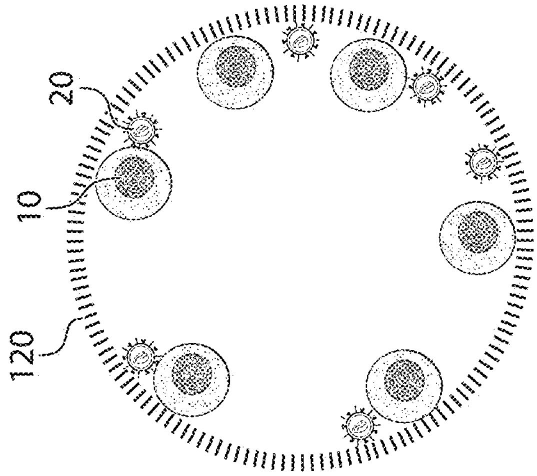
FIGS. 9A-9C are cross-sectional views of a hollow fiber membrane having cells and particles against a lumen side of the membrane, according to one embodiment.
Figure 9B:
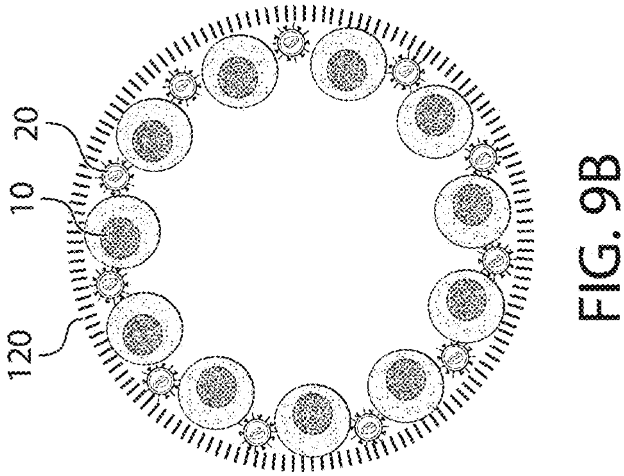
Figure 9C:
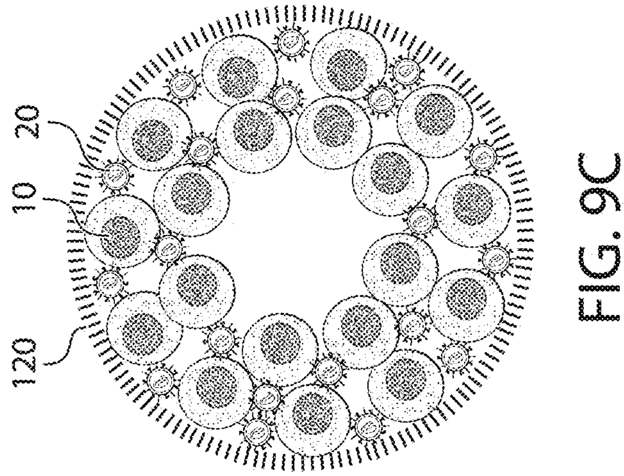

Simultaneous delivery of cells 10 and particles 20 in a mixed sample produced before introduction of the mixed sample into the device is shown in FIGS. 9A-9C. The dependance of efficiency of co-localization and interaction kinetics between cells 10 and the particles 20 is compared in the several diagrams of FIGS. 9A-9C. Sub-confluent (low cell surface density) loading of the cells 10 and particles 20 is shown in FIG. 9A. As shown in the diagram of FIG. 9A, low cell density loading could lead to inefficient co-localization of the cells 10 and particles 20, due to unpopulated areas by cells. Confluent (intermediate cell surface density) loading of the cells 10 and particles 20 is shown in FIG. 9B. The cell loading rate of FIG. 9B is effective to produce a monolayer of cells 10 on the membrane 120. Over-confluent (high cell surface density) loading of the cells 10 and particles 20 is shown in FIG. 9C. As shown in FIG. 9C, enhanced interaction between cells 10 and particles 20 is produced as a result of the multilayer of cells 10. It is hypothesized that over-confluent loading of cells 10 may sufficiently entrap particles 20 between cell layers, preventing diffusion of the particles 20 and enhancing contact in the inner cell layers. Improved transduction efficiency is expected by introducing a mixed fluid having cells and particles. In particular, improved transduction efficiency is expected by introducing the mixed fluid into the device at a high cell loading rate to produce a multilayer of cells on the membrane surface.

Figure 10C:
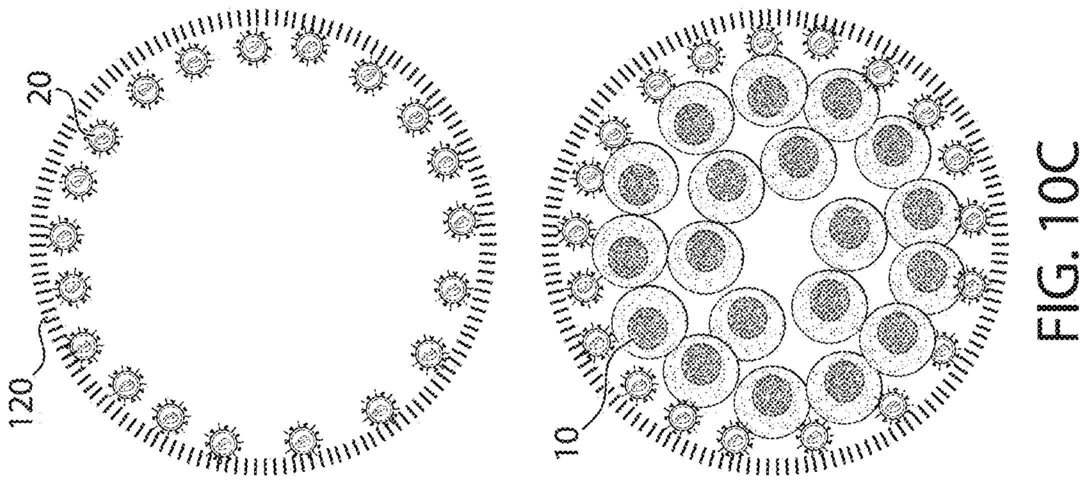
FIGS. 10A-10C are cross-sectional views of a hollow fiber membrane having particles or cells and particles against a lumen side of the membrane, according to another embodiment.
Figure 10B:
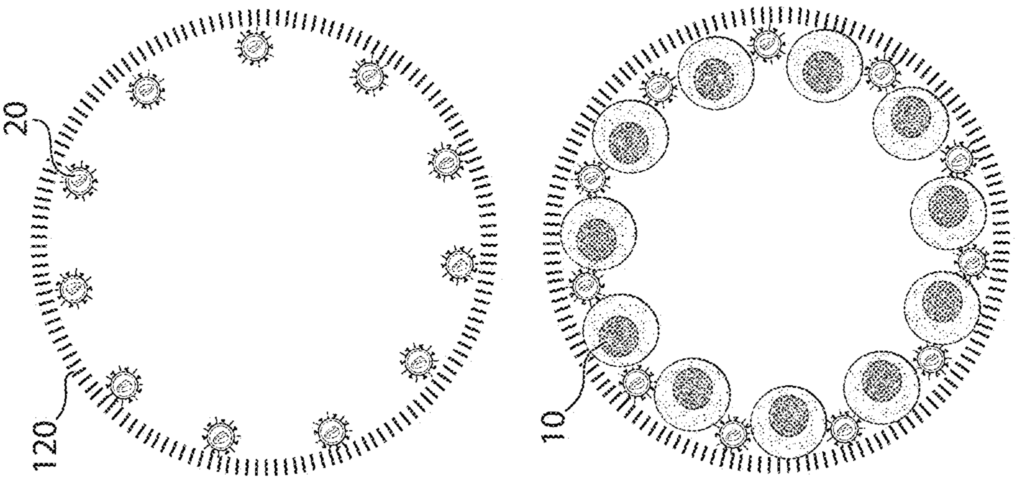
Figure 10A:
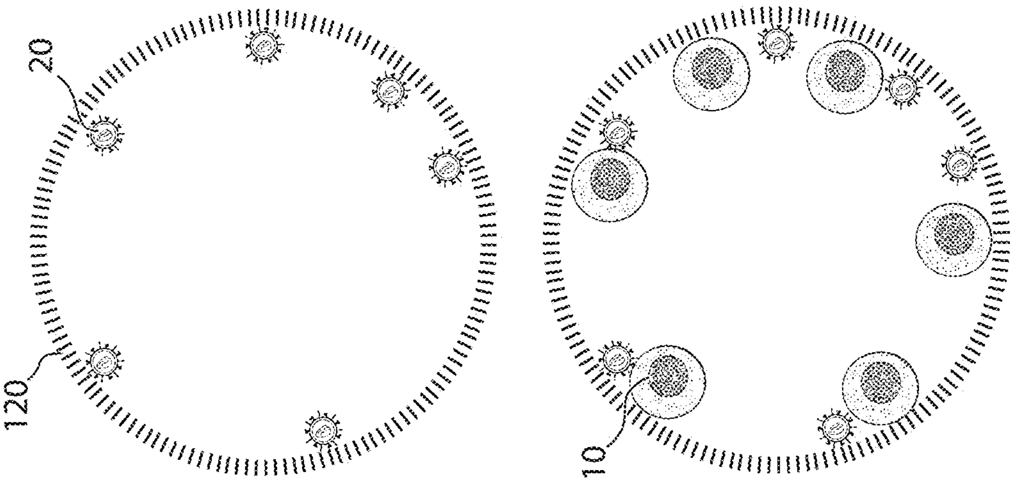

Sequential delivery of particles 20 before cells 10 into the device is shown in the two-step schematic diagrams of FIGS. 10A-10C. Sub-confluent (low cell surface density) loading of the cells 10 into the device comprising particles 20 is shown in FIG. 10A. As shown in the diagram of FIG. 10A, low cell density loading could lead to inefficient co-localization of the cells 10 and particles 20, due to unpopulated areas by cells. Confluent (intermediate cell surface density) loading of the cells 10 into the device comprising particles 20 is shown in FIG. 10B. The cell loading rate of FIG. 10B is effective to produce a monolayer of cells 10 on the membrane 120. Over-confluent (high cell surface density) loading of the cells 10 into the device comprising particles 20 is shown in FIG. 10C. As shown in FIG. 10B, a monolayer of cells 10 and particles 20 may provide efficient interaction between the cells 10 and particles 20 when particles 20 are loaded before cells 10. Furthermore, as shown in FIG. 10C, high cell loading rate is not desirable when particles 20 are loaded before cells 10 because the particles 20 against the surface of the membrane 10 are not accessible to some multilayer cells 10.

It is hypothesized that the delivery of particles 20 before cells 10 is beneficial when the treatment agent sample is unpurified, for example, when the treatment agent sample comprises inhibitory factors. In such embodiments, inhibitory factors may be removed from within the membrane before introducing the biosample comprising cells.

Figure 11A:
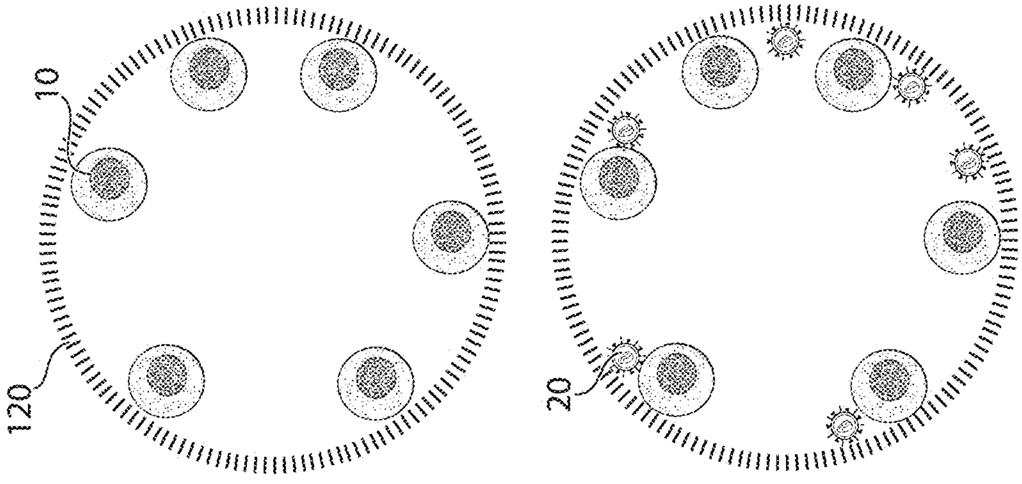
FIGS. 11A-11C are cross-sectional views of a hollow fiber membrane having cells or cells and particles against a lumen side of the membrane, according to another embodiment.
Figure 11B:
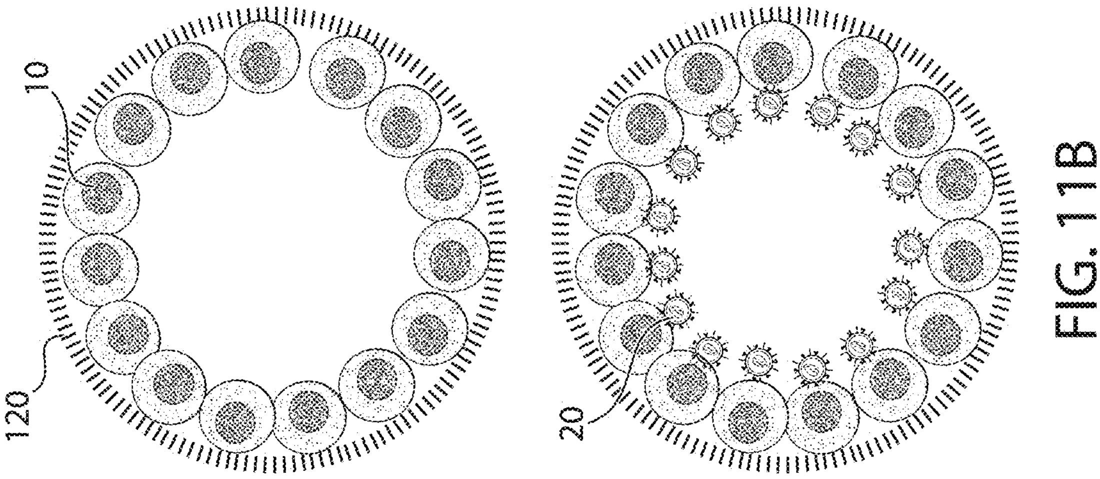
Figure 11C:
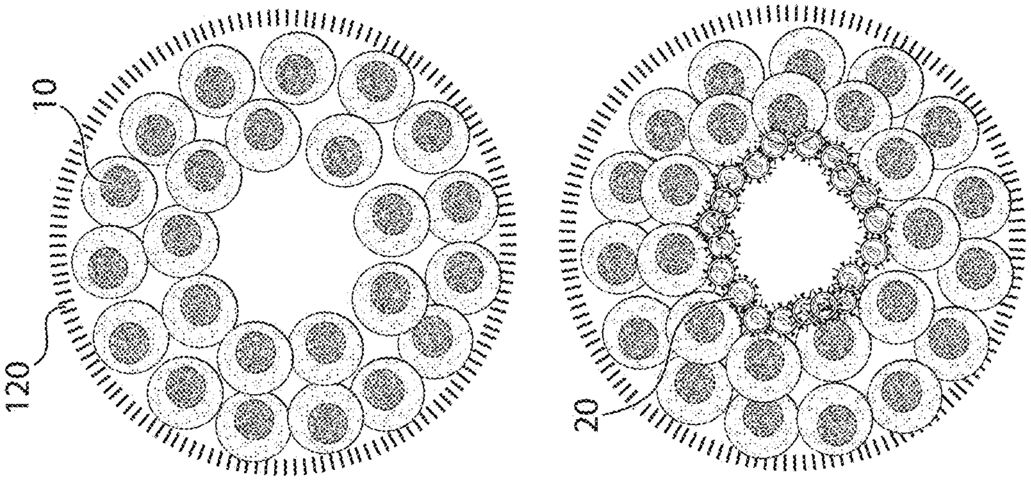

Sequential delivery of cells 10 before particles 20 into the device is shown in the two-step schematic diagrams of FIGS. 11A-11C. Sub-confluent (low cell surface density) loading of the cells 10 into the device followed by particles 20 is shown in FIG. 11A. As shown in the diagram of FIG. 11A, low cell density loading could lead to inefficient co-localization of the cells 10 and particles 20, due to unpopulated areas by cells. Confluent (intermediate cell surface density) loading of the cells 10 into the device followed by particles 20 is shown in FIG. 11B. The cell loading rate of FIG. 11B is effective to produce a monolayer of cells 10 on the membrane 120. The subsequent delivery of particles 20 may be blocked from accessing the membrane 120 by the larger cells 10. Over-confluent (high cell surface density) loading of the cells 10 into the device followed by particles 20 is shown in FIG. 11C. As shown in FIG. 11B, a monolayer of cells 10 followed by particles 20 may provide efficient interaction between the cells 10 and particles 20 when cells 10 are loaded before particles 20. Furthermore, as shown in FIG. 11C, high cell loading rate is not desirable when cells 10 are loaded before particles 20 because the particles 20 are not accessible to some multilayer cells 10.

The impact of delivery sequence on transduction efficiency was measured. In one sample, cells were combined with LVV viral vector prior to being introduced into the device. In another sample, cells were introduced into the device before the LVV viral vector was introduced. After a period of transduction, the transduction efficiency of each of the samples was measured and compared to a static transduction control. The results are shown in the graph of FIG. 12.

Figure 12:
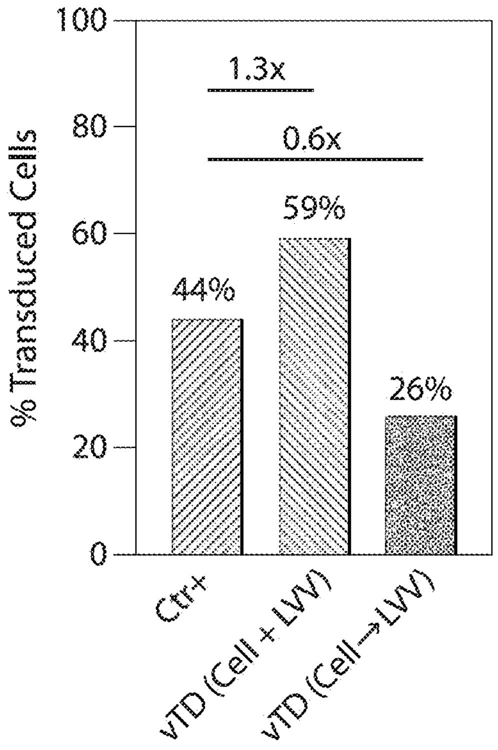
FIG. 12 is a graph showing percentage of transduced cells for several delivery sequences of cells and particles, according to one embodiment.

As shown in FIG. 12, transduction efficiency of the cells introduced before the viral vector was 0.6× of the control, while transduction efficiency of the mixed sample was 1.3× of the control sample. Accordingly, simultaneous delivery of a mixed sample comprising cells and virus produces a more efficient transduction than sequential delivery of cells before virus. It is hypothesized, however, that unpurified viral samples may produce a more efficient transduction when introduced and washed (to remove inhibitory factors) before introduction of cells, as compared to delivery of a mixed sample having cells and unpurified virus.

Example 2: Effect of Oscillatory Flow on Transduction Efficiency

Oscillatory flow of the biosample, treatment agent, and/or co-localizing fluid may be provided during loading of the cells, particles, or both, and/or during co-localization of the cells and particles on the membrane. FIG. 13A is a graph depicting change in flow rate over time that produces an oscillatory flow.

The effect of oscillatory flow on transduction efficiency was measured. To provide the oscillatory flow, cells and viral particles were introduced into the device using a peristaltic pump. The oscillatory flow continued to co-localize the cells and the virus on the membrane during transduction. A comparative sample of cells and viral particles was introduced into the device using a syringe pump, which provides a negligible oscillatory flow component. No oscillatory flow was provided to the comparative sample during transduction. The transduction efficiency of the oscillatory flow sample and comparative sample was measured and compared to a static transduction control. The results are shown in the graph of FIG. 13B.

As shown in FIG. 13B, transduction efficiency of the syringe pump sample was 1.5× of the control, while transduction efficiency of the sample introduced and co-localized with an oscillatory flow was 1.9× of the control. Accordingly, loading and transduction with an oscillatory flow produces a more efficient transduction than loading and transduction with a syringe pump. Without wishing to be bound by theory, it is believed the improved transduction efficiency is a result of improved mixing and interaction kinetics between the cells and virus provided by the oscillatory flow of media. Thus, it is believed that an oscillatory flow of media may improve transduction efficiency.

Example 3: Delivery of Cells and Virus Through a Common Inlet as Compared to Delivery of Cells and Virus Through Opposite Ends of the Device The systems and methods disclosed herein generally include introduction of cells and particles through an inlet of a treatment device. Specifically, the cells and particles are introduced on the same end of the device, optionally though the same inlet. Delivery of cells and particles through the same inlet (i.e., on the same end of the device) was simulated and compared to a simulation of delivery of cells and particles through opposite ends of the device. The simulations are shown in the graphs of FIGS. 14A-14D and 15A-15D.

Figure 14A:
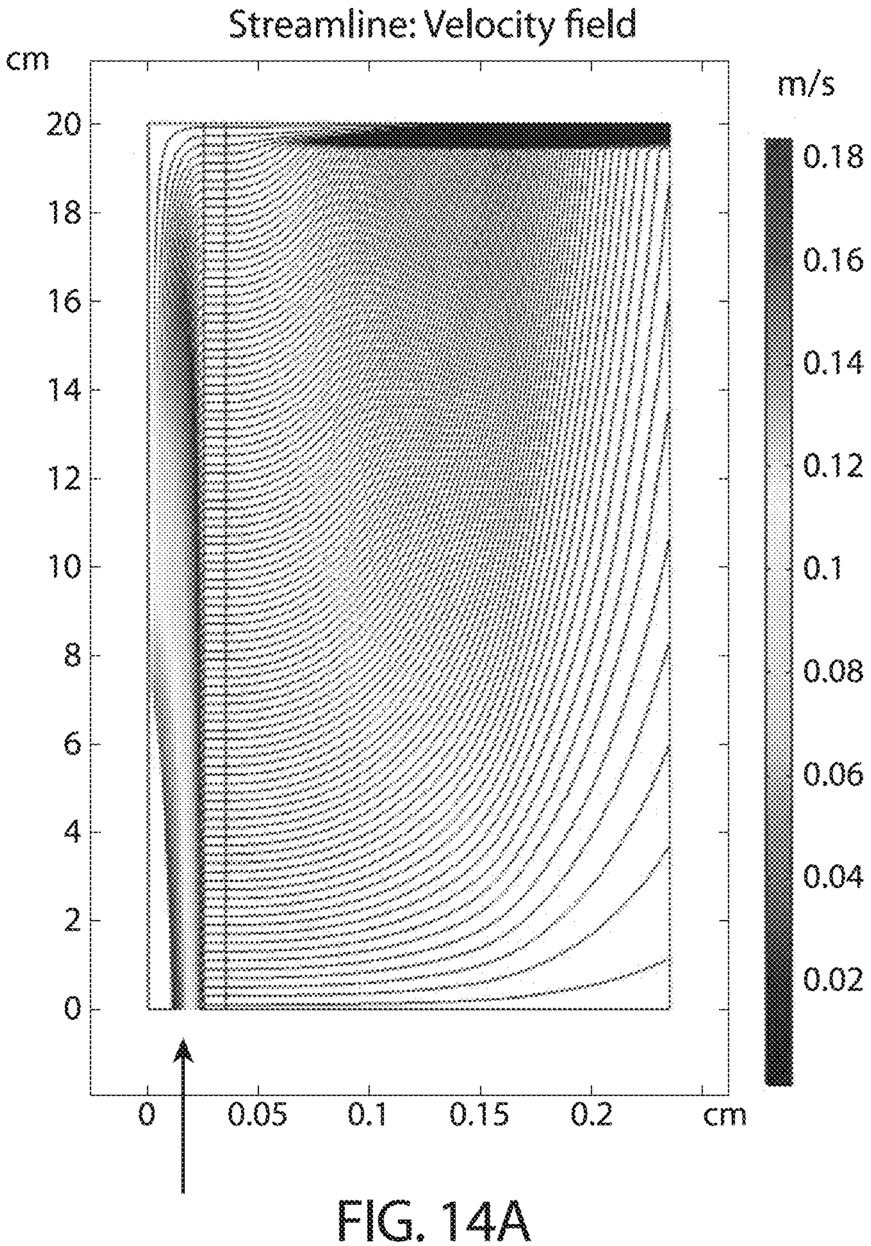
FIGS. 14A-14D are graphs showing velocity field of cells and particles introduced on one end of the device and particle trajectory at different points in time after introduction.
Figure 14B:
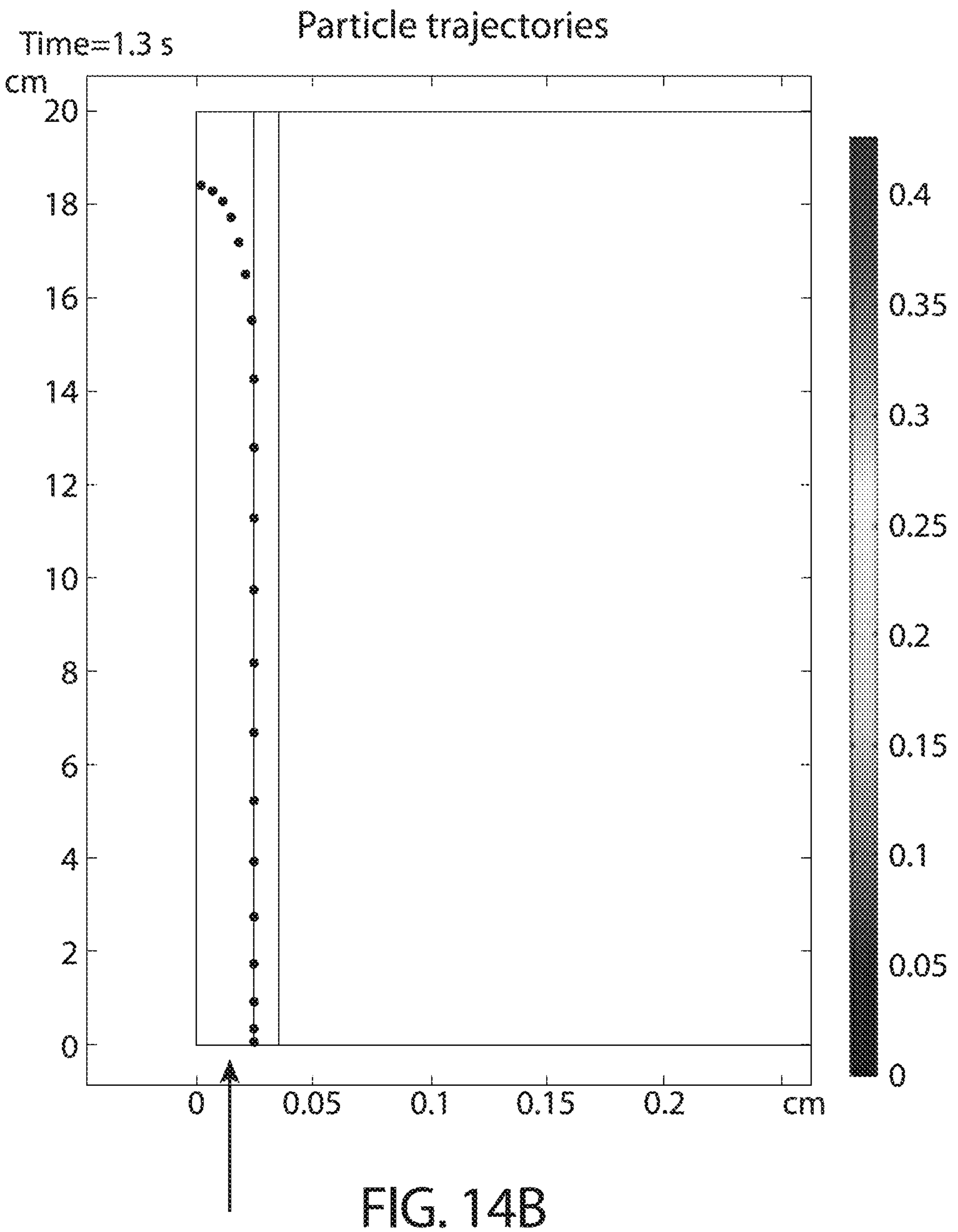
Figure 14C:
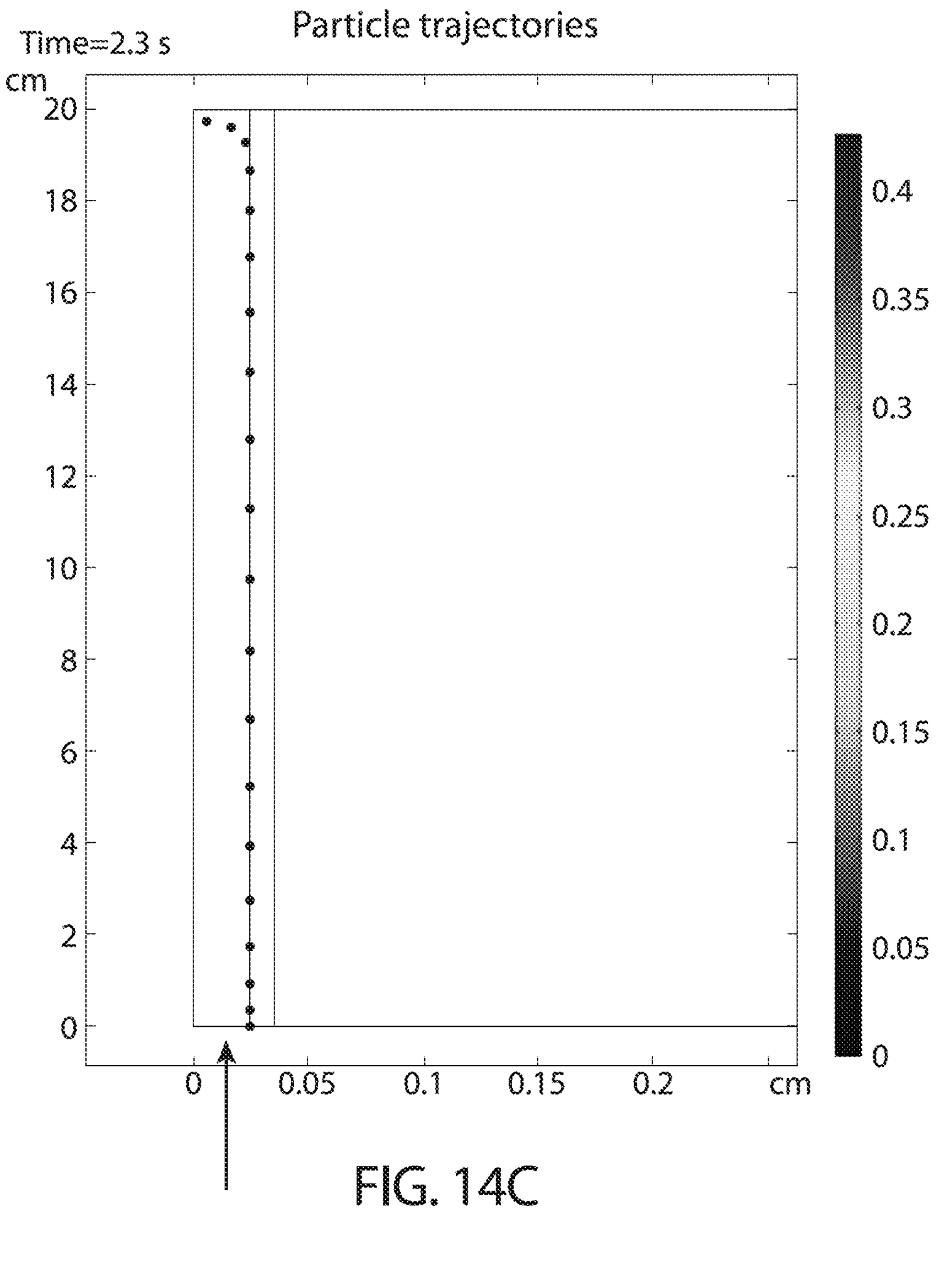
Figure 14D:
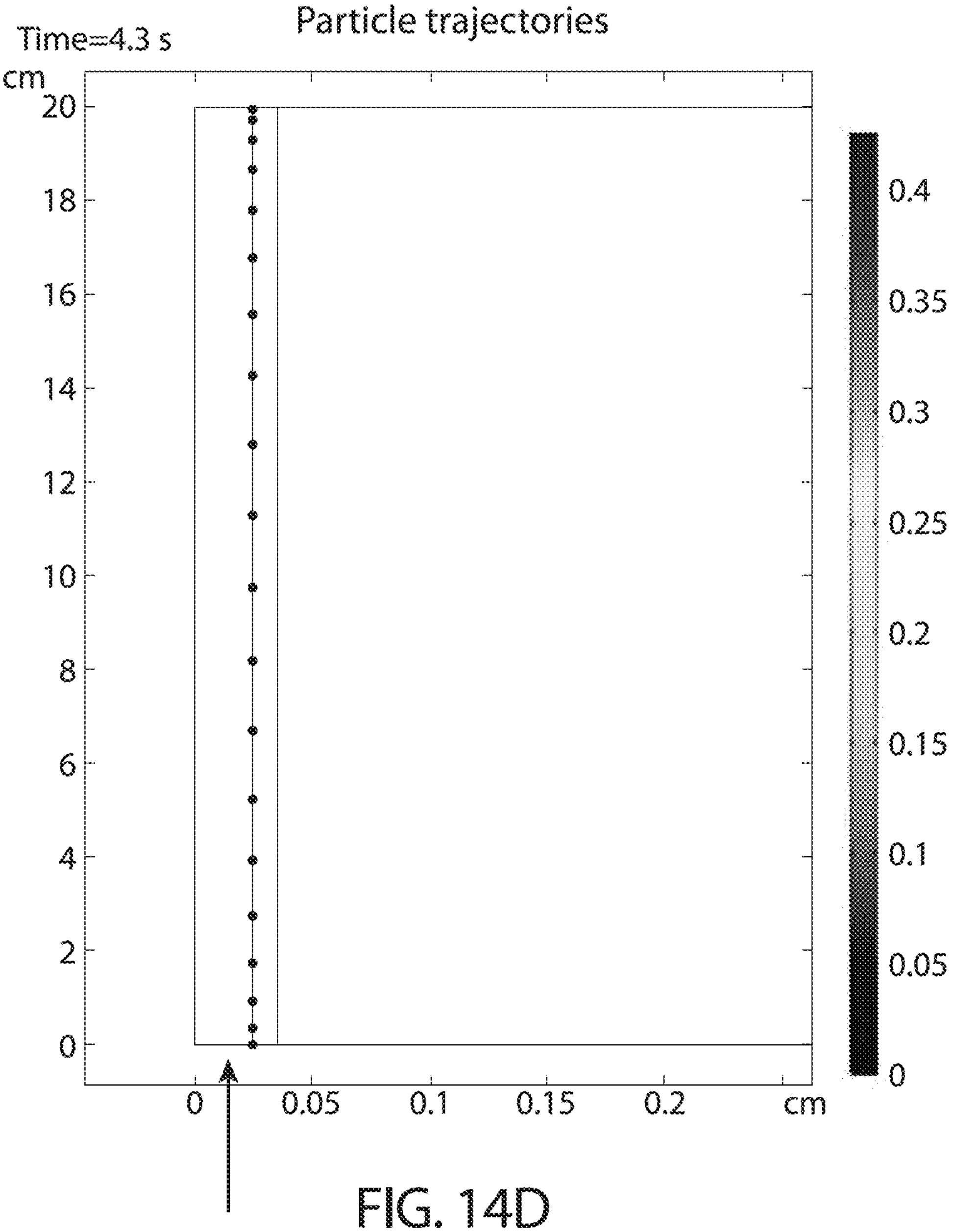

As shown in FIG. 14A, introducing the cells and particles through a luminal inlet on one end of the device results in a substantially uniform distribution of the cells and particles along the membrane. As shown in FIGS. 14B-14D, over time, the cells and particles distribute substantially evenly along the surface of the membrane. This configuration allows efficient simultaneous delivery of the cells and particles, optionally in a mixture, and over-confluent (high loading rate) loading of the device.

Figure 15A:
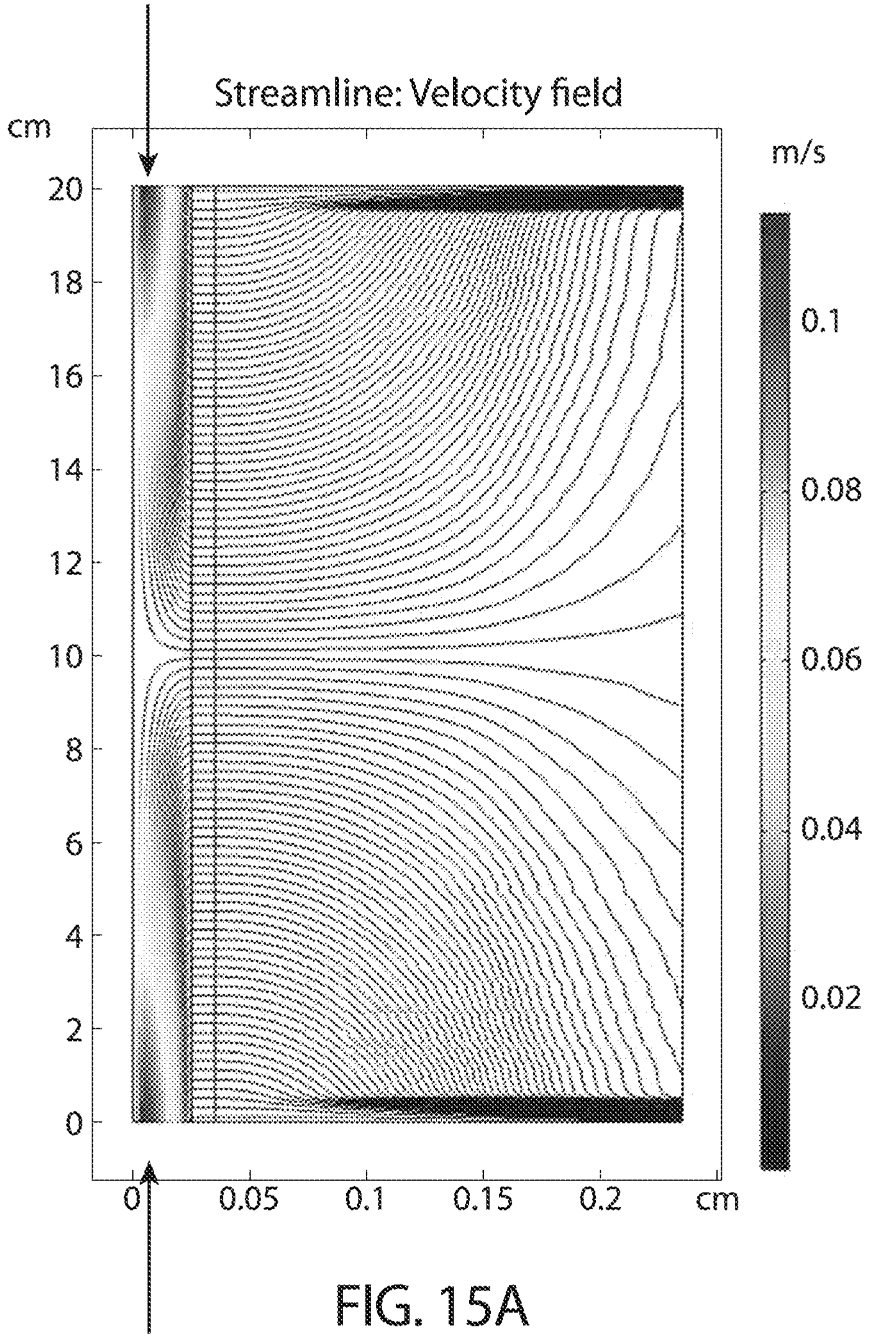
FIGS. 15A-15D are graphs showing velocity field of cells and particles introduced on opposite ends of the device and particle trajectories at different points in time after introduction.
Figure 15B:
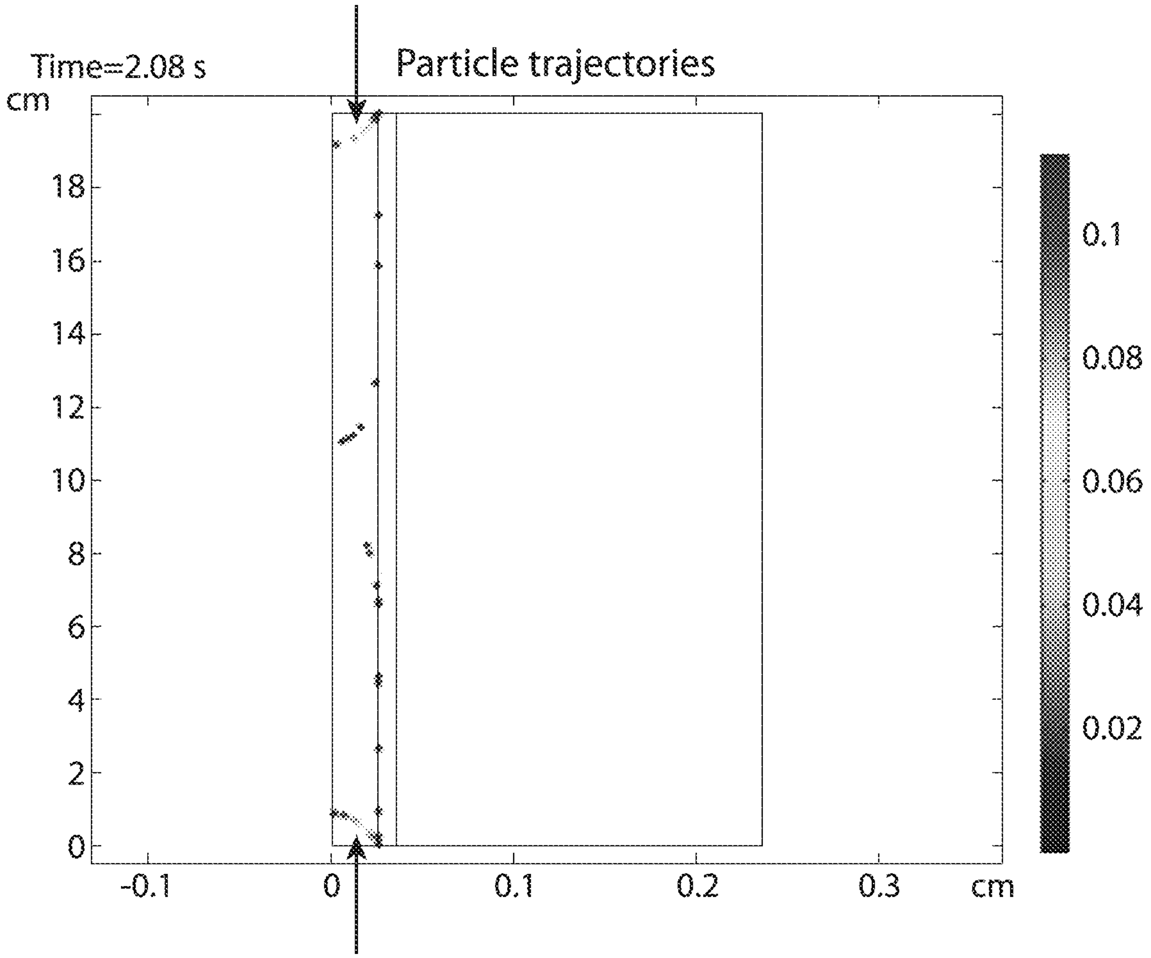
Figure 15C:
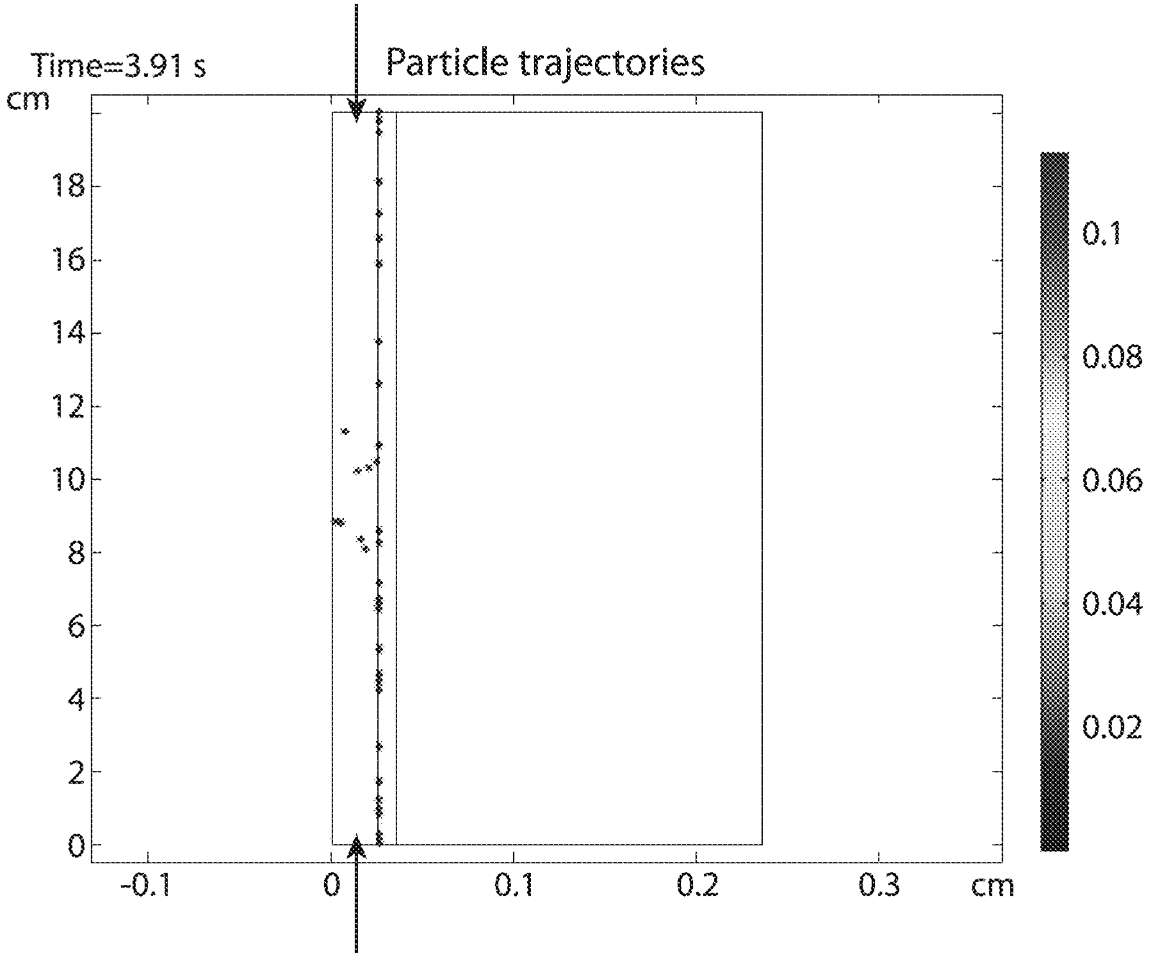
Figure 15D:
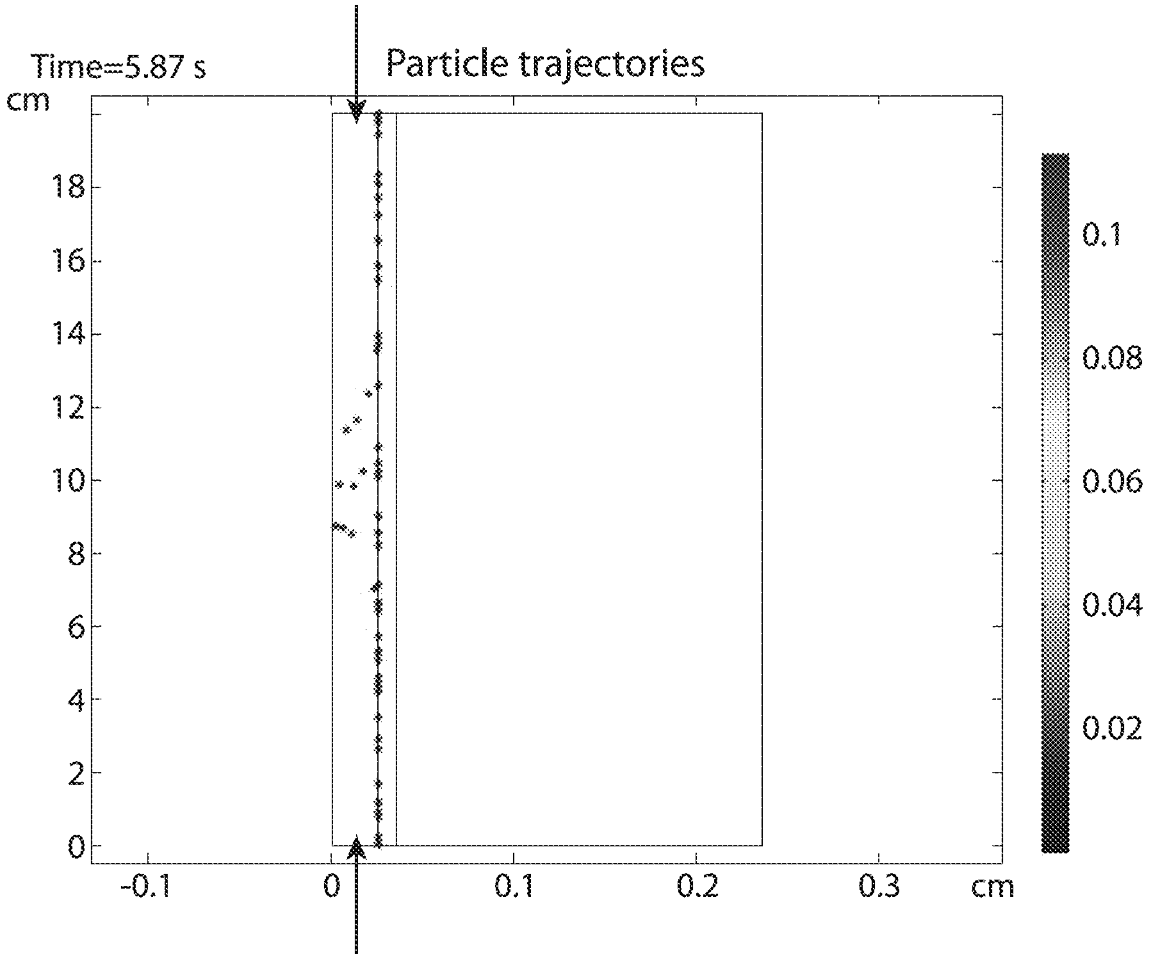

As shown in FIG. 15A, simultaneously introducing the cells and particles through opposite ends of the device results in a distribution profile in which no mixing or co-localization of the cells and particles within the device has occurred. As shown in FIGS. 15B-15D, over time, the cells and particles follow disparate streamlines and do not co-localize. Varying flow rate of one or both of the cell fluid and the particle fluid is expected to shift the flow stagnation point location, and still not produce substantial co-localization of the cells and particles.

Accordingly, a system having delivery of cells and particles on a same end of the device is superior to a system having delivery of cells and particles on opposite ends of the device, in particular when introducing cells and particles simultaneously.

Example 4: Loading Ratio

The systems disclosed herein may accommodate different loading ratios of cell to particle, for example, 0.25 to 2, 0.25 to 4, 0.25 to 10, or more (defined as number of cells/number of particles).

Samples of cells and virus having varying loading ratios of 1 and 2 were introduced into the device and co-localized on the membrane for a transduction period of 90 minutes. Transduction efficiency of the transduced samples was measured using flow cytometry and a custom secondary antibody. The samples were compared to static transduction control samples having loading ratios of 0.5, 1, 2, 4 which were transduced overnight. The results are shown in the graphs of FIGS. 19A-19B.

Figure 19A:
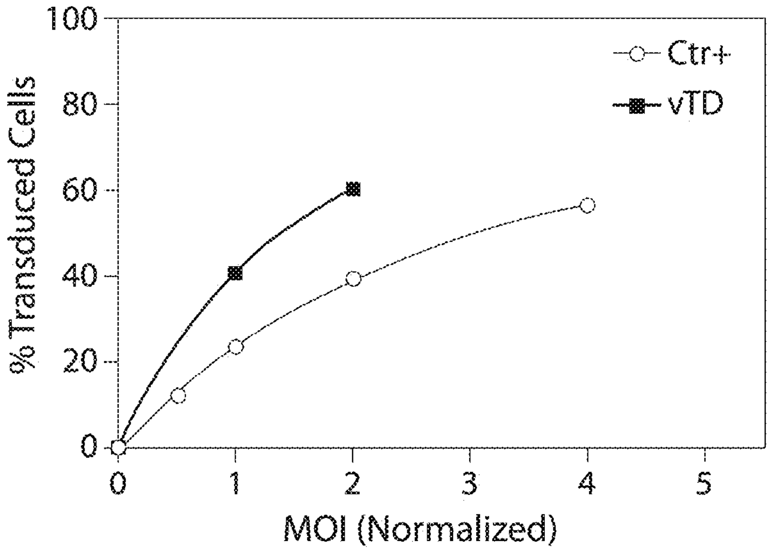
FIGS. 19A-19B are graphs showing transduction efficiency of cells treated at various cell to virus loading ratios, according to certain embodiments.
Figure 19B:
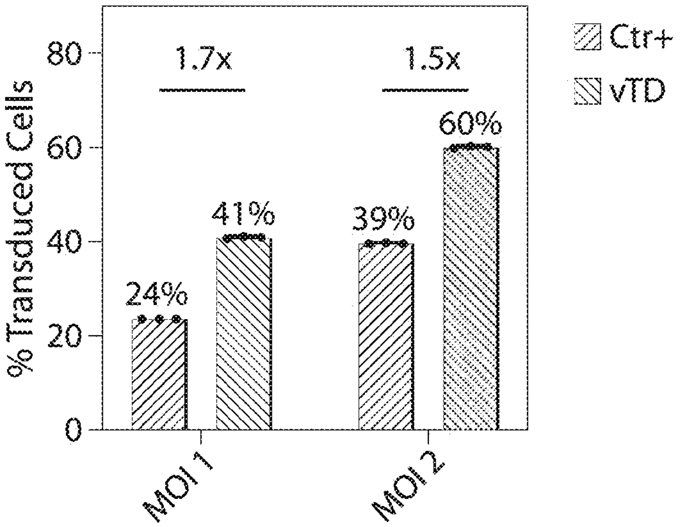

As shown in FIG. 19A, the experimental sample having a loading ratio of 2 after a 90 minute transduction in the device had a transduction efficiency similar to the overnight static control sample having a loading ratio of 4. As shown in FIG. 19B, the experimental samples had a transduction efficiency of 1.7× and 1.5× of the control for the same loading ratio.

Accordingly, the methods and devices disclosed herein perform a superior transduction in less time than static controls.

Example 5: Transduction Efficiency Post-Activation

The systems and methods disclosed herein may accommodate transduction of cells at several days post-activation, for example, 1-3 days post-activation or more.

Samples of cells at 1 day and 3 days post-activation were transduced with lentivirus in the devices disclosed herein at a loading ratio of 1, and compared to 1 day and 3 day post-activation static transduction control samples at loading ratios of 0.5, 1, 2, and 4. The transduction efficiency results are shown in the graphs of FIGS. 20A-20B.

Figure 20A:
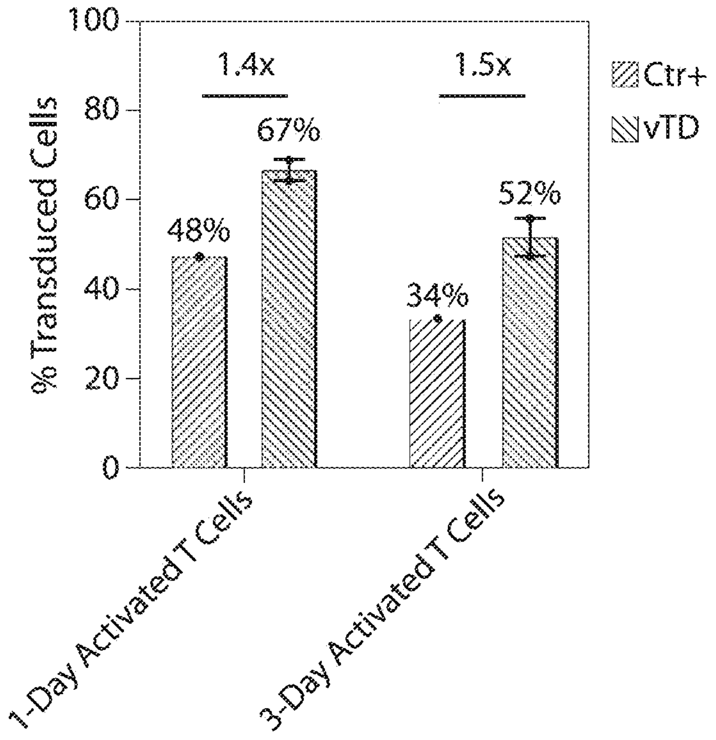
FIG. 20A is a graph showing transduction efficiency of cells at different days post-activation, according to certain embodiments.
Figure 20B:
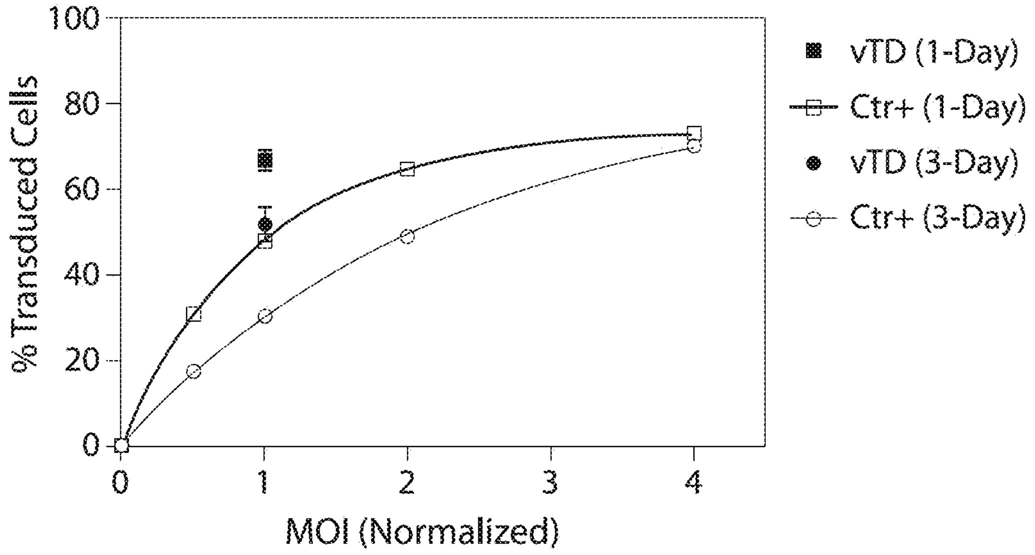
FIG. 20B is a graph showing transduction efficiency of cells treated at various cell to virus loading ratios at different days post-activation, according to certain embodiments.

As shown in the graph of FIG. 20A, the experimental samples had a transduction efficiency of 1.4× and 1.5× of the control for the same number of days post-activation. As shown in the graph of FIG. 20B, the experimental samples had a greater transduction efficiency than the comparative controls for the same loading ratio and a comparable transduction efficiency to the comparative controls having a loading ratio of 4, which is 4 times greater than the experimental loading ratio.

Accordingly, the methods and devices disclosed herein perform a superior transduction of cells at one or more days post-activation than static controls. Furthermore, the methods and devices disclosed herein may be used with significantly less viral particles to obtain a superior or equivalent transduction.

Example 6: Cell Surface Density

The systems and methods disclosed herein may accommodate a variety of cell surface densities. Cell surface density is generally selected responsive to the size of the cells and the desired loading ratio.

Activated T cells were transduced with lentiviral particles in the devices disclosed herein at cell surface densities of $1\times10^6$, $1.5\times10^6$, and $2.0\times10^6$ cells/cm$^2$ and compared to static transduction controls. The results are shown in the graph of FIG. 21.

Figure 21:
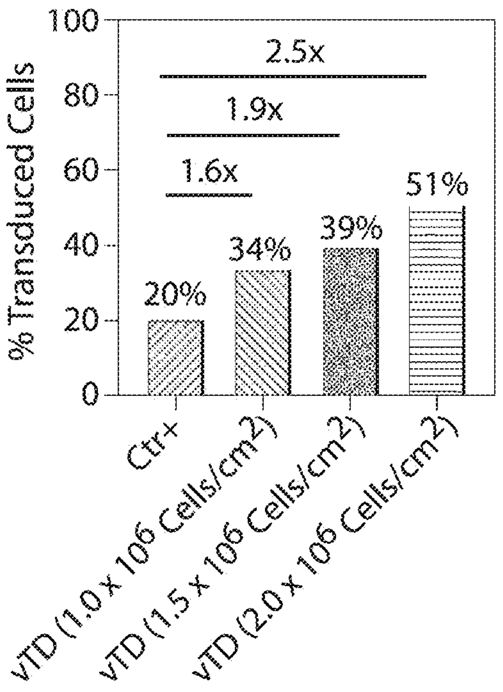
FIG. 21 is a graph showing transduction efficiency of cells treated at different cell surface densities, according to certain embodiments.

As shown in FIG. 21, the experimental samples had a transduction efficiency of 1.6×, 1.9×, and 2.5×, respectively, of the control sample. Accordingly, transduction within the device is successful at increasing cell surface densities. It is believed, however, that there is an optimal cell surface density beyond which transduction efficiency would not continue to increase.

Example 7: Co-Localization Fluid Flow Rate

Cells were transduced with viral particles in the device at varying co-localization fluid flow rates of 0 μL/min/cm$^2$, 4 μL/min/cm$^2$, and 8 μL/min/cm$^2$ and compared to static transduction controls. The results are shown in the graph of FIG. 22.

Figure 22:
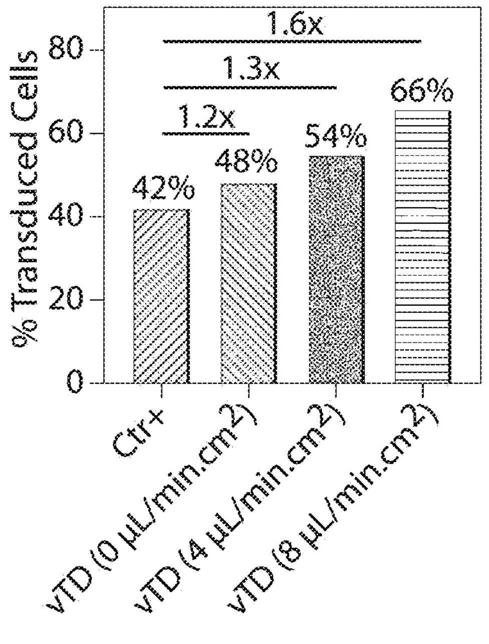
FIG. 22 is a graph showing transduction efficiency of cells treated with different co-localization fluid flow rates, according to certain embodiments.

As shown in FIG. 22, the experimental samples had a transduction efficiency of 1.2×, 1.3×, and 1.6×, respectively, of the control sample. Accordingly, transduction within the device is successful at increasing co-localization fluid flow rates. It is believed, however, that there is an optimal co-localization fluid flow rate beyond which transduction efficiency would not continue to increase.

Example 8: Transduction Time

Cells were transduced with viral particles in the device at a loading ratio of 1 for varying transduction times of 1.5 hrs and 2.5 hrs and compared to static transduction controls having loading ratios of 0.1, 1, 2, and 4. The results are shown in the graphs of FIGS. 23A-23B.

Figure 23A:
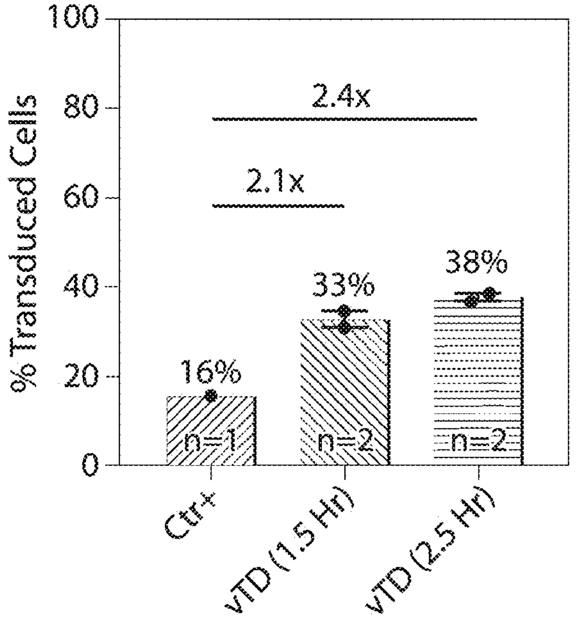
FIGS. 23A-23B are graphs showing transduction efficiency of cells treated with different transduction times, according to certain embodiments.
Figure 23B:
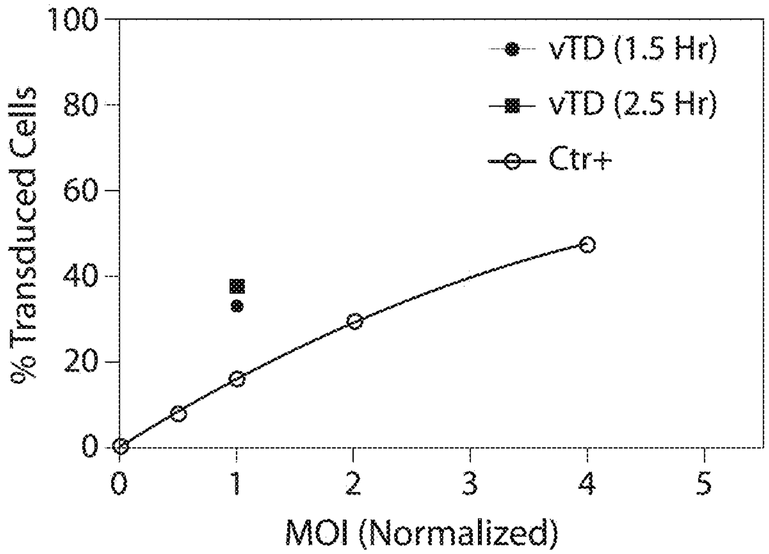

As shown in FIG. 23A, the experimental samples had a transduction efficiency of 2.1× and 2.4×, respectively, of the control sample. As shown in the graph of FIG. 23B, the experimental samples had a superior transduction efficiency than the control samples at the same loading ratio and at a loading ratio of 2.

Accordingly, while increased transduction time in the device produced a greater transduction efficiency, transduction in the device at relatively short transduction times is superior to static controls. While not wishing to be bound by theory, it is believed that the greater transduction time in the device results in a greater transduction efficiency due to increased cell and virus interaction.

Example 9: Membrane Fouling and Concentration Polarization

Membrane fouling and concentration polarization (build-up of foulant at the membrane surface) may reduce device performance. T-cells were transduced with lentivirus in the device at varying flow rates of 0.05 mL/min/cm$^2$, 0.1 mL/min/cm$^2$, and 0.2 mL/min/cm$^2$ and compared to a static control. Pressure was measured over time to determine membrane fouling and concentration polarization. The results are shown in the graphs of FIGS. 24A-24B.

Figure 24A:
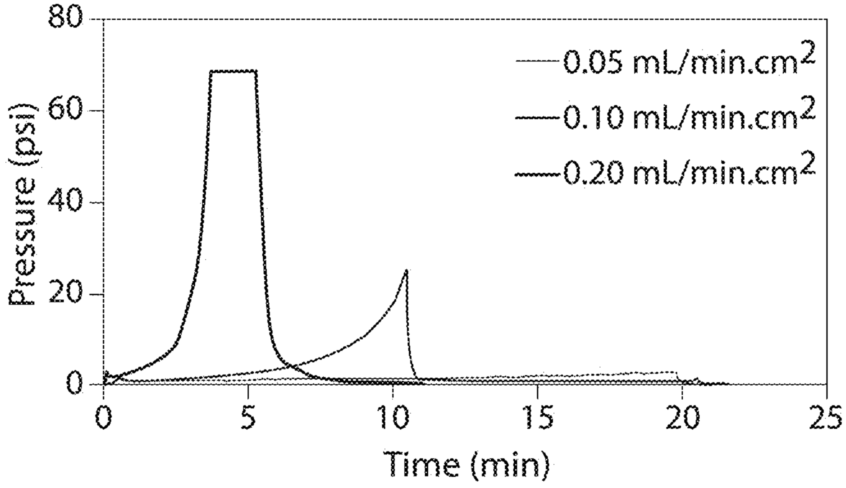
FIG. 24A is a graph showing pressure across the membrane for different loading flow rates, according to certain embodiments.
Figure 24B:
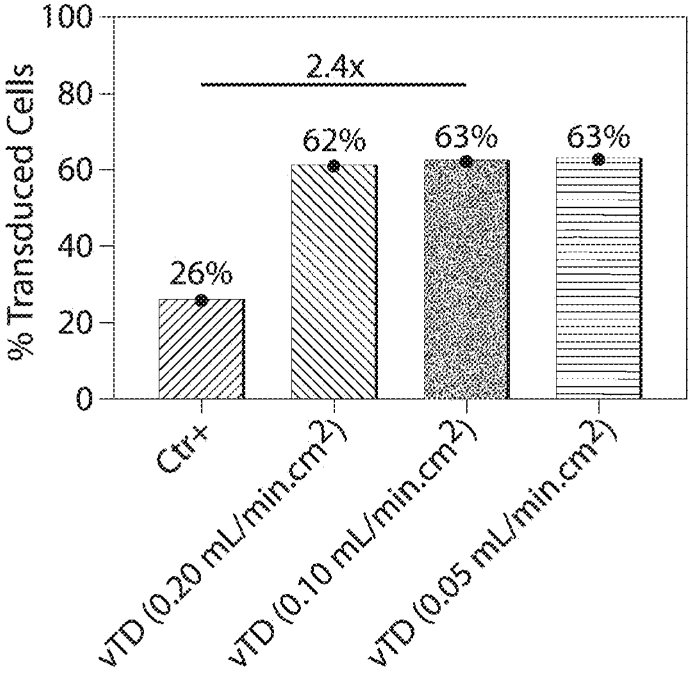
FIG. 24B is a graph showing transduction efficiency of cells treated at different loading flow rates, according to certain embodiments.

As shown in the graph of FIG. 24A, membrane fouling and concentration polarization is non-linear and depends on process flow rates. It is believed that an optimal flow rate may be selected to reduce membrane fouling and concentration polarization. The optimal flow rate may depend on composition of the media and buffers and properties of the membrane. However, as shown in FIG. 24B, transduction efficiency of the experimental samples was 2.4× of the control sample. Accordingly, even though membrane fouling and concentration polarization were increasing for the lower flow rate transductions, the results were still superior to the control sample.

Example 10: Processing Throughput and Recovery

Processing throughput of the device can be scaled linearly by changing total surface area of the membrane(s) within the device, which is a function of length, diameter, and number of membranes. The methods and devices disclosed herein may exhibit a high recovery, for example, at least 85%, at least 90%, or at least 95%, even at high cell volume.

Cells samples having $4\times10^7$ and $2.3\times10^8$ T-cells were transduced with lentivirus in the device and compared to a static control. The results are shown in the graphs of FIGS. 25A-25B.

Figure 25A:
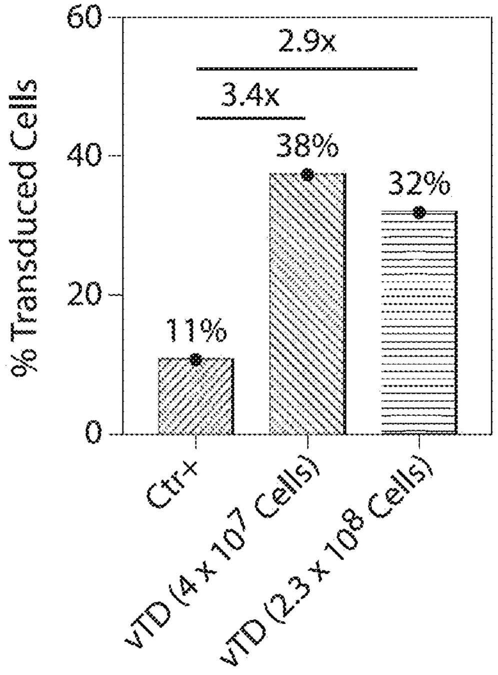
FIG. 25A is a graph showing transduction efficiency of cells treated at different cell surface densities, according to certain embodiments.
Figure 25B:
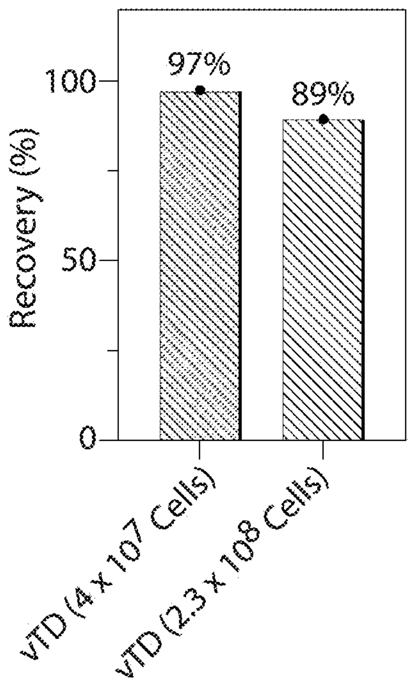
FIG. 25B is a graph showing recovery of cells for different cell surface densities, according to certain embodiments.

As shown in FIG. 25A, transduction efficiency of the experimental samples was 3.4× and 2.9×, respectively, of the control. Recovery was measured at 97% and 89%, respectively.

Accordingly, the devices disclosed herein can process a high volume of cells and produce a superior transduction efficiency than a static control while recovering almost the cells.

Example 11: Viability and Proliferation Rate

The methods and devices disclosed herein may exhibit a high viability, for example, at least 90%, 95%, 98%, at several days post-transduction, even at high cell volume. Furthermore, the methods and devices disclosed herein may exhibit a high proliferation rate, for example, at least 2-fold, 5-fold, 7-fold, and 8-fold, at several days post-transduction, even at high cell volume.

Figure 26A:
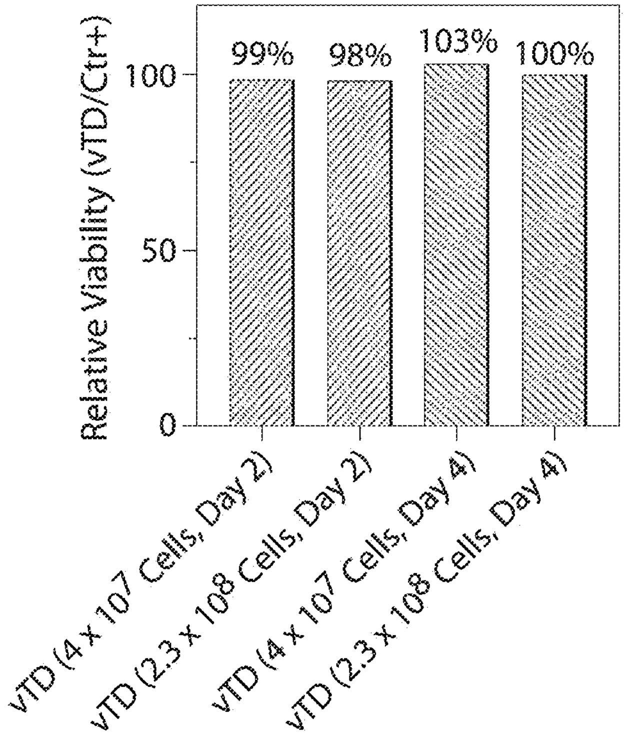
FIG. 26A is a graph showing relative viability of cells at day 2 and day 4 post-transduction for cells treated at different cell surface densities, according to certain embodiments.
Figure 26B:
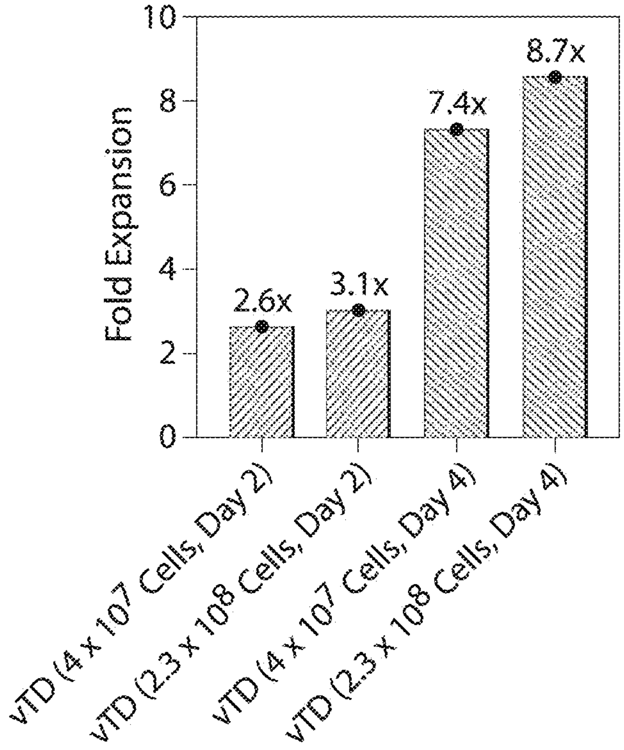
FIG. 26B is a graph showing fold expansion of cells at day 2 and day 4 post-transduction for cells treated at different cell surface densities, according to certain embodiments.

Viability and proliferation rate of the high cell volume experimental samples from Example 10 were measured on day 2 and day 4 post-transduction. The results are shown in the graphs of FIGS. 26A-26B. As shown in FIG. 26A, the samples exhibited a viability of at least 98% at day 2 and at least 100% at day 4. As shown in FIG. 26B, the cells exhibited a proliferation rate of 2.6× and 3.1× at day 2 and 7.4× and 8.7× at day 4.

Accordingly, the devices disclosed herein can process a high volume of cells, while maintaining high viability and proliferation rate of the cells.

Example 12: Membrane Pore Size and Purification of Viral Samples

Viral particle pseudotype and method of manufacturing the viral particle can result in significant inefficiencies in the transduction process. While not wishing to be bound by theory, it is believed that impurities secreted by the virus producer cell lines may competitively bind receptors on the cells to be transduced.

To purify viral samples and improve transduction, sequential delivery of viral particles followed by cells was tested in the device. Furthermore, the sequential delivery was tested with a membrane having an average pore size of 500 kD and a membrane having an average pore size of 750 kD. The experimental sequential delivery samples were compared to a mixed cell and virus sample in the 500 kD membrane device and a static control. The results are shown in the graph of FIG. 27.

Figure 27:
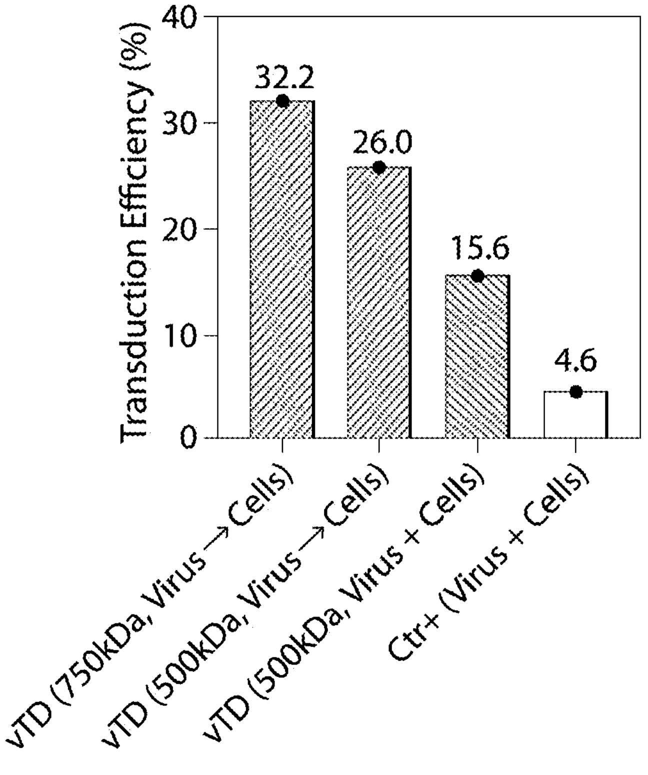
FIG. 27 is a graph showing transduction efficiency of cells treated with membranes having varying pore sizes, according to certain embodiments.

As shown in FIG. 27, the greatest transduction efficiency was exhibited by the sample for which the virus was introduced before the cells and the membrane had an average pore size of 750 kD. However, the sample for which the virus was introduced before the cells and the membrane had an average pore size of 500 kD also achieved a greater transduction efficiency than the mixed cells and virus sample and the static control.

Thus, it is believed that, for certain viral samples, purification prior to contacting the virus with the cells results in an increased transduction efficiency. Furthermore, selecting pore size of the membrane is believed to modulate retention or filtration level of the impurities.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for microfluidic cell separation. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure and are intended to be within the spirit and scope of the disclosure. In other instances, an existing system may be modified to utilize or incorporate any one or more aspects of the methods and devices described herein. Accordingly, the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. A system for treatment of cells comprising: a treatment device comprising:

an elongated housing having a luminal inlet on a first end, a luminal outlet on a second end, and a luminal recycle loop extending from the luminal outlet to the luminal inlet, and a housing inlet, a housing outlet, and a housing recycle loop extending from the housing outlet to the luminal inlet; and at least one hollow fiber semi-permeable membrane positioned within the elongated housing extending between the luminal inlet and the luminal outlet to define an interior flow chamber and an exterior flow chamber, the hollow fiber semi-permeable membrane including activation particles immobilized on a surface of the at least one hollow fiber semi-permeable membrane and the hollow fiber semi-permeable membrane having a plurality of pores dimensioned to prevent passage of cells to be treated and the activation particles and allow passage of inhibitory factors, the luminal inlet constructed and arranged to receive the cells to be treated and the activation particles;

a source of a biosample comprising the cells to be treated fluidly connected to the luminal inlet;

a source of a treatment agent comprising the activation particles fluidly connected to the luminal inlet; and at least one source of a media fluid independently fluidly connected to: one of the luminal inlet and the luminal outlet, and one of the housing inlet and the housing outlet.

2. The system of claim 1, wherein the source of the biosample is fluidly connected to the source of the treatment agent upstream from the luminal inlet to produce a mixed sample comprising the cells to be treated and the activation particles.

3. The system of claim 2, further comprising a mixer fluidly connected to the source of the biosample and the source of the treatment agent, configured to produce the mixed sample.

4. The system of claim 2, wherein the mixed sample is substantially homogenous.

5. The system of claim 1, wherein the biosample and the treatment agent are each independently fluidly connected to the luminal inlet.

6. The system of claim 1, further comprising a priming fluid fluidly connected to at least one of the luminal inlet and the luminal outlet.

7. The system of claim 1, wherein the cells to be treated comprise at least one of stem cells, immune cells, cancer cells, engineered cells, primary cells, T-cells, primary T-cells, regulatory T-cells, NK cells, B cells, and hematopoietic stem cells (HSC).

8. The system of claim 1, further comprising at least one of a luminal inlet pump, a housing inlet pump, a luminal inlet valve, a luminal outlet valve, a housing inlet valve, a housing outlet valve, a biosample valve, a treatment agent valve, and at least one media fluid valve.

9. The system of claim 8, wherein at least one of the luminal inlet pump and the housing inlet pump is configured to operate at an oscillatory flow.

10. The system of claim 8, further comprising a controller operably connected to at least one of the luminal inlet pump, the housing inlet pump, the luminal inlet valve, the luminal outlet valve, the housing inlet valve, the housing outlet valve, the biosample valve, the treatment agent valve, and the at least one media fluid valve.

11. The system of claim 10, wherein the controller is configured to:

actuate at least one of the luminal inlet pump, the luminal inlet valve, the biosample valve, the treatment agent valve, and the housing outlet valve to introduce the biosample comprising the cells to be treated, and actuate at least one of the luminal inlet pump, the luminal inlet valve, the at least one media fluid valve, and the housing outlet valve to introduce the media fluid to co-localize the cells to be treated.

12. The system of claim 10, wherein the controller is configured to:

actuate at least one of the luminal inlet pump, the luminal inlet valve, the at least one media fluid valve, and the luminal outlet valve to introduce the media fluid to suspend the treated cells in an intermediate sample, actuate at least one of the housing inlet pump, the housing inlet valve, the at least one media fluid valve, and the housing outlet valve to introduce the media fluid to release the treated cells from a surface of the hollow fiber semi-permeable membrane, and actuate at least one of the luminal outlet valve and the luminal inlet valve to remove a treated cell sample comprising the treated cells and the activation particles from the treatment device.

13. The system of claim 10, further comprising a pressure sensor configured to measure pressure at a target location within the system.

14. The system of claim 13, wherein the pressure sensor is operably connected to the controller, the controller configured to actuate one or more of the luminal inlet pump, the housing inlet pump, the luminal inlet valve, the luminal outlet valve, the housing inlet valve, the housing outlet valve, the biosample valve, the treatment agent valve, and the least one media fluid valve responsive to a pressure measurement obtained by the pressure sensor.

15. The system of claim 10, further comprising a weight sensor configured to measure weight at a target location within the system.

16. The system of claim 15, wherein the weight sensor is operably connected to the controller, the controller configured to notify a user responsive to a weight measurement obtained by the weight sensor.

17. The system of claim 10, further comprising a bubble sensor configured to detect bubbles within the treatment device.

18. The system of claim 17, wherein the bubble sensor is operably connected to the controller, the controller configured to actuate one or more of the luminal inlet pump, the housing inlet pump, the luminal inlet valve, the luminal outlet valve, the housing inlet valve, and the housing outlet valve responsive to a bubble detected by the bubble sensor.

19. The system of claim 1, further comprising a pH control unit configured to control pH of a fluid within the treatment device.

20. The system of claim 19, further comprising a pH sensor operably connected to the pH control unit configured to control pH within the treatment device responsive to a pH measurement obtained by the pH sensor.

21. A system for treatment of cells with activation particles comprising: a treatment device comprising:

an elongated housing having a luminal inlet on a first end, a luminal outlet on a second end, and a housing inlet and a housing outlet, the elongated housing defining a housing recycle loop extending between the housing outlet and both the luminal inlet and the housing inlet, and a luminal recycle loop extending between the luminal outlet and the luminal inlet; and at least one hollow fiber semi-permeable membrane positioned within the elongated housing extending between the luminal inlet and the luminal outlet to define an interior flow chamber and an exterior flow chamber, the hollow fiber semi-permeable membrane having a plurality of pores dimensioned to prevent passage of cells to be treated and the activation particles, the activation particles being bound to a lumen-side surface and immobilized on the lumen-side surface of the hollow fiber semi-permeable membrane;

a source of a biosample comprising the cells to be treated fluidly connected to the luminal inlet; and at least one source of a media fluid independently fluidly connected to: one of the luminal inlet and the luminal outlet, and one of the housing inlet and the housing outlet.

22. A device dimensioned for treatment of a target number of cells with activation particles, the device comprising:

an elongated housing having a luminal inlet on a first end, a luminal outlet on a second end, and a housing inlet and a housing outlet, the elongated housing defining a housing recycle loop extending between the housing outlet and both the luminal inlet and the housing inlet, and a luminal recycle loop extending between the luminal outlet and the luminal inlet; and at least one primed hollow fiber semi-permeable membrane positioned within the elongated housing extending between the luminal inlet and the luminal outlet to define an interior flow chamber and an exterior flow chamber, the at least one hollow fiber semi-permeable membrane having a plurality of pores dimensioned to prevent passage of the cells to be treated and an interior surface area of between about 20 $mm^2$ and about 250 $mm^2$ for every 1 million cells to be treated and having a surface modified by surface-bound transduction enhancers, the activation particles being bound to and immobilized on a lumen side of the hollow fiber semi permeable, and the cells to be activated are distributed as a monolayer for interaction with the bound activation particles.

* * * * *